United States Patent
Forrest et al.

(10) Patent No.: US 11,458,163 B2
(45) Date of Patent: Oct. 4, 2022

(54) PLATINUM(IV) CONJUGATES AND METHODS OF USE

(71) Applicants: University of Kansas, Lawrence, KS (US); HylaPharm, LLC, Lawrence, KS (US)

(72) Inventors: Laird Forrest, Lawrence, KS (US); Daniel Aires, Mission Hills, KS (US); Ryan Moulder, Lawrence, KS (US); Ruolin Lu, Lawrence, KS (US); Jordan Hunt, Lawrence, KS (US); Peter Kleindl, Lawrence, KS (US); Ti Zhang, Lawrence, KS (US); Chad Groer, Lawrence, KS (US); Shuang Cai, Lawrence, KS (US)

(73) Assignees: University of Kansas, Lawrence, KS (US); HylaPharm, LLC, Lawrence, KS (US)

( * ) Notice: Subject to any disclaimer, the term of this patent is extended or adjusted under 35 U.S.C. 154(b) by 0 days.

(21) Appl. No.: 16/850,748

(22) Filed: Apr. 16, 2020

(65) Prior Publication Data

US 2020/0330507 A1 Oct. 22, 2020

Related U.S. Application Data

(60) Provisional application No. 62/835,408, filed on Apr. 17, 2019.

(51) Int. Cl.
| | |
|---|---|
| *A61K 33/243* | (2019.01) |
| *C07F 15/00* | (2006.01) |
| *A61P 35/00* | (2006.01) |
| *A61K 45/06* | (2006.01) |
| *A61K 47/36* | (2006.01) |

(52) U.S. Cl.
CPC ............ *A61K 33/243* (2019.01); *A61K 45/06* (2013.01); *A61K 47/36* (2013.01); *A61P 35/00* (2018.01); *C07F 15/0093* (2013.01)

(58) Field of Classification Search
CPC ..... C07F 15/0093; A61K 47/36; A61K 47/61; A61K 31/555; A61K 9/1075; A61K 33/243; A61K 9/0019; A61K 45/06; A61K 47/22; A61K 47/551; A61K 2300/00; A61P 35/00

See application file for complete search history.

(56) References Cited

U.S. PATENT DOCUMENTS

| | | | |
|---|---|---|---|
| 4,698,348 A | 10/1987 | Gerster | |
| 7,884,207 B2 | 2/2011 | Stoermer et al. | |
| 2014/0274988 A1* | 9/2014 | Lippard | ............... A61K 31/555 514/186 |

OTHER PUBLICATIONS

Gerster, et al., "Synthesis and Structure—Activity-Relationships of 1H-Imidazo[4,5-c]quinolines That Induce Interferon Production," Journal of Medicinal Chemistry, 2005, vol. 28, No. 2, pp. 3481-3491.
International Search Report and Written Opinion in International Patent Application No. PCT/US2020/028468 dated Sep. 4, 2020.
Larson, et al., "Design and Synthesis of N1-Modified Imidazoquinoline Agonists for Selective Activation of Toll-Like Receptors 7 and 8," ACS Medicinal Chemistry Letters, 2017, vol. 8, pp. 1148-1152.

\* cited by examiner

*Primary Examiner* — Doan T Phan
(74) *Attorney, Agent, or Firm* — Foley & Lardner LLP

(57) ABSTRACT

Provided are platinum(IV) compounds of Formula I (I)

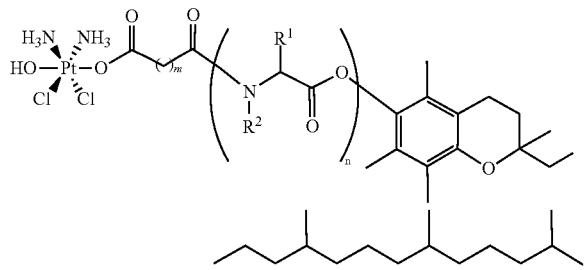

or pharmaceutically acceptable salts thereof. Also provided are compositions including such compounds as well as methods of using the same.

30 Claims, 10 Drawing Sheets

Day 0: Prestudy Recurrent Sarcoma

Day 60: After 2PT4trt

Prestudy

After 4th injection

Prestudy

After 5$^{th}$ injection

Prestudy

After 10th injection

PLATINUM(IV) CONJUGATES AND METHODS OF USE

CROSS-REFERENCE TO RELATED APPLICATIONS

This application claims the benefit of and priority to U.S. Provisional Application 62/835,408, filed Apr. 17, 2019, the entire contents of which are incorporated herein by reference.

U.S. GOVERNMENT RIGHTS

This invention was made with government support under CA173292 awarded by the National Institutes of Health. The government has certain rights in the invention.

FIELD

This disclosure relates generally to compounds and compositions for the treatment of cancers and methods of using the same.

SUMMARY

In an aspect, a compound of Formula I is provided:

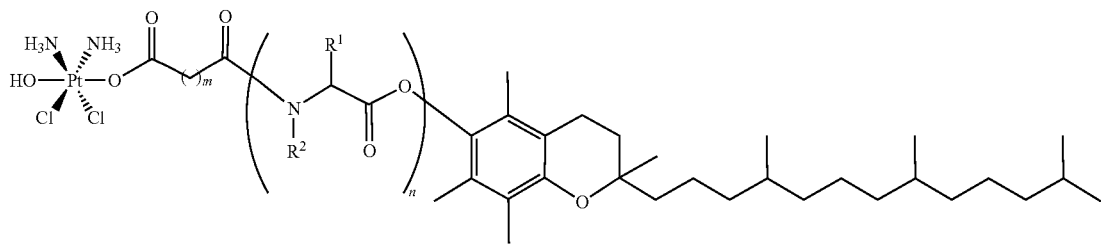

(I)

or a pharmaceutically acceptable salt thereof, wherein independently at each occurrence $R^2$ is H and $R^1$ is H, —$CH_3$, —$CH_2C(O)NH_2$, —$CH_2C(O)OH$, —$CH_2CH_2C(O)OH$, —$CH_2CH_2C(O)NH_2$, —$CH_2SH$, —$CH_2OH$, —$CH_2NH_2$, —$CH(OH)CH_3$, —$CH_2CH(CH_3)_2$, —$CH_2CH_2CH_2CH_2NH_2$, —$CH_2CH_2SCH_3$, benzyl, —$CH(CH_3)CH_2CH_3$, —$CH(CH_3)_2$,

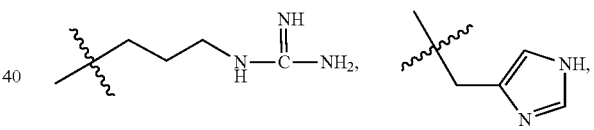

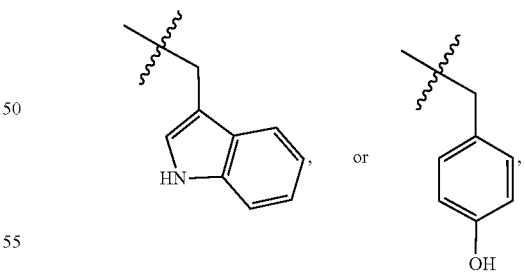

or $R^1$ and $R^2$ together form —$CH_2CH_2CH_2$—;
m is 2, 3, 4, 5, 6, 7, or 8; and
n is 1, 2, or 3.

In an aspect, a composition is provided that includes a compound of Formula I, or a pharmaceutically acceptable salt thereof, and a hyaluronan-tocopherol conjugate. In any embodiment herein, it may be that the hyaluronan-tocopherol conjugate is of Formula II, III, IV, V, or a mixture of any two or more thereof:

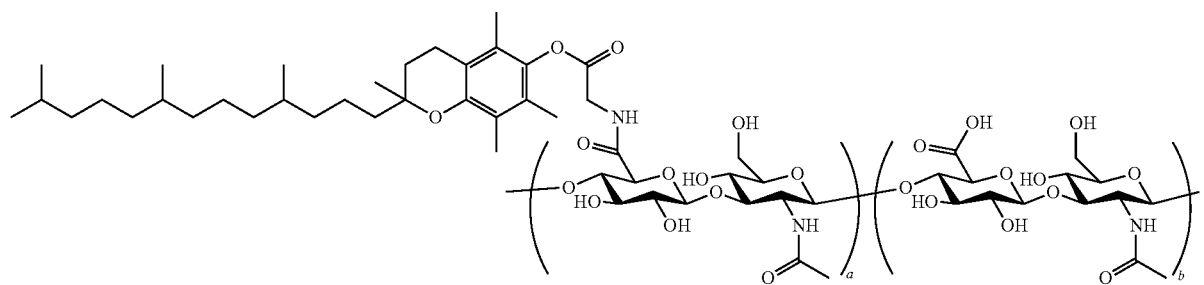

(II)

or a pharmaceutically acceptable salt thereof,

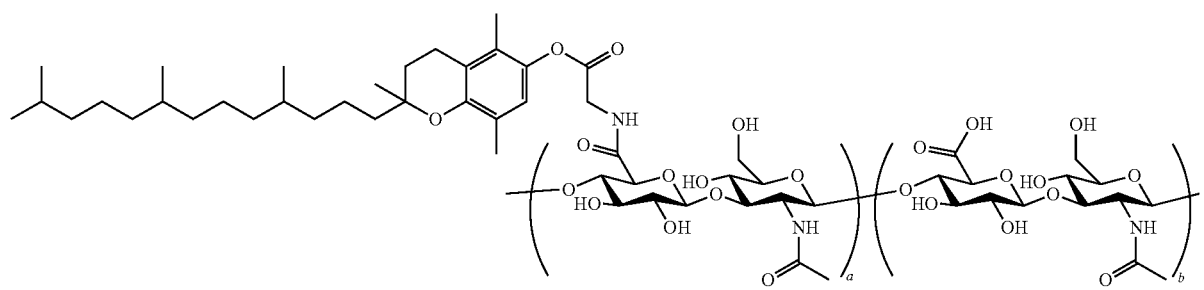

(III)

or a pharmaceutically acceptable salt thereof,

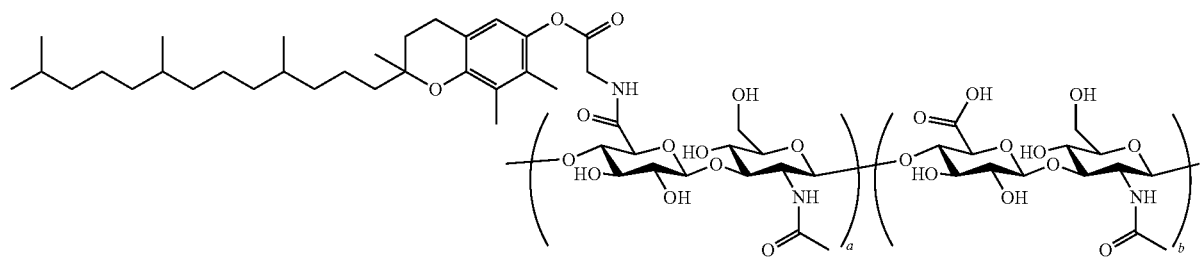

(IV)

or a pharmaceutically acceptable salt thereof,

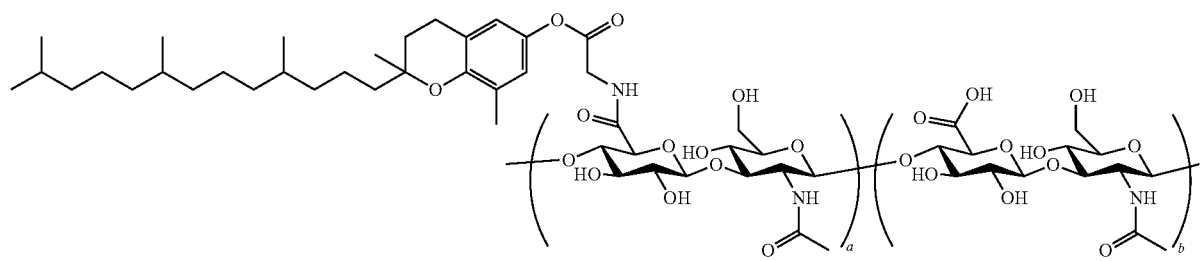

(V)

or a pharmaceutically acceptable salt thereof, wherein a is independently at each occurrence from 1 to 800 and b is independently at each occurrence from 18 to 2540.

In an aspect, a method of slowing the proliferation of a cancer cell is provided, the method comprising contacting the cell with the compound of Formula I or pharmaceutically acceptable salt thereof or the composition of any embodiment herein.

In an aspect, a method of slowing or reversing the growth of a tumor in a subject in need thereof is provided, the method comprising administering an effective amount of the compound of Formula I or pharmaceutically acceptable salt thereof or the composition of any embodiment herein, to the subject.

In an aspect, a method of treating cancer in a subject in need thereof is provided, comprising administering an effective amount of the compound of Formula I or pharmaceutically acceptable salt thereof or the composition of any embodiment herein, to the subject.

BRIEF DESCRIPTION OF THE DRAWINGS

FIG. 6A illustrates the tumor prior to the first treatment and FIG. 6B illustrates the tumor prior to the third treatment.

FIG. 7A illustrates the tumor prior to the first treatment and FIG. 7B illustrates that there is no gross evidence of tumor after the fourth treatment.

FIG. 8A illustrates the tumor prior to the first treatment and FIG. 8B illustrates that there is no gross evidence of tumor after the fifth treatment.

FIG. 9A illustrates the tumor prior to the first treatment and FIG. 9B shows the previous tumor site with black melanocytic pigments but no measurable growth.

DETAILED DESCRIPTION

Figure 1:
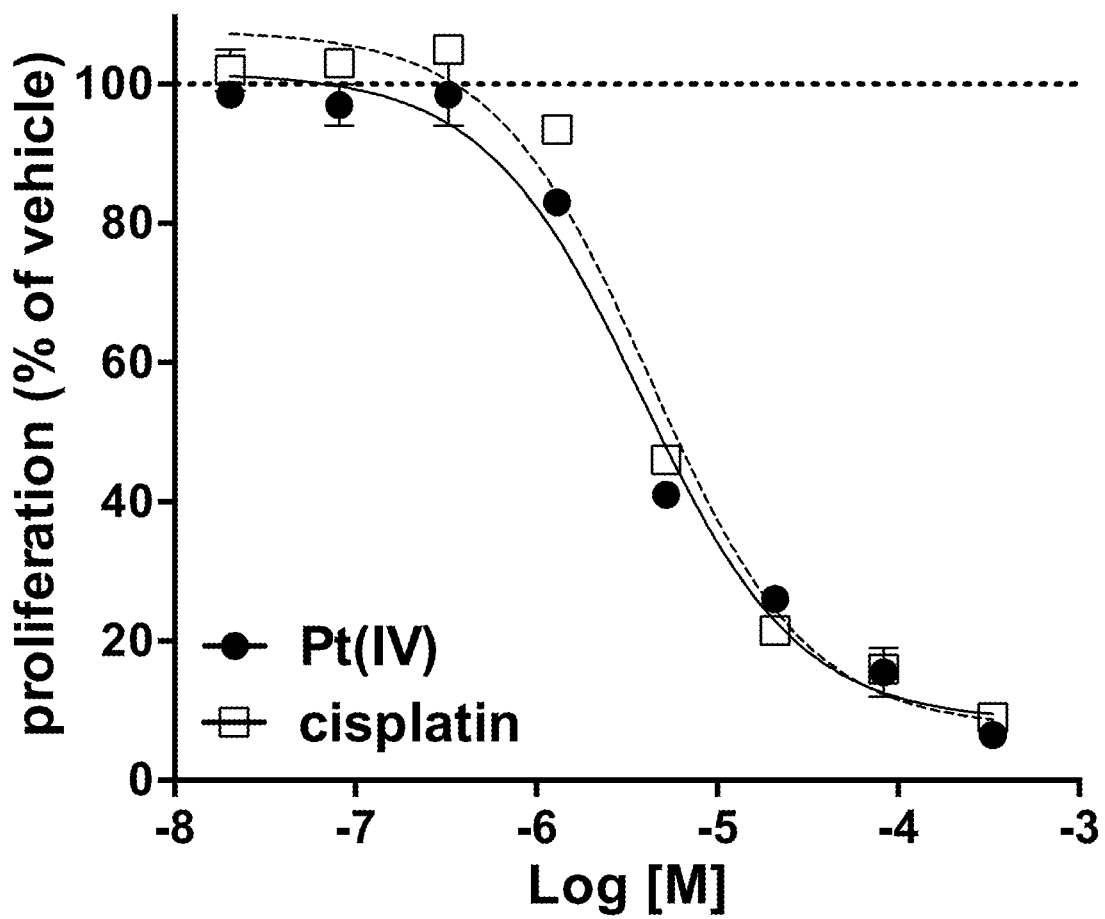
FIG. 1 provides the results of studies evidencing compounds and compositions of the present technology inhibit the growth of head and neck squamous cell carcinoma cells, according to the Examples. AT84 cells were cultured in the presence of increasing concentrations of a composition of the present technology (a "Pt(IV)-toco/HA-toco composition") or cisplatin for 72 hours and cell proliferation was quantified. Data from at least five separate experiments was analyzed by non-linear regression. Representative dose response curves are shown. Both drugs show full efficacy and similar potencies: Pt(IV)-toco/HA-toco composition $IC_{50}=6.1\pm1.1$ μM and cisplatin $IC_{50}=3.0\pm0.26$ μM (n=7-8).

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 wt. %" would be understood to mean "9 wt. % to 11 wt. %." It is to be understood that when "about" precedes a term, the term is to be construed as disclosing "about" the term as well as the term without modification by "about"—for example, "about 10 wt. %" discloses "9 wt. % to 11 wt. %" as well as disclosing "10 wt. %."

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more. than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

As understood by one of ordinary skill in the art, "molecular weight" (also known as "relative molar mass") is a dimensionless quantity but is converted to molar mass by multiplying by 1 gram/mole or by multiplying by 1 Da—for example, a compound with a weight-average molecular weight of 5,000 has a weight-average molar mass of 5,000 g/mol and a weight-average molar mass of 5,000 Da.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, or a hydroxyl group(s) it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms. The phrase "and/or" as used in this paragraph and the present disclosure will be understood to mean any one of the recited members individually or a combination of any two or more thereof—for example, "A, B, and/or C" would mean "A, B, C, A and B, A and C, or B and C."

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

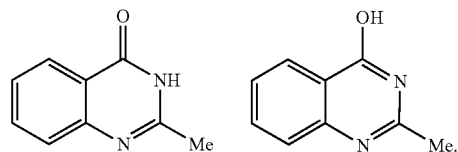

As another example, guanidines may exhibit the following isomeric forms in protic organic solution, also referred to as tautomers of each other:

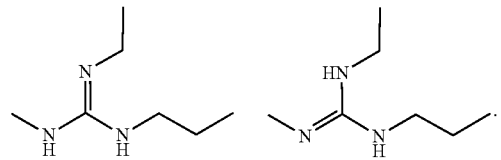

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

As used herein, the terms "subject," "individual," or "patient" can be an individual organism, a vertebrate, a mammal, or a human. "Mammal" includes a human, non-human primate, murine (e.g., mouse, rat, guinea pig, hamster), ovine, bovine, ruminant, lagomorph, porcine, caprine, equine, canine, feline, avis, etc. In any embodiment herein, it may be that the mammal is feline or canine. In any embodiment herein, it may be that the mammal is human.

The term "administering" a compound or composition to a subject means delivering the compound to the subject. "Administering" includes prophylactic administration of the compound or composition (i.e., before the disease and/or one or more symptoms of the disease are detectable) and/or therapeutic administration of the composition (i.e., after the disease and/or one or more symptoms of the disease are detectable). The methods of the present technology include administering one or more compounds or agents. If more than one compound is to be administered, the compounds may be administered together at substantially the same time, and/or administered at different times in any order. Also, the compounds of the present technology may be administered before, concomitantly with, and/or after administration of another type of drug or therapeutic procedure (e.g., surgery).

As used herein, the term "amino acid" is used to refer to any organic molecule that contains at least one amino group and at least one carboxyl group where the at least one amino group is at the a position relative to the carboxyl group, where the amino acid is in the L-configuration. Naturally occurring amino acids include, for example, the twenty most common levorotatory (L,) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Naturally-occurring amino acids are those encoded by the genetic code, as well as those amino acids that are later modified, e.g., hydroxyproline, γ-carboxyglutamate, and O-phosphoserine. Amino acids may be referred to herein by either their commonly known three letter symbols or by the one-letter symbols recommended by the IUPAC-IUB Biochemical Nomenclature Commission.

As used herein, the terms "polypeptide," "polyamino acid," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

"Treating," "treat," "treated," or "treatment" as used herein covers the treatment of a disease or disorder described herein in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, ameliorating, or slowing progression of one or more symptoms of the disease or disorder. Symptoms may be assessed by methods known in the art or described herein, for example, biopsy, histology, and blood tests to determine relevant enzyme levels, metabolites or circulating antigen or antibody (or other biomarkers), quality of life questionnaires, patient-reported symptom scores, and imaging tests. In any embodiment herein, it may be that treatment is assessed my measurement of tumor volume or mass.

"Slowing," "ameliorate," "ameliorating," and the like, as used herein, refer to inhibiting, relieving, eliminating, or slowing progression of one or more symptoms, i.e., cell proliferation or tumor growth.

As used herein, "prevention," "prevents," or "preventing" of a disorder or condition refers to a compound that, in a statistical sample, reduces the occurrence of the disorder, symptom, or condition in the treated sample relative to a control subject, or delays the onset of one or more symptoms of the disorder or condition relative to the control subject.

The term "conjugate" as used herein refers to a product in which a compound (e.g., tocopherol) is covalently attached to a different compound (e.g., a polysaccharide such as hyaluronan). The attachment may be a direct covalent attachment, for example, via a peptide bond, or by way of a linker. Linkers may include any amino acid, polypeptide, polynucleotide, optionally substituted hydrocarbon, or a combination thereof.

Throughout this disclosure, various publications, patents and published patent specifications are referenced by an identifying citation. Also within this disclosure are Arabic numerals referring to referenced citations, the full bibliographic details of which are provided subsequent to the Examples section. The disclosures of these publications, patents and published patent specifications are hereby incorporated by reference into the present disclosure to more fully describe the present technology.

The Present Technology

Head and neck cancers (HNCs) are a group of cancers called collectively as HNCs as they all occur in the head and neck. In people, HNCs are the sixth most common cancer worldwide with over 630,000 new diagnoses each year and with an estimated incidence rate of 65,000 in the United States alone (1). HNCs are categorized based on the anatomical sites where they originate. In people, HNCs contain cancers of the oral cavity including the lips, the tongue, the gums, the hard palate, and the floor of the mouth, the nasal cavity and paranasal sinuses, the salivary glands, the pharynx (throat), and the larynx (vocal cords) (2). In pet dogs and cats, HNCs include oral tumors, salivary gland tumors, nasal tumors, ocular and periocular tumors, aural tumors, skull tumors, esophageal tumors, laryngeal and tracheal tumors (3). When classified by the cell type from which the HNCs originate, 90% of human HNCs are squamous cell carcinomas (SCCs). Though lack of a definitive epidemiology, oral melanoma, oral SCC and oral fibrosarcoma are thought by veterinarians to be the most common HNCs in dogs; whereas oral SCC is the most prevalent oral malignancies in cats (3).

Treatment options for HNCs in people include three conventional modalities that are surgery, radiation therapy and chemotherapy, as well as the newer targeted therapies such as epidermal growth factor receptor (EGFR) inhibitors (e.g. Cetuximab) and checkpoint inhibitor immunotherapies disrupting the interactions between the programmed cell death protein 1 (PD1) and the programmed death ligand 1 (PDL1) (e.g., Pembrolizumab and Nivolumab) (4). In veterinary oncology, the three main categories of conventional therapy have been widely adapted although targeted therapy and immunotherapy using caninized and felinized antibodies are still in preclinical development.

Remaining as the primary therapy for operable HNCs, common surgical options include traditional excision of the primary lesion and lymphadenectomy, endoscopic surgery, transoral robotic surgery, transoral laser microsurgery and other image-guided, computer-enhanced surgical procedures (5). Modern radiation therapy utilizes an external beam radiation machine (linear accelerator) that delivers high-energy radiation beams to the tumor, or an implantable radioactive material inserted in or near the tumor, as well as an internal radiotherapy method such as the use of radioactive iodine for thyroid cancer. Traditional chemotherapeutic agents often used in the treatment of HNCs include cisplatin, carboplatin, fluorouracil, paclitaxel and docetaxel. The selection of treatment modalities depends primarily on the location and the stage of the HNCs, in which concurrent and sequential uses of multiple modalities are common practices in the paradigm of HNC oncology.

Previous preclinical and canine clinical studies of an intralesional platinum(II) delivery system, in which hyaluronan-conjugated cisplatin (HylaPlat) was administered intra-tumorally to laboratory mice with HNCs and to pet dogs with spontaneous cancers including HNCs have been done. The intraleisonal HylaPlat demonstrated sustained release and prolonged retention of platinum in the lesion and the surrounding lymphatic basin in mice and rats (6-11), resulted in remarkably high ratio of platinum contents in the tumor tissues compared to the systemic circulation in dogs (12), and later translated into anti-cancer efficacy against HNCs in laboratory mice (13-15) and in pet dogs with naturally occurring malignancies (16,17). HylaPlat was shown to be absent of histologically evident injection-site reactions and systemic side effects such as renal and hepatic toxicities in rodents; however, canine clinical studies revealed myelosuppression, neutropenia, and liver injury, possibly due to the reactivity of the liberated platinum(II) from the loosely bound hyaluronan carriers in the form of diaquated cisplatin that subsequently entered circulatory system, bone marrow and liver (16).

To improve the toxicology and the pharmacodynamics of intralesional platinum therapy, development of a toxicologically inert version of the highly effective chemotherapeutic is needed.

Platinum(IV) chemistry has been investigated by medicinal chemists for several decades and various mono-, di- and mixed axial-functionalized molecules have been synthesized and reported as platinum(II) prodrugs (27-30) with different activities. Among them, three platinum(IV) molecules have advanced into clinical studies but none has received FDA approval, including tetraplatin (31,32), iproplatin (33,34), and the orally bioavailable satraplatin (35,36).

More specifically, syntheses of lipophilic Pt(IV) compounds with one of their axial positions occupied by a fatty acid ester or an α-tocopherol molecule have been reported and their activities have been tested in cells and mouse tumor models (37,38). Furthermore, the delivery of platinum (IV) using different passively targeted nanoconjugates has been realized in the forms of, for example, a dextran-platinum(IV) conjugate and an ethylenediamine modified hyaluronic acid-platinum(IV) conjugate in preclinical studies (39,40).

In an aspect, the present technology provides a compound of Formula I

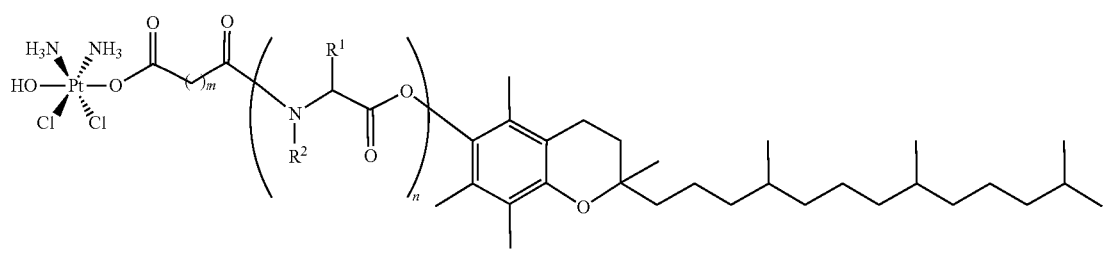

(I)

or a pharmaceutically acceptable salt thereof, wherein
independently at each occurrence $R^2$ is H and $R^1$ is H, —$CH_3$, —$CH_2C(O)NH_2$, —$CH_2C(O)OH$, —$CH_2CH_2C(O)OH$, —$CH_2CH_2C(O)NH_2$, —$CH_2SH$, —$CH_2OH$, —$CH_2NH_2$, —$CH(OH)CH_3$, —$CH_2CH(CH_3)_2$, —$CH_2CH_2CH_2CH_2NH_2$, —$CH_2CH_2SCH_3$, benzyl, —$CH(CH_3)CH_2CH_3$, —$CH(CH_3)_2$,

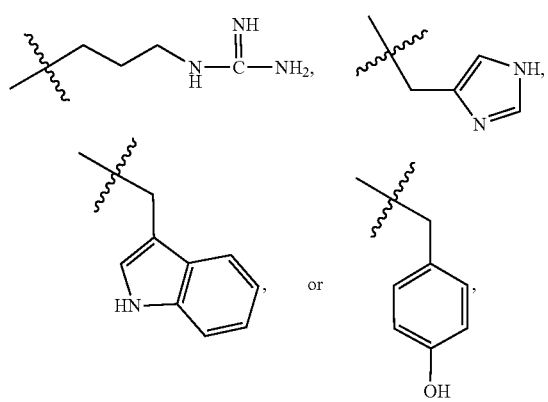

or $R^1$ and $R^2$ together form —$CH_2CH_2CH_2$—;

m is 2, 3, 4, 5, 6, 7, or 8; and n is 1, 2, or 3.

The compounds of the present technology exhibit a more inert nature than the platinum(II) compounds as a result of the altered reduction kinetics of the platinum(IV), making the compounds of the present technology less likely to cause dose-limiting side effects as seen in cisplatin, as well as due to improved cellular accumulation and greater lipophilicity, properties that also facilitate the encapsulation or complexation of these compounds into nanocarriers.

In any embodiment herein, the compound may be of Formula Ia

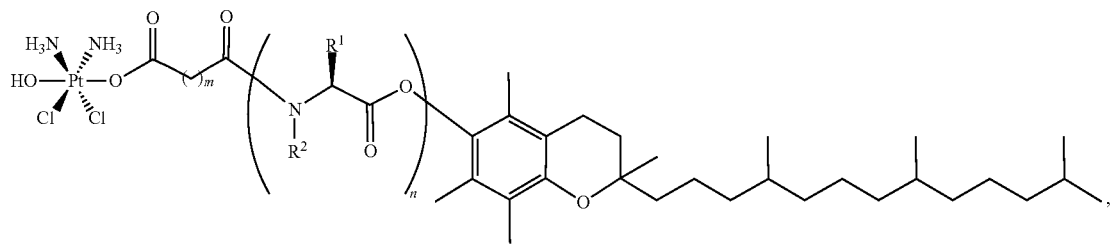

(Ia)

or a pharmaceutically acceptable salt thereof.

In any embodiment herein, it may be that m is 2. In any embodiment herein, it may be that m is 3. In any embodiment herein, it may be that m is 4. In any embodiment herein, it may be that m is 5. In any embodiment herein, it may be that m is 6. In any embodiment herein, it may be that m is 7. In any embodiment herein, it may be that m is 8. In any embodiment herein, it may be that n is 1. In any embodiment herein, it may be that n is 2. In any embodiment herein, it may be that n is 3. In any embodiment herein, it may be that n is 1 and m is 2. In any embodiment herein, it may be that $R^1$ is H. In any embodiment herein, it may be that $R^1$ is H and $R^2$ is H.

In any embodiment herein, it may be that the compound has the formula

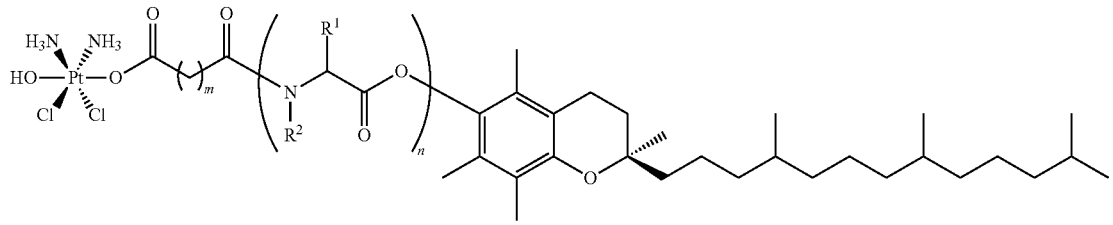

or a pharmaceutically acceptable salt thereof. In any embodiment herein, it may be that the compound has the formula

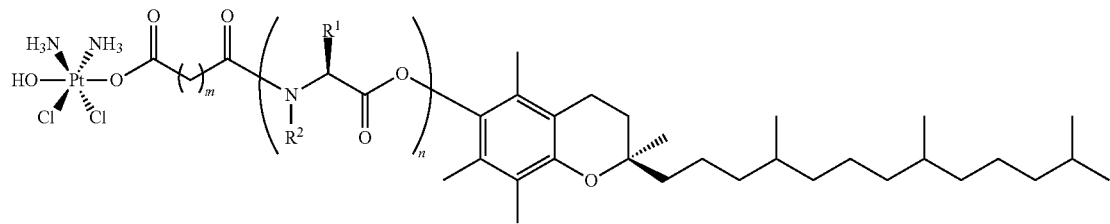

or a pharmaceutically acceptable salt thereof.

In any embodiment herein, it may be that the compound has the formula

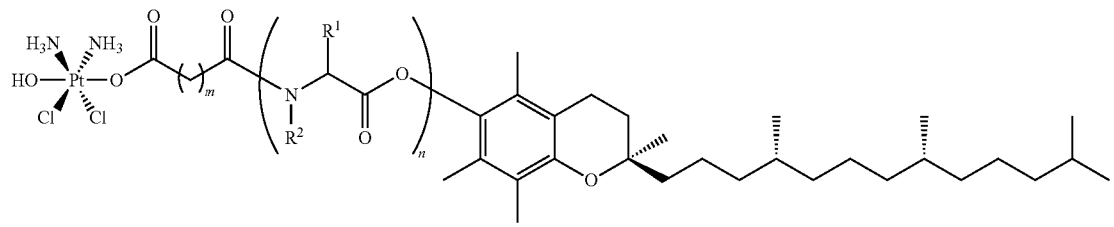

or a pharmaceutically acceptable salt thereof. In any embodiment herein, it may be that the compound has the formula

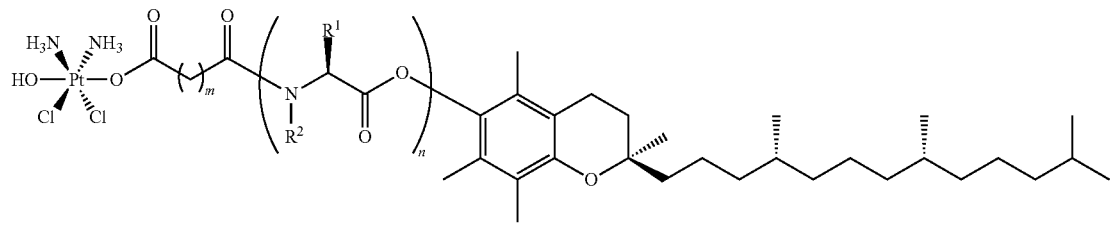

or a pharmaceutically acceptable salt thereof.

In any embodiment herein, it may be that the compound has the formula

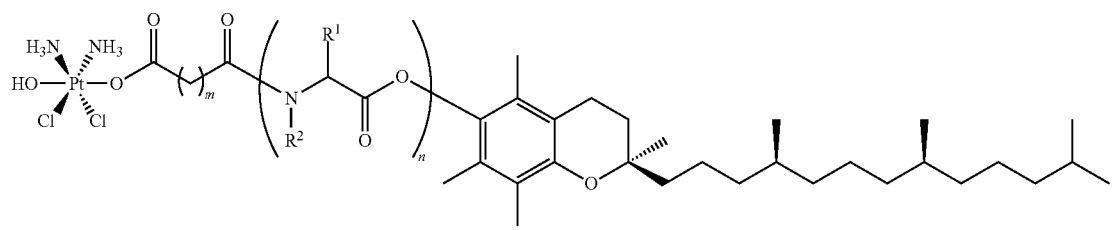

or a pharmaceutically acceptable salt thereof. In any embodiment herein, it may be that the compound has the formula

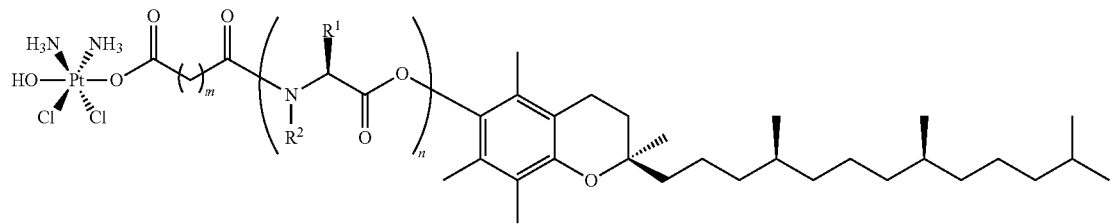

or a pharmaceutically acceptable salt thereof.

In any embodiment herein, it may be that the compound has the formula

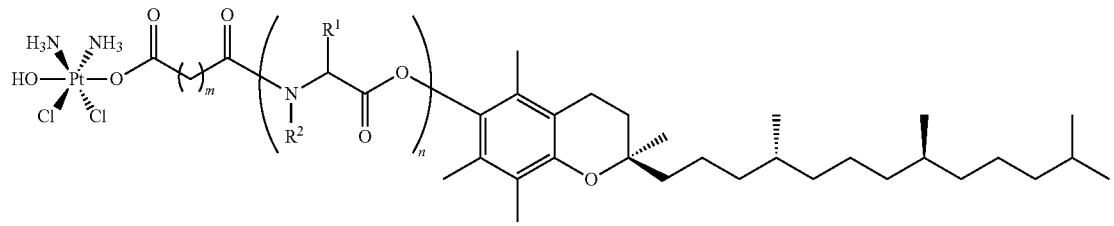

or a pharmaceutically acceptable salt thereof. In any embodiment herein, it may be that the compound has the formula

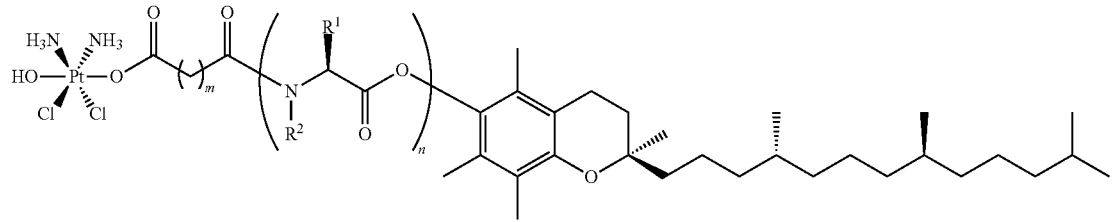

or a pharmaceutically acceptable salt thereof.

In any embodiment herein, it may be that the compound has the formula

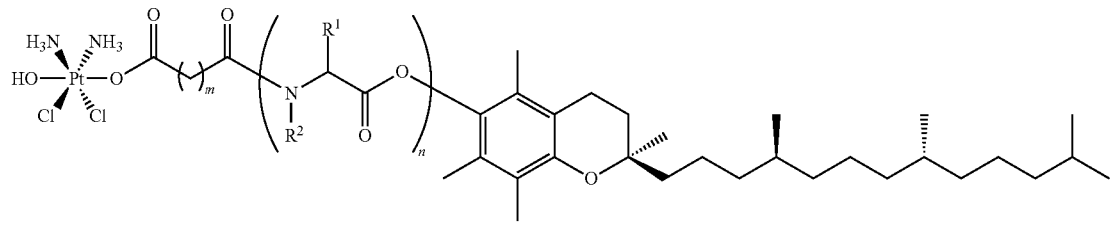

or a pharmaceutically acceptable salt thereof. In any embodiment herein, it may be that the compound has the formula

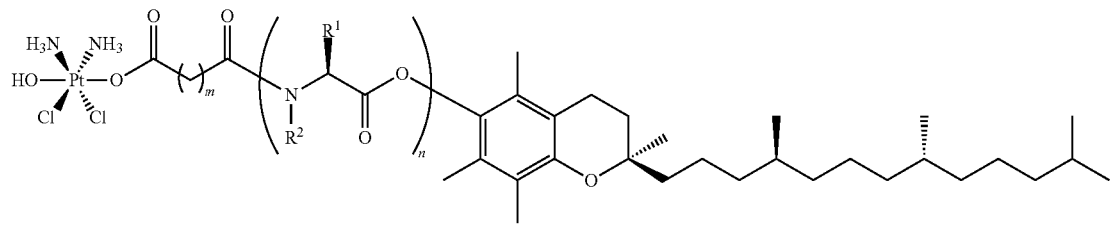

or a pharmaceutically acceptable salt thereof.

In any embodiment herein, it may be that the compound has the formula

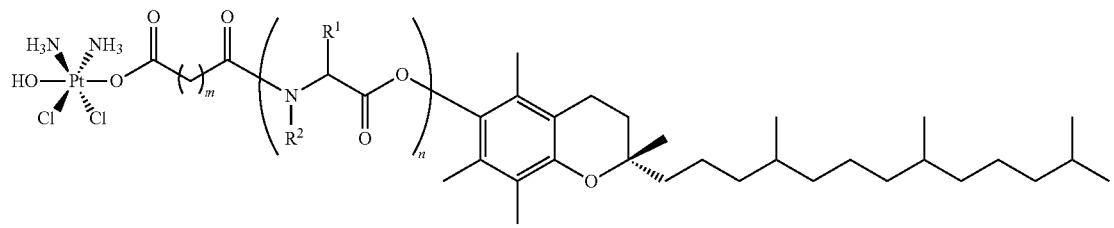

or a pharmaceutically acceptable salt thereof. In any embodiment herein, it may be that the compound has the formula

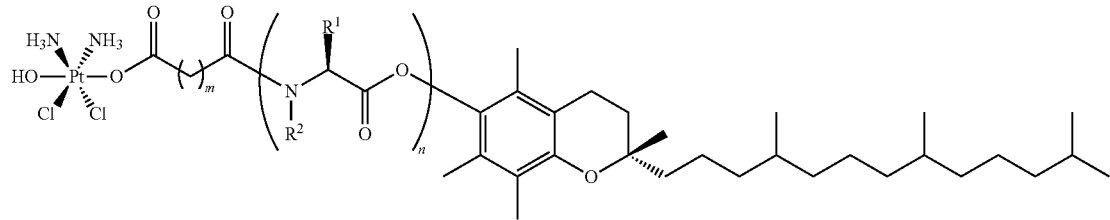

or a pharmaceutically acceptable salt thereof.

In any embodiment herein, it may be that the compound has the formula

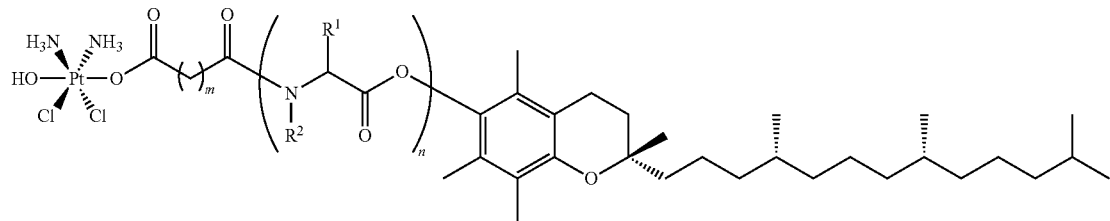

or a pharmaceutically acceptable salt thereof. In any embodiment herein, it may be that the compound has the formula

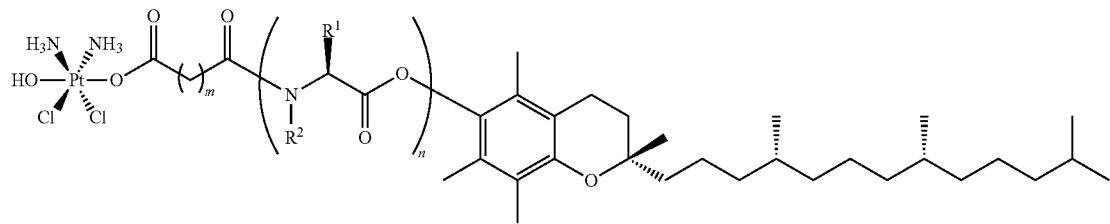

or a pharmaceutically acceptable salt thereof.

In any embodiment herein, it may be that the compound has the formula

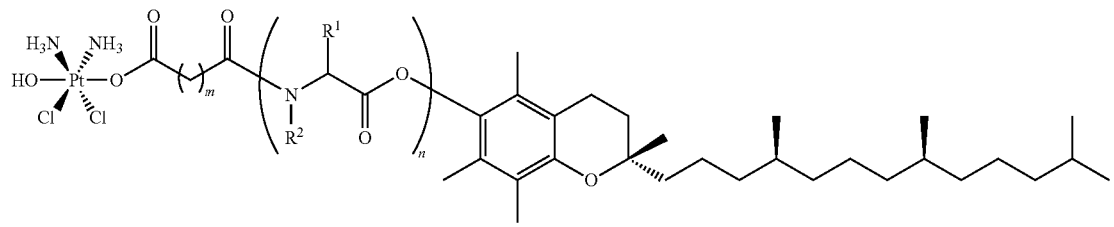

or a pharmaceutically acceptable salt thereof. In any embodiment herein, it may be that the compound has the formula

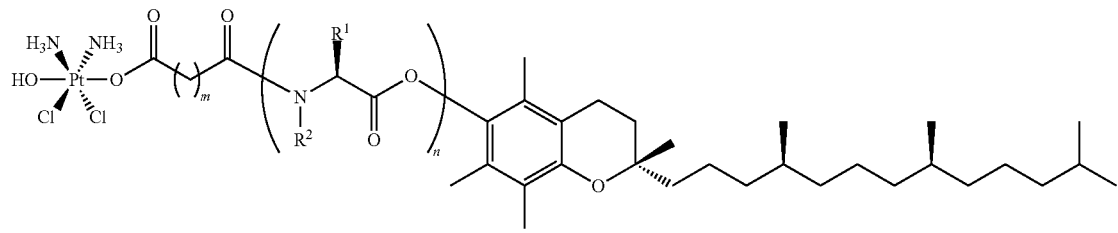

or a pharmaceutically acceptable salt thereof.

In any embodiment herein, it may be that the compound has the formula

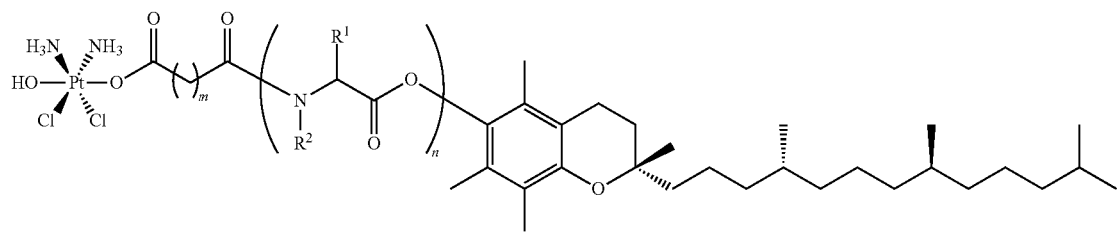

or a pharmaceutically acceptable salt thereof. In any embodiment herein, it may be that the compound has the formula

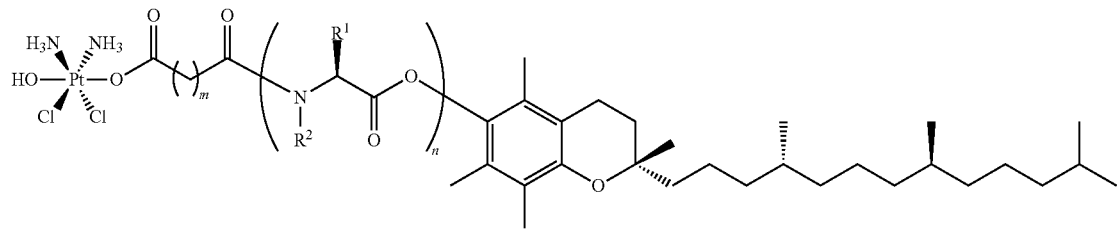

or a pharmaceutically acceptable salt thereof.

In any embodiment herein, it may be that the compound has the formula

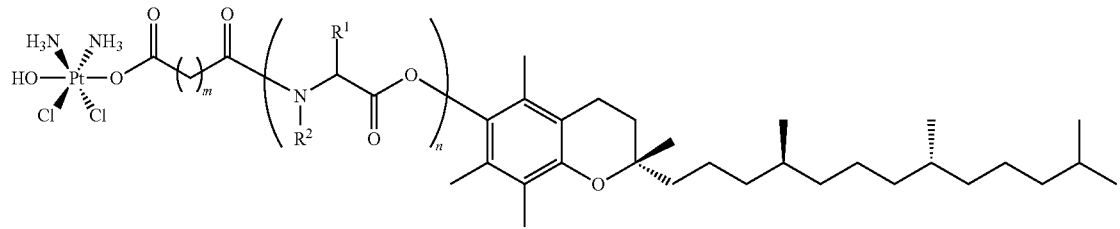

or a pharmaceutically acceptable salt thereof. In any embodiment herein, it may be that the compound has the formula

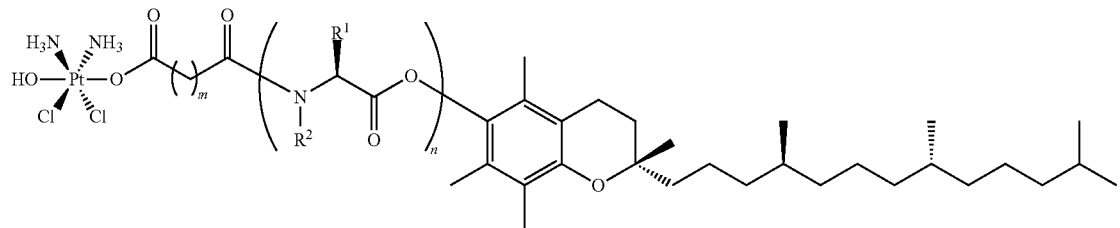

or a pharmaceutically acceptable salt thereof.

In any embodiment herein, it may be that the compound has the formula

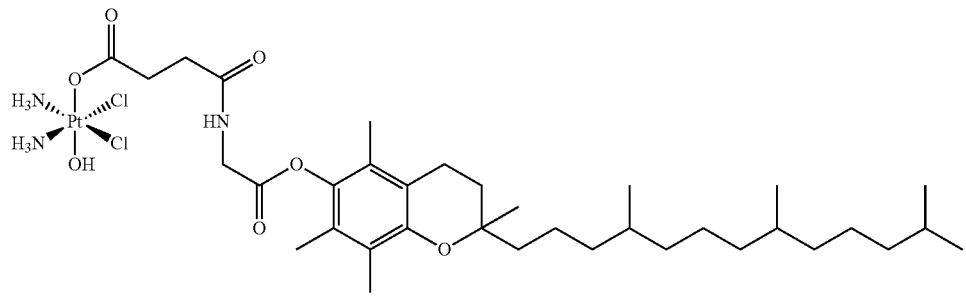

or a pharmaceutically acceptable salt thereof.

In any embodiment herein, it may be that the compound has the formula

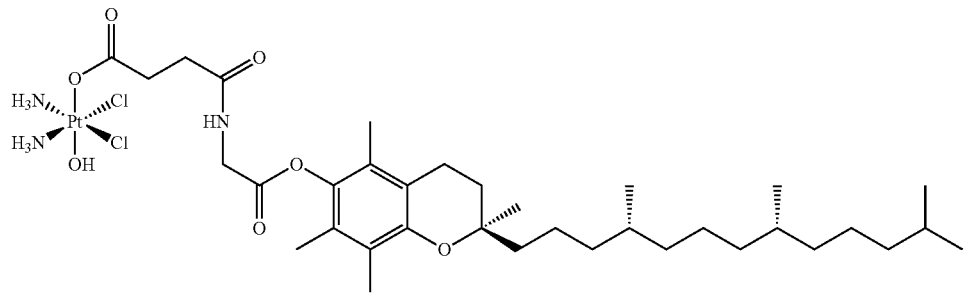

or a pharmaceutically acceptable salt thereof.

In a related aspect, compositions are provided that include a compound of any embodiment disclosed herein and a hyaluronan-tocopherol conjugate. In any embodiment herein, a mass ratio of the compound to the hyaluronan-tocopherol conjugate may be from about 1:15 to about 15:1—thus, the mass ratio may be about 1:15, about 1:14, about 1:13, about 1:12, about 1:11, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, or any range including and/or in between any two of these values. For example, in any embodiment herein it may be that the mass ratio of the compound (of any embodiment herein) to the hyaluronan-tocopherol conjugate is from about 1:10 to about 5:1, from about 1:5 to about 1:1, or from about 1:3 to about 1:1. In any embodiment herein, it may be that the mass ratio of the compound (of any embodiment herein) to the hyaluronan-tocopherol conjugate is about 1:2.

Hyaluronan (also called hyaluronic acid) is an anionic, nonsulfated glycosaminoglycan distributed widely throughout connective, epithelial, and neural tissues. Hyaluronan has the structure:

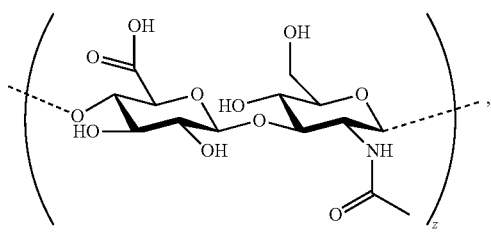

wherein z may be from 1 to 20,000. In any embodiment herein, it may be that the hyaluronan-tocopherol conjugate comprises hyaluronan conjugated to one or more tocopherols by way of one or more of the hyaluronan carboxylate moieties.

Hyaluronan may be isolated from natural sources or synthetically prepared. Isolation of hyaluronan from natural sources is known to those having ordinary skill in the art, for example, as described in Giji, et al., *Adv Food Nutr Res.* 2014; 72:61-77; Ignatova et al., *Pharmaceutical Chemistry Journal* volume 24, pages 211-216 (1990); and Murado, et al., *Food and Bioproducts Processing* Volume 90, Issue 3, July 2012, Pages 491-498; the entire disclosures of which are hereby incorporated by reference. Alternatively, hyaluronan may synthesized as described in Dinkelaar et al., *J. Org. Chem.* 2009, 74, 11, 4208-4216 or Lu et al., *J. Org. Chem.* 2009, 74, 20, 7608-7617; the entire disclosures of which are hereby incorporated by reference.

In any embodiment herein, the hyaluronan of the hyaluronan-tocopherol conjugate may have a weight-average molecular weight (as determined by viscosity, light scattering, gel chromatography, and/or any other suitable method) of about 5,000 to about 2,000,000. Thus, in any embodiment herein, the hyaluronan of the hyaluronan-tocopherol conjugate may have a weight-average molecular weight of about 5,000, about 6,000, about 7,000, about 8,000, about 9,000, about 10,000, about 20,000, about 30,000, about 40,000, about 50,000, about 60,000, about 70,000, about 80,000, about 90,000, about 100,000, about 200,000, about 300,000, about 400,000, about 500,000, about 600,000, about 700,000, about 800,000, about 900,000, about 1,000,000, about 1,500,000, about 2,000,000, or any range including and/or in between any two of these values. For example, in any embodiment herein the hyaluronan of the hyaluronan-tocopherol conjugate may have a weight-average molecular weight of about 5,000 to about 40,000, about 6,000 to about 70,000, about 7,000 to about 150,000, about 8,000 to about 600,000, or about 10,000 to about 2,000,000. One of ordinary skill in the art would understand that particular preparation and measurement methods of a particular hyaluronan may change the weight-average molecular weight, and that the weight-average molecular weight may change as a result of the particular preparation of hyaluronan-tocopherol conjugate and/or preparation of formulations. One of ordinary skill in the art would understand how to account for such changes by suitable modifications of the methods. One of ordinary skill in the art would further understand that a particular hyaluronan may be partially oxidized, partially deacetylated, and/or partially depolymerized.

In any embodiment herein, it may be that the hyaluronan of the hyaluronan-tocopherol conjugate includes hyaluronan that is substituted about 0.1% to about 20% on a molar basis with the tocopherol. Thus, the hyaluronan may be substituted (on a molar basis) with the tocopherol at about 0.1%, about 1%, about 3%, about 4%, about 6%, about 8%, about 10%, about 15%, about 20%, or any range including and/or in between any two of these values. For example, the hyaluronan may be substituted (on a molar basis) with the tocopherol at about 6%.

In any embodiment herein, it may be that the hyaluronan of the hyaluronan-tocopherol conjugate includes hyaluronan that is substituted with the tocopherol at about 0.5 weight % ("wt. %") to about 25 wt. % (based on weight of the hyaluronan moiety in the hyaluronan-tocopherol conjugate)—thus, the hyaluronan may be substituted with the tocopherol at about 0.5 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 15 wt. %, about 20 wt. %, about 25 wt. %, or any range including and/or in between any two of these values. For example, may be substituted with the tocopherol at about 0.5 wt. % to about 5 wt. %, about 1 wt. % to about 10 wt. %, or about 2 wt. % to about 25 wt. %.

In any embodiment herein including a hyaluronan-tocopherol conjugate, it may be that one or more tocopherol is conjugated to hyaluronan by way of the free phenol of the tocopherol. Tocopherols are naturally occurring compounds, which include vitamin E. Food sources with the highest concentrations of vitamin E are vegetable oils, followed by nuts and seeds. Purified tocopherols are available to those having ordinary skill in the art from a variety of commercial sources (Millipore Sigma, BASF). In any embodiment herein including a hyaluronan-tocopherol conjugate, the tocopherol may be a methylated phenol of one or more of the following structures:

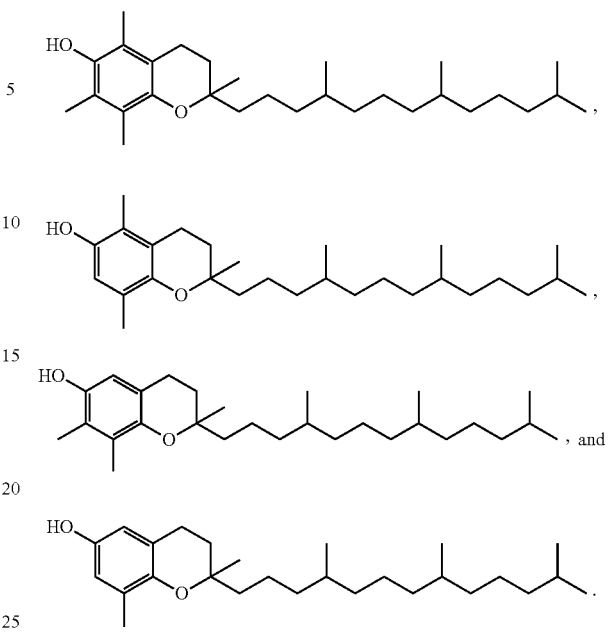

In any embodiment herein, it may be that the hyaluronan-tocopherol conjugate is of Formula II:

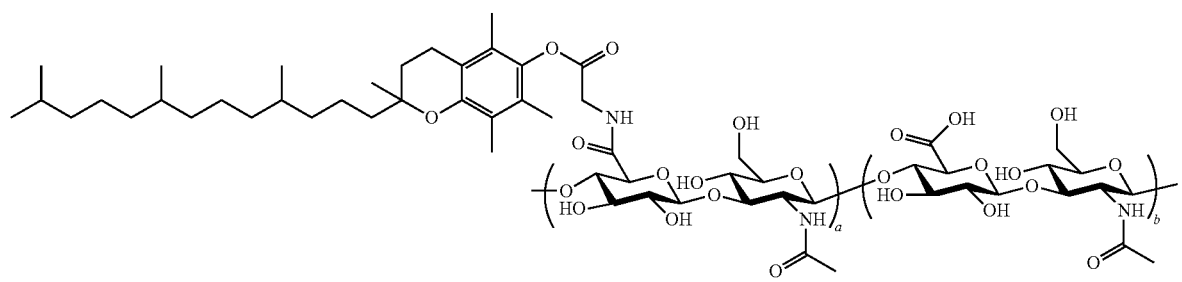

(II)

or a pharmaceutically acceptable salt thereof, wherein a is from 1 to 800 is and b is from 18 to 2540. In any embodiment herein, it may be that the hyaluronan-tocopherol conjugate of Formula II is of Formula IIa:

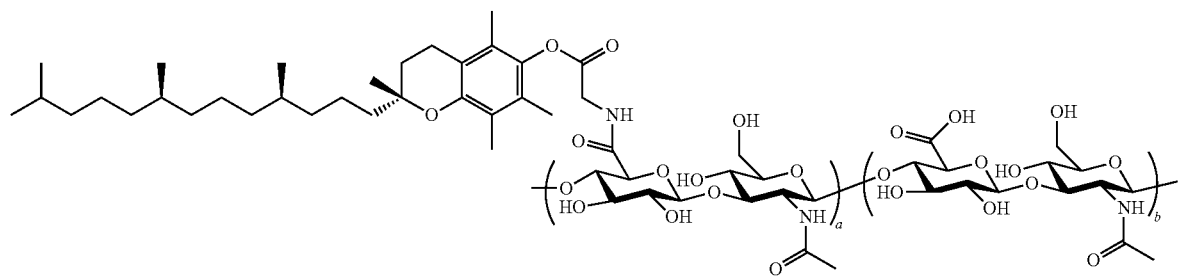

(IIa)

or a pharmaceutically acceptable salt thereof, where a and b are as described for Formula II.

In any embodiment herein, it may be that the hyaluronan-tocopherol conjugate is of Formula III:

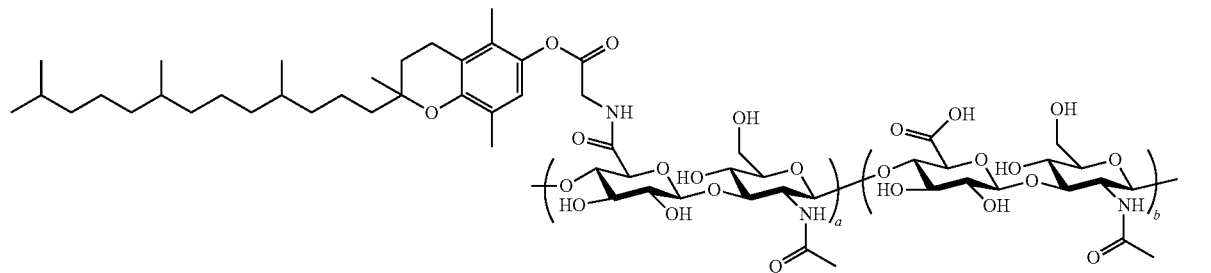

(III)

or a pharmaceutically acceptable salt thereof, wherein a is from 1 to 800 is and b is from 18 to 2540.

In any embodiment herein, it may be that the hyaluronan-tocopherol conjugate is of Formula IV:

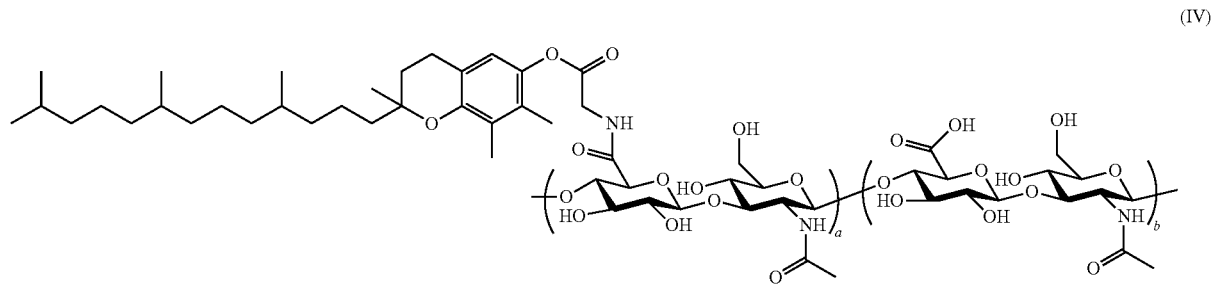

(IV)

or a pharmaceutically acceptable salt thereof, wherein a is from 1 to 800 is and b is from 18 to 2540.

In any embodiment herein, it may be that the hyaluronan-tocopherol conjugate is of Formula V:

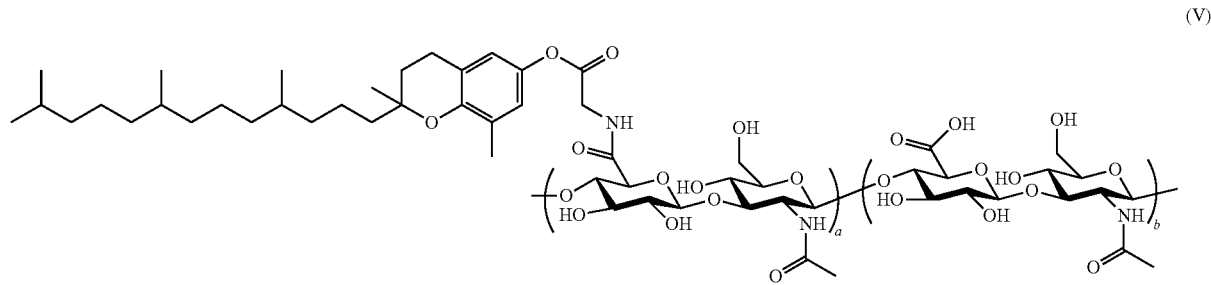

(V)

or a pharmaceutically acceptable salt thereof, wherein a is from 1 to 800 is and b is from 18 to 2540.

In an aspect, a composition is provided that includes a compound of any embodiment disclosed herein, a pharmaceutically acceptable carrier or one or more excipients, fillers or agents (collectively referred to hereafter as "pharmaceutically acceptable carrier" unless otherwise indicated and/or specified), and optionally a hyaluronan-tocopherol conjugate of any embodiment disclosed herein. In a related aspect, a medicament for treating cancer is provided that includes a compound of any embodiment disclosed herein and optionally a hyaluronan-tocopherol conjugate of any embodiment disclosed herein. In a related aspect, a pharmaceutical composition is provided that includes (i) an effective amount of a compound of any embodiment disclosed herein, (ii) a pharmaceutically acceptable carrier, and optionally (iii) a hyaluronan-tocopherol conjugate of any embodiment disclosed herein. For ease of reference, the compositions, medicaments, and pharmaceutical compositions of the present technology may collectively be referred to herein as "compositions." In further related aspects, the present technology provides methods including a compound of formula I of any aspect or embodiment herein, the hyaluronan-tocopherol conjugate of any aspect or embodiment disclosed herein, and/or a composition of any embodiment disclosed herein as well as uses thereof.

"Effective amount" refers to the amount of a compound or composition required to produce a desired effect. One non-limiting example of an effective amount includes amounts or dosages that yield acceptable toxicity and bioavailability levels for therapeutic (pharmaceutical) use including, but not limited to, the reduction of tumor mass. In any aspect or embodiment disclosed herein (collectively referred to herein as "any embodiment herein," "any embodiment disclosed herein," or the like) of the compositions, pharmaceutical compositions, and methods including compounds of the present technology, the effective amount may be an amount effective in treating cancer treating or shrinking a tumor. By way of example, the effective amount of any embodiment herein including a compound of the present technology may be from about 0.01 μg to about 200 mg of the compound (such as from about 0.1 μg to about 50 mg of the compound or about 10 μg to about 20 mg of the compound). The methods and uses according to the present technology may include an effective amount of a compound of any embodiment disclosed herein. In any aspect or embodiment disclosed herein, the effective amount may be determined in relation to a subject.

The pharmaceutical composition of any embodiment disclosed herein may be packaged in unit dosage form. The unit dosage form is effective in treating cancer or is effective in reducing tumor mass. Generally, a unit dosage including a compound of the present technology will vary depending on patient considerations. Such considerations include, for example, age, protocol, condition, sex, extent of disease, contraindications, concomitant therapies and the like. An exemplary unit dosage based on these considerations may also be adjusted or modified by a physician skilled in the art. For example, a unit dosage for a patient comprising a compound of the present technology may vary from $1\times10^{-4}$ g/kg to 1 g/kg, preferably, $1\times10^{-3}$ g/kg to 1.0 g/kg. Dosage of a compound of the present technology may also vary from 0.01 mg/kg to 100 mg/kg or, preferably, from 0.1 mg/kg to 10 mg/kg. Suitable unit dosage forms, include, but are not limited to parenteral solutions, oral solutions, powders, tablets, pills, gelcaps, capsules, lozenges, suppositories, patches, nasal sprays, injectables, implantable sustained-release formulations, mucoadherent films, topical varnishes, lipid complexes, liquids, etc.

The compositions of the present technology may be prepared by mixing one or more compounds of any embodiment disclosed herein, or compositions of the present technology with one or more pharmaceutically acceptable carriers in order to provide a pharmaceutical composition useful to prevent and/or treat cancer or useful in reducing growth or proliferation of a tumor. Such compositions may be in the form of, for example, granules, powders, tablets, capsules, syrup, suppositories, injections, emulsions, elixirs, suspensions or solutions. The instant compositions may be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular injections. The following dosage forms are given by way of example and should not be construed as limiting the present technology.

For oral, buccal, and sublingual administration, powders, suspensions, granules, tablets, pills, capsules, gel caps, and caplets are acceptable as solid dosage forms. These can be prepared, for example, by mixing one or more compounds of the instant present technology with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, enteric coatings, controlled release coatings, binders, thickeners, buffers, sweeteners, flavoring agents, perfuming agents, or a combination of any two or more thereof. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical compositions may be prepared as liquid suspensions or solutions using a sterile liquid, such as, but not limited to, an oil, water, an alcohol, and combinations of these. Pharmaceutically suitable surfactants, stabilizers, antioxidants, suspending agents, emulsifying agents, buffers, pH modifiers, or a combination of any two or more thereof, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as, but not limited to, poly(ethylene glycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Additionally or alternatively, sterile oils may be employed as solvents or suspending agents. Typically, the oil or fatty acid is non-volatile, including natural or synthetic oils, fatty acids, mono-, di- or tri-glycerides.

For injection, the composition may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, buffers, surfactants, bioavailability modifiers, and combinations of any two or more of these.

Compounds of the present technology may be administered to the lungs by inhalation through the nose or mouth. Suitable compositions for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and non-aqueous (e.g., in a fluorocarbon propellant) aerosols may be used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically acceptable carrier and/or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remington's Pharmaceutical Sciences" Mack Pub. Co., New Jersey (1991), and "Handbook of Pharmaceutical Excipients" by Raymond Rowe. Pharmaceutical Press, London, UK (2009), each of which is incorporated herein by reference.

The compositions (e.g., pharmaceutical compositions) of the present technology may be designed to be short-acting, fast-releasing, long-acting, and sustained-releasing as described below. Thus, the compositions may also be formulated for controlled release or for slow release.

The compositions of the present technology may also include, for example, micelles or liposomes, or some other encapsulated form, or may be administered in an extended release form to provide a prolonged storage and/or delivery effect. Therefore, the compositions may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Various assays and model systems, for example those described herein, can be readily employed to determine the therapeutic effectiveness of the treatment according to the present technology.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

Also provided are methods of slowing the proliferation of a cancer cell. In any embodiment herein, it may be that the method comprises contacting the cancer cell with a compound of any embodiment herein or a composition of any embodiment herein. In any embodiment herein, it may be that the contacting is in vitro. In any embodiment herein, it may be that the contacting is in vivo (in a subject).

In an aspect, also provided are methods of slowing or reversing the growth of a tumor in a subject, where the method includes administering to the subject an effective amount of a compound of any embodiment herein or a composition of any embodiment herein.

In an aspect, also provided are methods of treating cancer in a subject, where the method includes administering to the subject an effective amount of a compound of any embodiment herein or a composition of any embodiment herein.

In any embodiment or aspect herein, it may be that the cancer or tumor is selected from squamous cell carcinoma, soft tissue sarcoma, oral melanoma, acute lymphoblastic leukemia (ALL), acute myeloid leukemia (AML), adrenocortical carcinoma, AIDS-related cancers, Kaposi sarcoma (soft tissue sarcoma), AIDS-related lymphoma (lymphoma), anal cancer, appendix cancer, gastrointestinal carcinoid tumors, astrocytomas, atypical teratoid/rhabdoid tumor, basal cell carcinoma of the skin, bile duct cancer, bladder cancer, bone cancer (includes Ewing Sarcoma and Osteosarcoma and Malignant Fibrous Histiocytoma), brain tumors, breast cancer, bronchial tumors (lung cancer), Burkitt lymphoma, carcinoid tumor (gastrointestinal), carcinoma of unknown primary, cardiac (heart) tumors, childhood brain cancer, germ cell tumor, primary CNS lymphoma, cervical cancer, cholangiocarcinoma, chordoma, chronic lymphocytic leukemia (CLL), chronic myelogenous leukemia (CML), chronic myeloproliferative neoplasms, colorectal cancer, craniopharyngioma, cutaneous T-cell lymphoma, ductal carcinoma in situ (DCIS), embryonal tumors, medulloblastoma, endometrial cancer (uterine cancer), ependymoma, esophageal cancer, esthesioneuroblastoma (head and neck cancer), extracranial germ cell tumor, eye cancer, retinoblastoma, fallopian tube cancer, fibrous histiocytoma of bone, osteosarcoma, gallbladder cancer, gastric (stomach) cancer, gastrointestinal stromal tumors (GIST) (soft tissue sarcoma), germ cell tumors, childhood central nervous system germ cell tumors (brain cancer), childhood extracranial germ cell tumors, extragonadal germ cell tumors, ovarian germ cell tumors, testicular cancer, gestational trophoblastic disease, hairy cell leukemia, head and neck cancer, heart tumors, hepatocellular (liver) cancer, histiocytosis, Hodgkin lymphoma, intraocular melanoma, islet cell tumors, pancreatic neuroendocrine tumors, kidney (renal cell) cancer, Langerhans cell histiocytosis, laryngeal cancer (head and neck cancer), leukemia, lip and oral cavity cancer (head and neck cancer), liver cancer, lung cancer, lymphoma, male breast cancer, malignant fibrous histiocytoma of bone and osteosarcoma, melanoma, Merkel cell carcinoma (skin cancer), mesothelioma, metastatic cancer, metastatic squamous neck cancer with occult primary (head and neck cancer), midline tract carcinoma with nut gene changes, mouth cancer (head and neck cancer), multiple endocrine neoplasia syndromes, multiple myeloma/plasma cell neoplasms, mycosis fungoides (lymphoma), myelodysplastic syndromes, myelogenous leukemia, myeloid leukemia, myeloproliferative neoplasms, nasal cavity and paranasal sinus cancer (head and neck cancer), nasopharyngeal cancer (head and neck cancer), neuroblastoma, non-Hodgkin lymphoma, non-small cell lung cancer, oral cancer, osteosarcoma and malignant fibrous histiocytoma of bone, ovarian cancer, pancreatic cancer, pancreatic neuroendocrine tumors (islet cell tumors), papillomatosis (childhood laryngeal), paraganglioma, paranasal sinus and nasal cavity cancer (head and neck cancer), parathyroid cancer, penile cancer, pharyngeal cancer (head and neck cancer), pheochromocytoma, pituitary tumor, plasma cell neoplasm/multiple myeloma, pleuropulmonary blastoma (lung cancer), pregnancy and breast cancer, primary central nervous system (CNS) lymphoma, primary peritoneal cancer, prostate cancer, rectal cancer, recurrent cancer, renal cell (kidney) cancer, rhabdomyosarcoma, salivary gland cancer (head and neck cancer), sarcoma, childhood rhabdomyosarcoma, childhood vascular tumors, Ewing sarcoma (bone cancer), Kaposi sarcoma, osteosarcoma (bone cancer), Sézary syndrome (lymphoma), skin cancer, small cell lung cancer, small intestine cancer, squamous cell carcinoma of the skin, squamous neck cancer with occult primary, metastatic (head and neck cancer), stomach (gastric) cancer, T-cell lymphoma, throat cancer (head and neck cancer), oropharyngeal cancer, hypopharyngeal cancer, thymoma and thymic carcinoma, thyroid cancer, tracheobronchial tumors (lung cancer), transitional cell cancer of the renal pelvis and ureter (kidney (renal cell) cancer), urethral cancer, uterine cancer, uterine sarcoma, vaginal cancer, vascular tumors, vulvar cancer, and Wilms tumor and other childhood kidney tumors.

In any embodiment or aspect herein, it may be that the cancer or tumor is selected from squamous cell carcinoma, soft tissue sarcoma, and oral melanoma. In any embodiment or aspect herein, it may be that the cancer or tumor is squamous cell carcinoma. In any embodiment or aspect herein, it may be that the cancer or tumor is soft tissue sarcoma. In any embodiment or aspect herein, it may be that the cancer or tumor is oral melanoma.

In any embodiment or aspect herein, it may be that administration comprises local administration to a tumor. Local administration may include injection into the tumor or proximal tissues (i.e., intravenous, subcutaneous, intradermal, or intramuscular injection). Proximal tissues may include skin, muscle, blood vessels, or organs and may be located from about 0.0001 to about 20 cm from the tumor. Local administration may also include transdermal administration using, for example, transdermal delivery systems (i.e., a transdermal patch), creams, lotions, ointments, and sprays. In any embodiment or aspect herein, it may be that about 0.5 mg to about 20 mg of a compound of any embodiment herein is administered per $m^2$ of body surface area of the subject ("mg per $m^2$ of body surface area of the subject" is abbreviated in this disclosure as "mg/$n^2$")—thus, the amount administered may be about 0.5 mg/$m^2$, about 1 mg/$m^2$, about 2 mg/$m^2$, about 3 mg/$m^2$, about 4 mg/$m^2$, about 5 mg/$n^2$, about 6 mg/$m^2$, about 7 mg/$m^2$, about 8 mg/$m^2$, about 9 mg/$m^2$, about 10 mg/$m^2$, about 11 mg/$m^2$, about 12 mg/$m^2$, about 13 mg/$m^2$, about 14 mg/$m^2$, about 15 mg/$m^2$, about 16 mg/$m^2$, about 17 mg/$m^2$, about 18 mg/$m^2$, about 19 mg/$m^2$, about 20 mg/$m^2$, or any range including and/or in between any two of these values.

In any embodiment or aspect herein, it may be that administration further comprises the administration of an immunotherapy to the subject. In any embodiment or aspect herein, it may be that the immunotherapy includes an interleukin, for example, IL-2, IL-7, IL-12. In any embodiment or aspect herein, it may be that the immunotherapy includes a cytokine, for example, interferons or G-CSF. In any embodiment or aspect herein, it may be that the immunotherapy comprises a chemokine, for example, CCL3, CCL26, CXCL7. In any embodiment or aspect herein, it may be that the immunotherapy comprises an immunomodulatory imide drug, for example, thalidomide and its analogues (lenalidomide, pomalidomide, and aprenilast). In any embodiment or aspect herein, it may be that the immunotherapy comprises BCG vaccine, rituximab, ofatumumab, elotuzumab, alemtuzumab, durvalumab (Imfinzi), ipilimumab (Yervoy), nivolumab, pembrolizumab a monoclonal antibody, sipuleucel-T, whole tumor lysate, CMV antigen, RNA and tumor associated peptides such as EGFRvIII, GM-CSF expression induction, CAR-T, tisagenlecleucel (Kymriah), veresimod, axicabtagene ciloleucel (Yescarta), or mixtures thereof. In any embodiment or aspect herein, it may be that the immunotherapy comprises veresimod. In any embodiment or aspect herein, it may be that the immunotherapy may be administered concurrently with a compound of the present technology or a compound of the present technology. In any embodiment herein, it may be that the immunotherapy may be administered sequentially with a compound of the present technology or a compound of the present technology.

In any embodiment or aspect herein, it may be that administration further comprises the administration of a chemotherapeutic agent. In any embodiment or aspect herein, it may be that the chemotherapeutic agent is selected from the group consisting of busulfan, cisplatin, carboplatin, oxaliplatin, an octahedral platinum (IV) compound, chlorambucil, cyclophosphamide, ifosfamide, dacarbazine (DTIC), mechlorethamine (nitrogen mustard), melphalan, temozolomide, carmustine (BCNU), lomustine (CCNU), 5-fluorouracil, capecitabine, 6-mercaptopurine, methotrexate, gemcitabine, cytarabine (ara-C), fludarabine, pemetrexed, daunorubicin, doxorubicin (Adriamycin), epirubicin, idarubicin, mitoxantrone, topotecan, irinotecan, etoposide (VP-16), teniposide, paclitaxel, docetaxel, vinblastine, vincristine, vinorelbine, prednisone, dexamethasone, L-asparaginase, dactinomycin, thalidomide, tretinoin, imatinib (Gleevec), gefitinib (Iressa), erlotinib (Tarceva), rituximab (Rituxan), bevacizumab (Avastin), ipilimumab, nivolumab (Opdivo), pembrolizumab (Ketruda), tamoxifen, fulvestrant, anastrozole, exemestane, letrozole, megestrol acetate, bicalutamide, flutamide, leuprolide, goserelin, and a combination of any two or more thereof.

In any aspect or embodiment herein of methods of the present technology, administration may include but not be limited to, parenteral, intravenous, intramuscular, intradermal, intraperitoneal, intratracheal, subcutaneous, oral, intranasal/respiratory (e.g., inhalation), transdermal (topical), sublingual, ocular, vaginal, rectal, or transmucosal administration.

The examples herein are provided to illustrate advantages of the present technology and to further assist a person of ordinary skill in the art with preparing or using the compounds of the present technology or salts, compositions, or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects, or embodiments of the present technology described above. The variations, aspects, or embodiments described above may also further each include or incorporate the variations of any or all other variations, aspects or embodiments of the present technology.

EXAMPLES

Example 1: Synthetic Procedures

Materials and Methods

Cis-Dichlorodiamine platinum (II) (cisplatin) was purchased from Strem Chemicals, Inc. (Newburyport, Mass.).

Sodium hyaluronate was purchased from Contipro a.s. (Dolni Dobrouc, Czech Republic). 1-[Bis(dimethylamino)methylene]-1H-1,2,3-triazolo[4,5-b]pyridinium 3-oxide hexafluorophosphate (HATU), and 3-(3-Dimethylaminopropyl)-1-ethyl-carbodiimide hydrochloride (EDC-HCl) were purchased from Chem-Impex International, Inc. (Wood Dale, Ill.). 1-Hydroxybenzotriazole hydrate (HOBt.H$_2$O) was purchased from Advanced ChemTech (Louisville, Ky.). N-(tert-Butoxycarbonyl)glycine (Boc-Gly-OH), hydrogen peroxide solution (H$_2$O$_2$, 30 wt. % in H$_2$O), succinic anhydride, (±)-α-tocopherol, N,N'-Dicyclohexylcarbodiimide (DCC), N,N-Dimethylpyridin-4-amine (DMAP), trifluoroacetic acid (TFA), N,N-Diisopropylethylamine (DIPEA), tetrabutylammonium hydroxide solution (TBA-OH, 40 wt. % in H$_2$O), and anhydrous organic solvents were purchased from Sigma-Aldrich (Saint Louis, Mo.). Oxaliplatin (Sigma, St. Louis, Mo.) was dissolved in water to 1 mg/mL. All other chemicals and organic solvents were purchased from Thermo Fisher Scientific (Waltham, Mass.).

$^1$H and $^{13}$C NMR spectra were recorded on a Bruker AM 400 spectrometer (operating at 400 and 100 MHz respectively) in either CDCl$_3$ or DMSO-d$_6$ (depending on the particular compound), unless otherwise specified. Chemical shifts are reported in parts per million (ppm) downfield from the chemical shift of TMS (not necessarily included as an internal standard, unless otherwise specified).

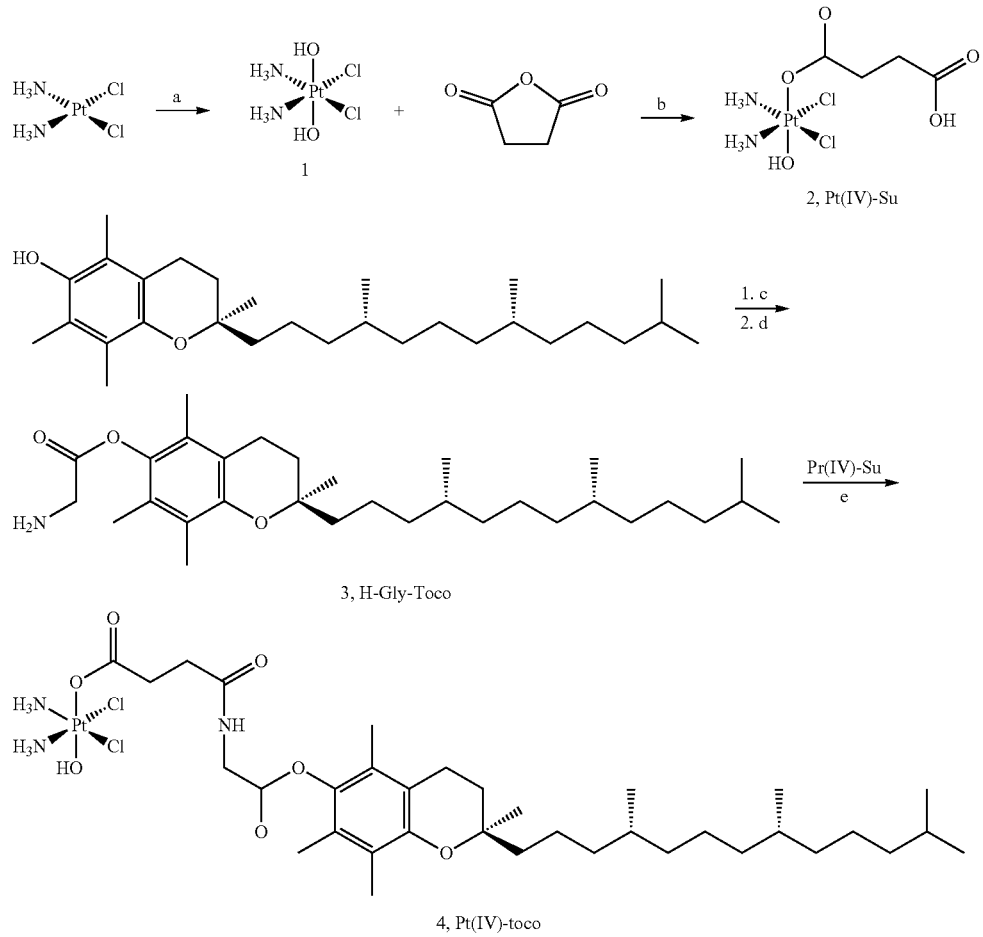

a: water, H$_2$O$_2$, 50° C.;
b: DMSO, 25° C.;
c: Boc-Gly-OH, DCC, DMAP, DCM
d: TFA, DCM; and
e: HATU, DIPEA, DMSO.

Synthesis of Cis,Cis,Trans-[Pt(NH$_3$)$_2$Cl$_2$(OH)$_2$], 1

0.20 mL of H$_2$O$_2$ (30 wt. % in water) was added dropwise to a stirred suspension of cisplatin (1.05 mg) in 3 mL of water (50° C.) in the dark. After 1 hour, a light yellow suspension was obtained and subjected to recrystallization at 4° C. overnight. The product was collected by filtration, washed with ice-cold water, ethanol and diethyl ether, and dried under vacuum. A bright yellow solid was obtained as a product.

Synthesis of Cis,Cis,Trans-[Pt(NH$_3$)$_2$Cl$_2$ (OOCCH$_2$CH$_2$COOH(OH))] (Pt(IV)-Su, 2)

A suspension of compound 1 (200 mg, 0.60 mmol) and succinic anhydride (66 mg, 0.66 mmol) in 16-mL of anhydrous DMSO was stirred in the dark at 25° C. overnight and resulted in a clear light yellowish solution. After DMSO was removed by lyophilization (Labconco 2.5 Plus FreeZone, Kansas City, Mo.), the product was obtained by recrystallization from acetone at −20° C. overnight, and washed with cold acetone and diethyl ether. The solid was dried under vacuum and resulted in a pale yellow product. $^1$H NMR of cis,cis,trans-[Pt(NH$_3$)$_2$Cl$_2$(OOCCH$_2$CH$_2$COOH(OH))], abbreviated as Pt(IV)-Su or 2. $^1$H NMR (400 MHz, DMSO-d$_6$) δ 6.24-5.66 (m, 6H), 2.34-2.45 (m, 4H).

Synthesis of H-Gly-Tocopherol (H-Gly-Toco, 3)

Boc-Gly-OH (0.89 g, 5.11 mmol), (±)-α-tocopherol (2.42 g, 5.62 mmol), and DMAP (64 mg, 0.52 mmol) were dissolved in 20-mL of anhydrous DCM. The mixture was added dropwise to a solution of DCC (1.16 g, 5.62 mmol) in 5-mL of anhydrous DCM, and was stirred at room temperature overnight. The reaction mixture was then stored at −20° C. for 2 hours. After the white precipitate was filtered off, solvent was removed under vacuum to obtain a pale-yellow syrup. The product was purified by a Combiflash Rf+ purification system (Teledyne ISCO, Lincoln, Nebr.), and eluted at 20% of EtOAc in hexane. The fractions containing the product were collected and dried to get a colorless syrup of intermediate "Boc-Gly-Toco." $^1$H NMR (400 MHz, Chloroform-d) δ 5.17 (s, 1H), 4.21 (d, J=5.0 Hz, 2H), 2.59 (t, J=6.8 Hz, 2H), 2.10 (s, 3H), 2.02 (s, 3H), 1.98 (s, 3H), 1.79 (ddq, J=20.0, 13.3, 6.8 Hz, 2H), 1.63-1.49 (m, 3H), 1.49-1.45 (m, 9H), 1.38 (qd, J=8.4, 7.5, 3.0 Hz, 4H), 1.31-1.18 (m, 1 1H), 1.17-1.02 (m, 6H), 0.87 (d, J=6.6 Hz, 6H), 0.85-0.83 (m, 6H); $^{13}$C NMR (101 MHz, CDCl$_3$) δ 169.31, 155.83, 149.78, 140.30, 126.71, 125.00, 123.33, 117.64, 80.24, 75.28, 42.47, 39.52, 37.70, 37.61, 37.56, 37.54, 37.44, 32.93, 32.85, 31.17, 28.46, 28.13, 24.96, 24.59, 22.87, 22.77, 21.17, 20.73, 19.90, 19.83, 13.12, 12.27, 11.96.

A solution of TFA (5 mL) in DCM (5 mL) was added dropwise into a solution of Boc-Gly-Toco (2.87 g, 4.89 mmol) in DCM (15 mL) at 0° C. for 30 min and the reaction mixture was stirred at ambient temperature overnight. The reaction mixture was evaporated to remove solvent and TFA and the gray solid were purified by the Combiflash Rf+ purification system eluting at 100% of EtOAc. The fractions containing the product were collected, yielding H-Gly-Toco as a white solid. $^1$H NMR (400 MHz, DMSO-d$_6$) δ 8.45 (s, 2H), 4.27 (s, 2H), 2.57 (t, J=6.9 Hz, 2H), 2.04 (s, 3H), 1.97 (s, 3H), 1.95 (s, 3H), 1.81-1.72 (m, 2H), 1.56-1.44 (m, 3H), 1.40 (t, J=8.7 Hz, 4H), 1.31-1.16 (m, 11H), 1.16-0.99 (m, 6H), 0.83 (dd, J=9.1, 6.5 Hz, 12H); $^{13}$C NMR (101 MHz, DMSO) δ 166.76, 149.01, 139.57, 126.21, 124.91, 122.07, 117.59, 74.95, 36.73, 36.58, 32.04, 31.93, 27.37, 24.13, 23.69, 22.54, 22.45, 20.31, 19.87, 19.61, 19.55, 12.77, 11.91, 11.56.

Synthesis of Pt(IV)-Su-Gly-Toco (Pt(IV)-toco, 4)

To a mixture of Pt(IV)-Su, 2 (0.54 g, 1.25 mmol), HATU (0.71 g, 1.87 mmol), and DIPEA (0.43 ml, 2.47 mmol) in 30 mL of anhydrous DMSO was added a solution of H-Gly-Toco (0.62 g, 1.28 mmol) in DMSO at room temperature. The reaction mixture was stirred at room temperature overnight. The DMSO solvent was removed by lyophilization and the resulting oily mixture was purified by the Combiflash Rf+ system eluting at 0% to 20% of MeOH in DCM. All of the fractions containing the product were collected. After the removal of solvents, the brown solid was washed with MeOH to furnish a beige-colored solid as the product. $^1$H NMR (400 MHz, DMSO-d$_6$) δ 8.47 (dt, J=16.9, 5.9 Hz, 1H), 6.17-5.62 (m, 6H), 4.14 (t, J=5.0 Hz, 2H), 2.63-2.52 (m, 3H), 2.48-2.35 (m, 4H), 2.02 (s, 3H), 1.93 (s, 3H), 1.91 (s, 3H), 1.76 (t, J=7.7 Hz, 2H), 1.51 (dt, J=13.1, 6.5 Hz, 3H), 1.44-1.34 (m, 4H), 1.32-1.17 (m, 11H), 1.17-1.02 (m, 6H), 0.92-0.80 (m, 12H).

Scheme 2. Exemplary Synthesis of a Hyaluronan-Tocopherol conjugate (HA-toco, 6)

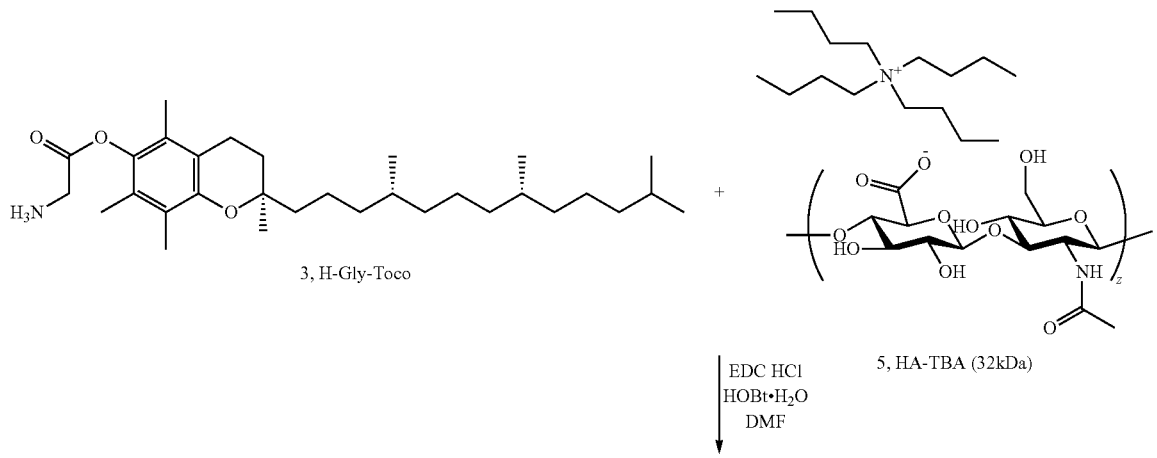

3, H-Gly-Toco

5, HA-TBA (32kDa)

EDC HCl
HOBt·H$_2$O
DMF

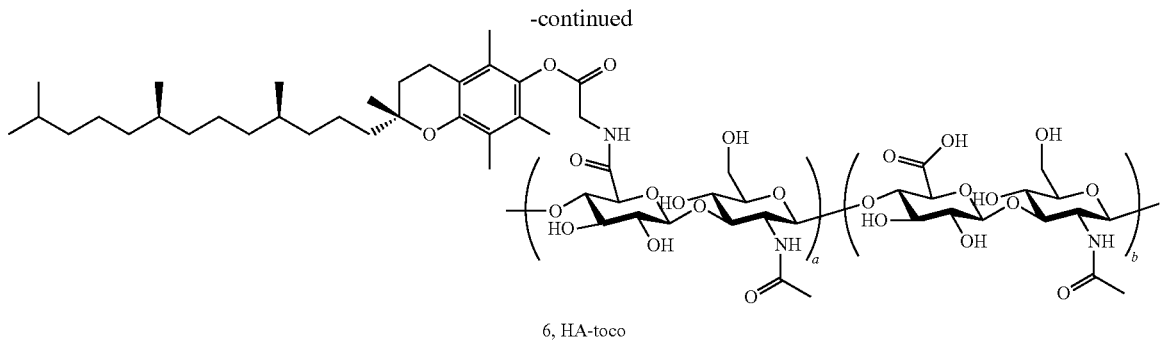

6, HA-toco

Synthesis of HA-TBA, 5

Sodium hyaluronate (32 kDa, 10 g) was dissolved in 200 mL of water, and stirred for 1 hour. The solution was added to 50 g of AG 50W-X8 cation exchange resin (20-50 mesh, H-form, Bio-Rad, Hercules, Calif.), and stirred overnight. The mixture was filtered off to remove resin, and the filtrate was titrated with TBA-OH to pH 8-9. The aqueous solution was lyophilized to obtain a white sponge-like powder and was stored at −20° C. for future uses.

Synthesis and Characterization of HA-Toco, 6

A solution of HA-TBA 5 (200 mg, 0.32 mmol) in 12 mL of DMF was stirred for 30 min at room temperature. A mixture of H-Gly-Toco (15.6 mg, 0.032 mmol), EDC (15.4 mg, 0.08 mmol), and HOBt.$H_2O$ (7.4 mg, 0.048 mmol) in 2.3 mL of DMF was added to the previous solution at room temperature. The reaction mixture was stirred at room temperature overnight. The reaction mixture was dialyzed using dialysis tubing (10,000 MWCO, Thermo scientific) against 50 vol. % EtOH in water overnight, then against NaCl solution (150 mmol, 2 changes in 24 hours), and subsequently against water (3 changes in 2 days). The dialyzed mixture was lyophilized to yield a white cotton-like polymer 6 (117 mg).

The degree of substitution (SD) of tocopherol molecules on HA was calculated based on the result of the $^1$HNMR spectrum. The hydrodynamic diameter of HA-Toco in an aqueous solution was determined using a ZetaPALS (Brookhaven Instrument Corporation, Holtsville, N.Y.). All measurements were carried out with five replicates and the data was analyzed with the build-in software (ZetaPALS).

The degree of substitution (SD) of tocopherol molecules on HA in 6 was calculated to be around 6% on a molar basis by comparing the peak integration ratio of the N-acetyl group of HA (s, 3H, 2.02 ppm) to the methyl groups of tocopherol (m, 12H, 0.81-0.86 ppm) in $^1$HNMR spectrum. The hydrodynamic diameter of HA-Toco in an aqueous solution was determined to be 332.0±2.2 nm with a polydispersity of 0.145±0.028 using the intensity weighted Gaussian distribution. The particle size of HA-Toco nanoparticles was much larger than the non-tocopherol conjugated hyaluronic acid molecules previously evaluated (41). Without being bound by theory, the formation of larger particles may be attributed to the intra- and inter-molecular interactions between the hydrophobic tocopherol pedants, tangling the long and linear HA chains.

Preparation of a HA-Toco/Pt(IV)-Toco Complex

HA-toco (6, 122 mg) was rehydrated in 12 mL of water on a shaker overnight. To the HA-toco solution, a solution of Pt(IV)-toco (4, 61 mg) in 2.4 mL of DMSO was added dropwise and the resulting mixture was stirred for 2 hours in the dark. The solution was lyophilized overnight to remove water and DMSO, then the solid was rehydrated with 5 mL of water for injection (WFI) into a homogenous emulsion. The Pt concentration was determined by an inductively coupled plasma-mass spectrometry (ICP-MS, Agilent Technologies 7500a, Santa Clara, Calif.) using terbium as the internal standard (18). High purity argon (>99.996%) was used as the carrier gas. The final drug concentration was calculated on a cisplatin weight basis.

Example 2: Anti-Proliferation Study

Materials and Methods

AT84 cells were derived from a spontaneous squamous cell carcinoma in the oral mucosa of a C3H mouse (19,20) and were gifted by Aldo Venuti (Regina Elena National Cancer Institute, Rome, Italy). Cells tested negative for interspecies contamination (Idexx BioResearch, CellCheck STR profiling). Cells tested negative for rodent pathogens (Idexx BioResearch, IMPACT I PCR profile). Cells tested negative for Mycoplasm contamination (Lonza, Basel, Switzerland, MycoAlert test kit). Cells were cultured in RPMI-1640 media (Gibco, Thermo Fisher Scientific, Waltham, Mass.) supplemented with 10% FBS (Corning Corning, N.Y.), and 100 U/mL penicillin/100 μg/mL streptomycin (HyClone, Thermo Fisher Scientific, Waltham, Mass.) in a humidified incubator at 37° C. and 5% $CO_2$.

AT84 cells were maintained in RPMI-1640 media (Gibco) with 10% fetal bovine serum (Corning), and 100 U/mL penicillin/100 μg/mL streptomycin (HyClone) in a humidified incubator at 37° C. and 5% $CO_2$. Cells were seeded into 96-well plates (3,000 cells/well in 90 ul media) and allowed to attach overnight. Cisplatin (10 mM stock in water) and Pt(IV)-toco/HA-toco were diluted in water to 10× concentrations. An addition of 10 μl to the cell media and cells resulted in 1× concentrations (8 concentrations in duplicate). After 72 hours at 37° C., Resazurin Blue (Acros Organics, Geel, Belgium) in PBS was added to each well (5 μM final concentration) and incubated at 37° C. for 4 hours. Fluorescence ($\lambda_{ex}$ 550 nm, $\lambda_{em}$ 605 nm) was quantified with a SpectraMax Gemini XS plate-reader (Molecular Devices, Sunnyvale, Calif.). The relative growth of cells incubated with each compound concentration was normalized to vehicle-treated controls (100% proliferation). Data from at least five separate experiments was analyzed using non-linear regression (GraphPad Prism 5.0) to generate $IC_5$a values.

To determine that the Pt(IV)-toco/HA-toco composition exhibits anti-proliferative activity against cancer cells, its effects on the growth of the AT84 murine head and neck squamous cell carcinoma cell line was tested and the results illustrated in FIG. 1. The positive control (cisplatin) and the Pt(IV)-toco/HA-toco composition both inhibited over 80% of cell growth compared to vehicle-treated controls at the highest doses tested with potencies ($IC_{50}$) of 3.0±0.26 μM and 6.1±1.1 μM, respectively. These result support that the Pt(IV)-toco/HA-toco composition of the present technology demonstrated similar growth inhibition against AT84 cells compared to cisplatin, enabling further mechanistic evaluation such as the calreticulin translocation assay discussed below.

Example 3: Calreticulin Translocation

Materials and Methods

Plasmid: The full cDNA sequence of the insert was published by Golden et al. (21) and codes for a mouse calreticulin-HaloTag®-KDEL fusion protein. The cDNA sequence includes Mus musculus calreticulin (Accession BC003453, Version BC003453.1, CDS 37-1286), the HaloTag® vector (Accession HM157289, Version HM157289.1, CDS 197-1081), and a KDEL sequence. This cDNA sequence was inserted into a mammalian expression vector, pD643-Rc, by DNA2.0 (now ATUM, Newark, Calif.). The vector includes a CayenneRFP reporter protein (Ex:554 nm/Em:590 nm) used to visualize positively transfected cells.

AT84 cells were plated in 6-well culture plates and allowed to grow to ~90% confluence. Cells were transfected with a plasmid containing a mouse calreticulin-HaloTag®-KDEL fusion protein and a CayenneRFP reporter protein using lipofectamine (Invitrogen, Carlsbad, Calif.). Five microliters of lipofectamine was added to 150 μl Opti-MEM (Gibco, Thermo Fisher Scientific, Waltham, Mass.). Ten micrograms of plasmid DNA was added to 150 μl Opti-MEM. Both solutions were incubated at room temperature for 5 minutes. DNA solution was added to lipofectamine solution and incubated for 20 minutes at room temperature. During incubation, media on the cells were replaced with serum-free media (2 mL). 250 μl of DNA:lipofectamine solution was added dropwise to each well, which contained 2 mL of serum-free media. After gentle mixing, cells were incubated for 5 hours at 37° C. Cells were split 1:3 into 6-well plates with complete media and incubated overnight at 37° C. Cisplatin, oxaliplatin, or Pt(IV)-toco/HA-toco composition was added to a final concentration of 500 μM. Pt(IV)-toco/HA-toco concentration is based on Pt(IV)-toco content only, not the entire complex. Following 12-15 hours incubation, cells were washed with fresh media. Fresh media was added containing 1 μM HaloTag® Alexa Fluor® 488 Ligand (1 mM solution, Promega, Madison, Wis.) and 20 μM Hoechst dye (20 mM solution, Thermo Scientific, Rockford, Ill.). Cells were incubated at 37° C. for 30 minutes, washed with media, and imaged within one hour. Live cells were imaged using an Olympus IX81 inverted epifluorescence microscope with a 60× objective.

When killed by chemotherapy, cancer cell death can be either immunologic or non-immunologic. Cisplatin causes non-immunogenic cell death, while other chemotherapies, such as oxaliplatin and doxorubicin, cause immunologic cell death (ICD) (42-45). ICD is a particular type of apoptotic cancer cell death that activates the host immune system (43,46) against tumor cells. Some chemotherapeutics elicit ICD by creating endoplasmic reticulum stress, leading to membrane translocation of calreticulin (CRT), an early indicator of ICD, which can be tested in vitro (21,46).

Results

Figure 2:
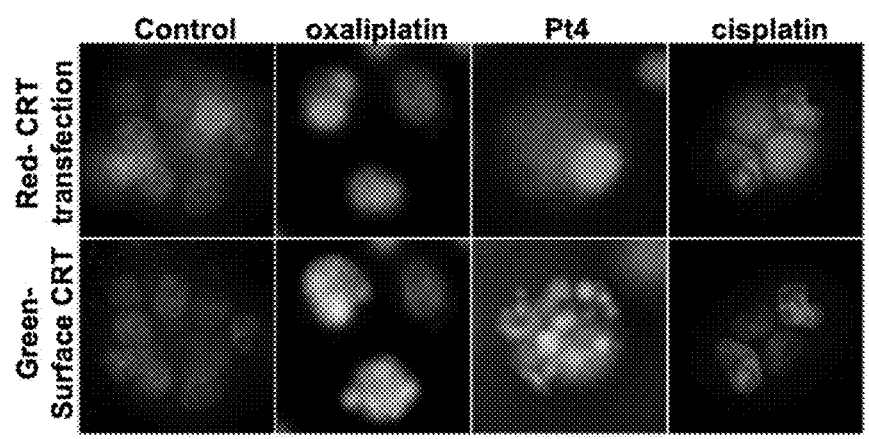
FIG. 2 provides the results of studies evidencing compounds and compositions of the present technology cause calreticulin translocation to the cell surface. AT84 cells were transfected with mouse CRT-HaloTag®-KDEL fusion protein. Positively transfected cells are identified by the CayenneRFP reporter protein expressed from the same plasmid. After incubation with drug (500 uM; 15 hours), membrane translocation of CRT-HaloTag® is visualized by addition of the membrane impermeable HaloTag® Ligand Alexa Fluor® 488. On both, the positive control, oxaliplatin, and Pt(IV)-toco/HA-toco composition show CRT translocation, indicating ICD. In contrast, cisplatin does not show CRT translocation, consistent with its lack of ICD induction.

AT84 cells were transfected with a plasmid coding for mouse CRT-HaloTag®-KDEL fusion protein. Positivity transfected cells can be identified by visualizing the CayenneRFP reporter protein (red), coded for in the same plasmid. Following overnight treatment with an ICD-inducing drug, CRT translocates to the plasma membrane, exposing the HaloTag® protein to the outside of the cell. Extracellularly exposed HaloTag® protein can bind to the membrane impermeable HaloTag® Ligand Alexa Fluor® 488. After overnight treatment with the positive control, oxaliplatin (500 μM) (44), membrane translocation of CRT is observed as green fluorescence (FIG. 2). Similar to oxaliplatin, Pt(IV)-toco/HA-toco composition (500 μM) also causes CRT translocation to the membrane, indicating ICD. In contrast, cisplatin does not cause CRT translocation to the membrane, thus unavailable to bind the 488-labeled ligand, indicating a lack of ICD, consistent with previous reports (47).

Example 4: In Vivo Mouse Studies

The immunological effects induced by certain anticancer chemotherapeutics began to divert the interest of developers of conventional chemotherapies due to their pathways for the activation of the immune system against the cancer. Unlike the traditional chemotherapeutics, which rely on the penetration of nonimmunogenic cytotoxins and sustained exposure, immunogenic chemotherapeutics like oxaliplatin elicit a tumor-specific immune response after inducing a combination of tumor cell stress and death, during which calreticulin translocation, release of ATP and high mobility group protein 1 trigger the activation of dendritic cells that stimulate the presentation of tumor antigens to the cytotoxic $CD8^+$ T lymphocytes to complete the final destruction of tumor cells.

Materials and Methods

All rodent studies were done at the University of Kansas Animal Care Unit, which is in compliance with the "Guide for the Care and Use of Laboratory Animals" and is accredited by the Association for the Assessment and Accreditation of Laboratory Animal Care International (AAALAC). The studies were done according to a protocol approved by the University of Kansas IACUC committee.

Immunocompetent Tumor Model for Efficacy

Wildtype C3H mice (Charles River Strain 025, 6-8 weeks old, 20-25 g) were used for in vivo tumor studies. Both male and female mice were used in the studies. Since no differences were found between the sexes, results combined both sexes into one group. Mice were anesthetized using 5% isoflurane in $O_2$ for 5 minutes. One million AT84 cells in 50 μl PBS were injected subcutaneous (s.c.) into the floor of the mouth via an extra-oral route of C3H mice to obtain orthotopic allograft tumors (19,20). Tumors were palpable by day 4. Under isoflurane anesthesia, Pt(IV)-toco/HA-toco composition (3 mg/kg on Pt(IV)-toco basis) or vehicle (50 μl hyaluronan-tocopherol, 16.7 mg/mL) was injected intratumoral on days 4, 11, and 18 after the tumor cell injection. Tumor size was calculated: tumor volume ($mm^3$)=0.52× $(width)^2$×length, where length is the longer of two perpendicular dimensions.

Immunodeficient Tumor Model for Efficacy

Nude mice (Charles River Ath/nu, 6-8 weeks old, 20-25 g) were used for in vivo tumor studies. Both male and female mice were used in the studies. Since no differences were found between the sexes, results showed both sexes as one group. Mice were anesthetized using 5% isoflurane in $O_2$ for 5 minutes. One million MDA-1986 cells in 50 μl PBS were injected subcutaneous into the left cheek of nude mice to obtain orthotopic xenograft tumors (13,15). Treatment began when tumors reached 75 mm³. Under isoflurane anesthesia, Pt(IV)-toco/HA-toco composition (3 mg/kg on Pt(IV)-toco basis) or vehicle (1.5 MDa hyaluronan, 16.7 mg/mL) was injected intratumoral on days 14, 21, and 28 after the tumor cell injection. Tumor size was calculated using the same equation as stated in the C3H model.

Procedure

To determine whether Pt(IV)-toco 4 inhibits tumor growth in vivo, it was tested in two models of head and neck cancer, one of which involved spontaneously arising oral squamous cell cancer (AT84) in immunocompetent C3H mice, while the other of which used human derived cervical nodal metastasis of tongue cancer (MDA1986) in immunodeficient athymic nude mice.

Results

C3H mice with AT84 allografts and Nude mice with MDA1986 xenografts were administered Pt(IV)-toco/HA-toco composition (3 mg/kg on Pt(IV)-toco basis) intratumorally once per week for 3 weeks, starting when the tumor became measurable in size. These doses were empirically determined as tolerable in these mice, resulting in no decrease in weight or body condition. Ongoing studies in rabbits and pet dogs further confirmed that the Pt(IV)-toco therapy at the proposed dose level did not cause any dose-limiting toxicities such as what would be expected for cisplatin chemotherapy, including renal dysfunction, ototoxicity, and peripheral neuropathy.

Figure 3:
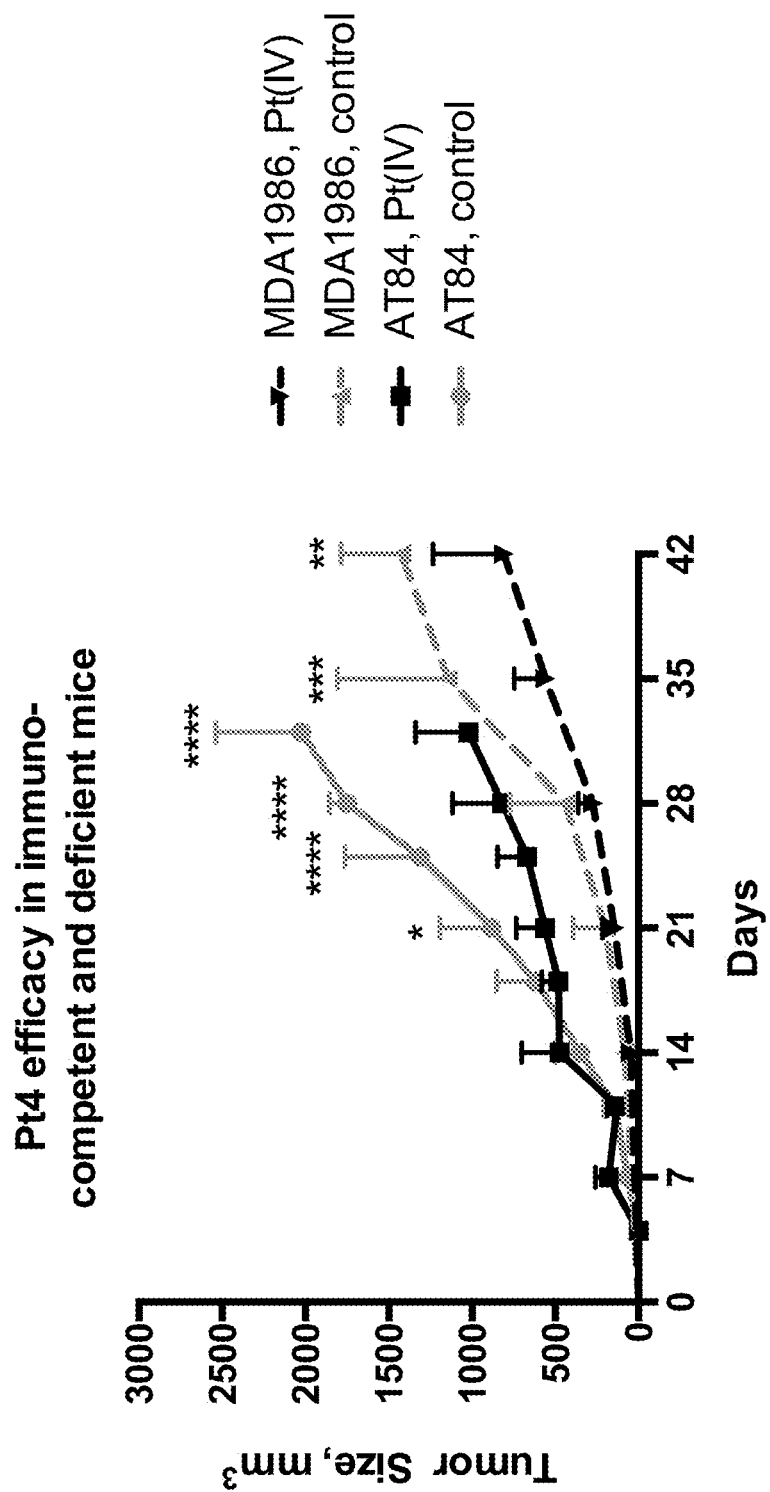
FIG. 3 provides the results of studies evidencing compounds and compositions of the present technology cause growth inhibition of head and neck squamous cell carcinoma in immunocompetent and immunodeficient mice. Statistical significance was achieved between control and Pt(IV)-toco/HA-toco composition treated groups for the last four pairs of measurements of the AT84 allografts in immunocompetent C3H mice (Prism Graphpad, Sidak's multiple comparison test, *p=0.0415, **p<0.0001). Statistical significance was achieved between control and Pt(IV)-toco/HA-toco composition treated groups for the last two pairs of measurements of the MDA-1986 xenografts in immunodeficient nude mice (Prism Graphpad, Sidak's multiple comparison test, *p=0.0005, **p=0.0016).

In both tumor models, Pt(IV)-toco/HA-toco treatments significantly reduced tumor growth over the time course compared to vehicle treated animals in the control groups (FIG. 3). In the AT84 allografts, the mean±SEM for the last pair of measurements of the control and the Pt(IV)-toco treated were 2027±364 mm³ and 1024±129 mm³, respectively, showing 49% tumor inhibition in an immunocompetent host. On the other hand, the mean SEM for the last pair of measurements of the control and the Pt(IV)-toco treated were 1427±162 mm³ and 812±150 mm³, respectively, in the MDA-1986 xenografts, supporting 43% tumor inhibition in an immunodeficient host.

The AT84 model revealed a separated growth pattern between the control and the treated groups much earlier than the MDA-1986 model. Specifically, statistically significant tumor inhibition was observed between day 21 and 32 in the immunocompetent model, lasting about one third of the study course. In contrast, statistically significant tumor inhibition was short-lived in the immunodeficient model, spanning from day 35 to 42, occupying merely 17% of the entire study course. The superior efficacy shown in the AT84 model may be potentially due to the ICD effect induced by the Pt(IV)-toco treatment, which would only manifest in animals with an intact immune system, in which dendritic cells are recruited and T lymphocytes are activated to attack and eradicate some of the residual cancer cells. Thus, the dying cancer cells may act as a vaccine to stimulate tumor-specific immune responses and sustain the effectiveness of the cytotoxic stimulus.

Figure 4A:
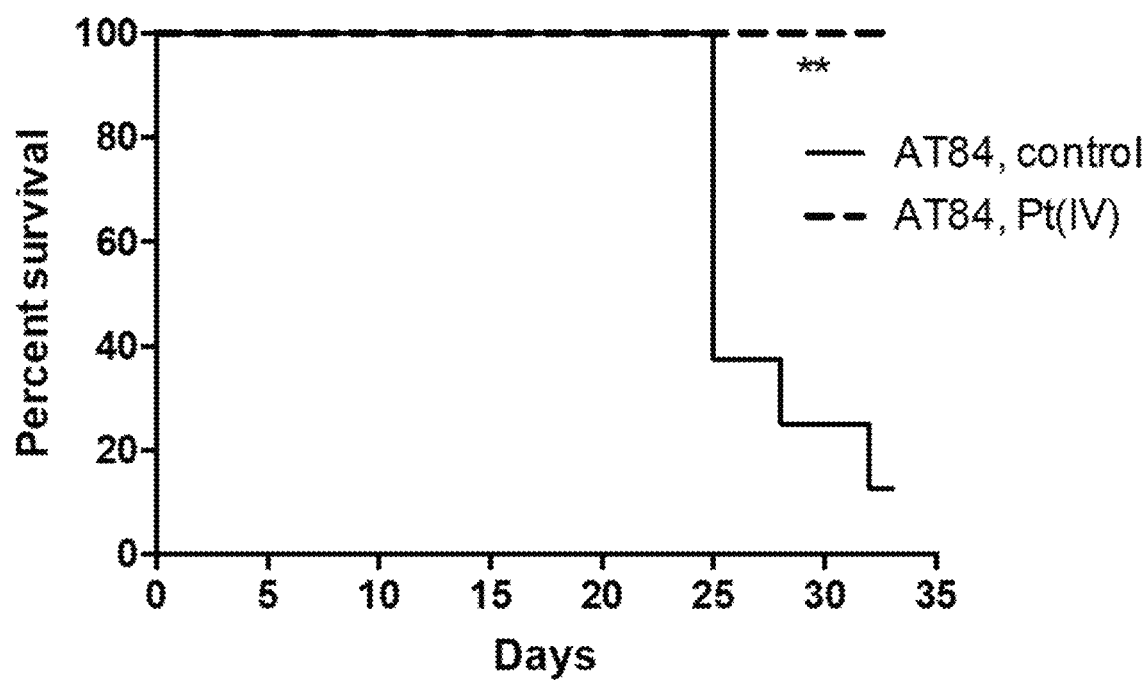
FIGS. 4A-4B provide the results of studies evidencing compounds and compositions of the present technology increase survival rates versus control in tumor models. Survival rates of AT84 (FIG. 4A) and MDA-1986 (FIG. 4B) tumor models. The control and the Pt(IV)-toco/HA-toco composition treated groups differed significantly in both models, indicated by p values of 0.0003 and 0.0015 for the MDA-1986 and the AT84, respectively, calculated using Mantel-Cox statistical analysis (Prism Graphpad).
Figure 4B:
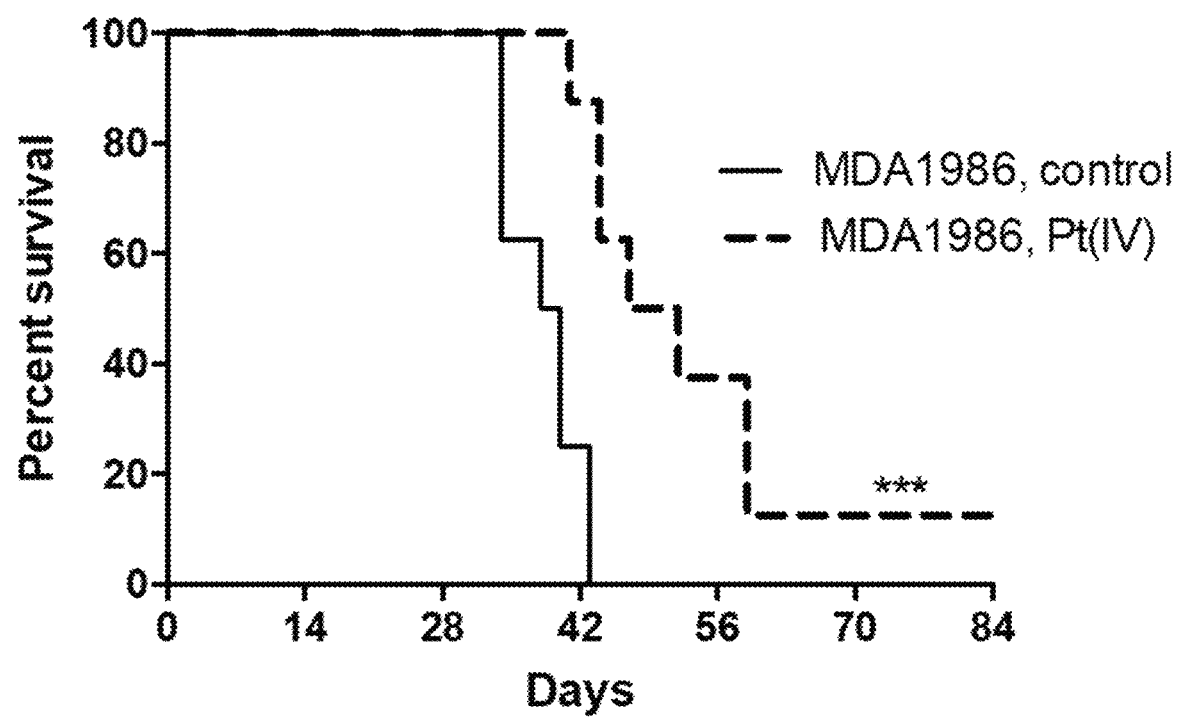

Besides effective tumor inhibition, remarkable statistical significance in survival rates between the control and the treated was achieved using both tumor models (FIGS. 4A-4B). To be noted, the immunocompetent mice treated with Pt(IV)-toco had a survival rate of 100% by the time all control mice have succumbed to the disease, which was not the case in regard to the immunodeficient mice. This difference observed between the two models and the better survival rate of the C3H mice may be partially due to the immunogenic nature of Pt(IV)-toco as aforementioned. The human cancer cell line MDA1986, as opposed to the murine cancer cell line AT84, was selected to establish the tumor models in nude mice because the murine cancer cells could grow aggressively in immunodeficient mice and cause premature casualty.

Example 5: Canine Studies

Study Description

An open-label, compassionate-care clinical trial was conducted in pet dogs with various types of cancer to evaluate the feasibility of intralesional delivery of Pt(IV)-toco/HA-toco composition as chemotherapy. The most common types of cancer include squamous cell carcinoma, soft tissue sarcoma, and oral melanoma. Typical exclusion criteria such as small breeds, large tumor burden, short life expectancy, metastatic disease, and certain pre-existing conditions (e.g., Cushing's disease) were not implemented in this study.

Treatment Protocol

The trial treated 20 dogs with Pt(IV)-toco/HA-toco, and 50 dogs with HylaPlat, a hyaluronic acid and cisplatin nanoconjugate, which has been reported previously in other separate clinical studies (10,12,16,17). The HylaPlat cohort was included in the trial as the internal benchmark test group as the molecule and the formulation have been investigated extensively in preclinical studies (9-11,13,15,22-24).

The reported study was conducted in 18 veterinary hospitals in the Kansas City area. Most pets received either Pt(IV)-toco/HA-toco or HylaPlat treatment at 3-week intervals for up to 10 treatments, ranging from 1 to 17.5 mg/m² on cisplatin basis. Clinical chemistry and hematology were obtained before and after each treatment to evaluate the tolerability of the therapy. A physical exam including measurements of tumor(s) was performed approximately every 3-weeks to monitor the response status of the subjects.

Collection of PBMC for Pt-DNA Adduct Analysis

A blood sample was drawn from all study dogs one hour after the first injection to analyze quantitatively the formation of Pt-DNA adducts in peripheral blood mononuclear cells (PBMC). The analyses were carried out using an Agilent 7500e inductively coupled plasma mass spectrometry (ICP-MS). The analytical method has been validated and published elsewhere (18).

Encouraged by the ICD-inducing and growth inhibiting characteristics of Pt(IV)-toco, and built on the promising results of the mouse tumor models and the absence of dose-limiting toxicities, further development and assessment of Pt(IV)-toco in a large non-laboratory animal species was undertaken. Thus, a pilot clinical study was initiated in pet dogs with various types of naturally occurring cancers under the compassionate-use setting. Canines instead of felines were chosen as the target animal because species-specific hydrothorax, pulmonary and mediastinal edema had been reported in cats treated with cisplatin in the past (48), though other studies have shown that carboplatin may be safe for cats (49-51). The safety of oxaliplatin, which is more analogous to Pt(IV)-toco, has not been reported in a feline clinical study. This example explores whether a suitable Pt(IV)-toco formulation could be developed as a tolerable and efficacious chemotherapeutic agent when administered intralesionally in dogs with different types of injectable tumors.

The pilot canine study did not contain a placebo arm due to the low enrollment rate and the poor compliance. Thus, all study dogs received chemotherapy. Regrettably, requirements of a placebo cohort were infeasible for a proof-of-concept pilot study in dogs, the majority of whom had advanced, metastatic or recurrent cancer, a short life expectancy, and/or inadequate diagnostics which might otherwise render them eligible for other standard-of-care or more established treatment protocols.

Analysis of DNA Platination Using Canine PBMCs

As the original platinum chemotherapy, cisplatin is thought to induce apoptotic cell death via disrupting DNA transcription and recognition by the formation of platinum DNA adducts (43), specifically using the hydrolyzed derivatives of cisplatin, which is the mono-aqua (after the loss of one chloride) and the di-aqua (after the loss of both chlorides). Clinically, the extent of platinum binding to DNA is associated with treatment outcome (52,53). Thus, a cisplatin-releasing formulation can be deemed worthwhile if its DNA platination is not otherwise halted as a result of extensive chemical alterations.

As an example of a cisplatin-based therapy, though other mechanisms of action such as CD44-mediated uptake also play a role, HylaPlat demonstrated the anticipated formation of Pt-DNA adducts in dog PBMCs. The vastly different tumor pathology and micro-environment led to extreme variable levels of Pt-DNA adducts in vivo ranging from non-detectable to 9031.4 fg Pt per µg DNA in a dog with the highest value. Specifically, 6 dogs had no detectable amounts of Pt-DNA in their PBMCs; 9 dogs had less than 100 fg Pt per µg DNA; 15 dogs yielded a level between 100 to 500 fg Pt per µg DNA, and 20 dogs had greater than 500 fg Pt per g DNA. As a result, 40% of the pets in the HylaPlat group demonstrated a Pt-DNA level greater than 500 fg Pt per g DNA. The overall distribution of adduct levels is demonstrated in FIG. 5.

Although belonging to the same platinum-based regimens, oxaliplatin merely induced the formation of approximately one tenth of Pt-DNA adducts relative to cisplatin (54), showing that the anti-proliferative activity of oxaliplatin might be attributed to an alternative mechanism such as ICD. Intrigued by the pronounced discrepancy in the levels of adduct generation between cisplatin and oxaliplatin, Applicant determined the amounts of Pt-DNA adducts in dog PBMCs after the first Pt(IV)-toco/HA-toco treatment and compared the results to their counterparts dosed and sampled in the same manner but treated with HylaPlat instead.

Figure 5:
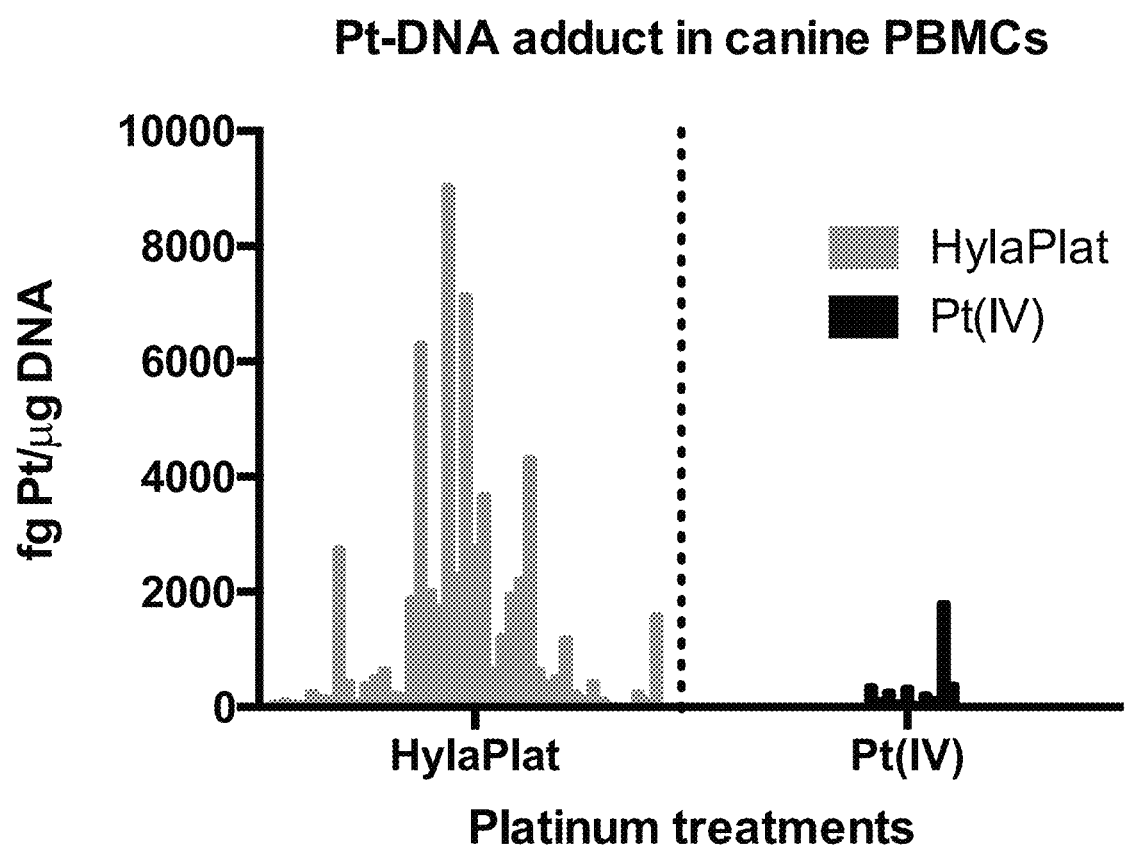
FIG. 5 provides the results of studies evidencing compounds and compositions of the present technology form Pt-DNA adducts. Quantitation of platinum in the form of Pt-DNA adducts in peripheral blood mononuclear cells of pet dogs with spontaneous neoplasias was observed. Study patients were treated with either HylaPlat or Pt(IV)-toco/HA-toco composition. Blood samples were collected 1-hour post treatment. Fifty dogs were treated with HylaPlat, 44 of which yielded quantifiable amounts of platinum. Twenty dogs were treated with Pt(IV)-toco/HA-toco composition, 10 of which exhibited detectable levels of platinum while the remainders of which had no detectable amounts of platinum. Data has been normalized to the equivalent platinum dose (1 mg per $m^2$ of body surface area of the subject) for both groups.

Among the 20 dogs dosed with Pt(IV)-toco/HA-toco, 50% had no detectable amounts of adducts, 10% yielded less than 100 fg Pt per g DNA, 35% rendered greater than 100, but less than 500 fg Pt per g DNA, and merely 5% of the dogs showed a platination level of greater than 500 fg Pt per µg DNA (FIG. 5). In comparison to the 5%, 40% of the dogs treated with HylaPlat at an equivalent dose were measured with greater than 500 fg Pt per g DNA. The result displayed a consistent pattern with the aforementioned difference in the Pt-DNA adduct levels between the cisplatin and oxaliplatin treated calf thymus DNAs, possibly not coincidentally due to the fact that HylaPlat acts as a cisplatin prodrug in a loose sense and Pt(IV)-toco elicits ICD similarly as oxaliplatin.

The statistics of the degrees of DNA platination were analyzed using the Internet version (55) of the Evidence-based Clinical Decision Support Tool and Calculator for Medical Professionals to determine the minimum number of subjects for adequate study power. In two independent study groups, HylaPlat and Pt(IV)-toco/HA-toco, to achieve an anticipated incidence of greater than 500 fg Pt per µg DNA of the PBMCs in 5% of Pt(IV)-toco treated and in 40% of HylaPlat treated patients with an enrollment ratio of 2.5 (number of dogs in each group: HylaPlat=50 and Pt(IV)-toco=20), with a Type I error rate of 0.05 (indicating a 5% probability that a significant difference is actually due to chance and is not a true different), and with a Type II error rate of 80% (indicating a 80% probability that a significant difference is not missed), the minimally required number of participants in the HylaPlat and the Pt(IV)-toco groups are 40 and 16, respectively. This requirement has been met in the pilot study, which contained 50 and 20 patients in the HylaPlat and in the Pt(IV)-toco groups, respectively.

Responders of Intralesional Pt(IV)-Toco/HA-Toco

In the final section of this Example, several interesting case studies demonstrating partial and complete responses to Pt(IV)-toco/HA-toco composition are detailed.

Case 1—Partial Response to Pt(IV)-Toco/HA-Toco in a Recurrent, Non-Resectable, Biologically High Grade Histologically Low Grade Oral Sarcoma The subject was a 5-year old spayed female labrador retriever diagnosed with biologically high grade histologically low grade oral sarcoma. Subject underwent rostral mandibulectomy (partial jaw removal) to remove the majority of the left mandible, followed by finely fractionated radiation therapy. Two years later, the cancer recurred at the previous tumor site. The subject received additional radiation therapy using a less aggressive Superficial Radiation Therapy (STR) protocol and subsequently underwent carboplatin and doxorubicin chemotherapy.

Figure 6A:
FIGS. 6A-6B provides the results of studies evidencing compounds and compositions of the present technology reduce tumor size. A recurrent oral sarcoma received intralesional Pt(IV)-toco/HA-toco composition injections according to the Examples, where
Figure 6B:

After all conventional modalities including sophisticated surgery, two different radiation therapy protocols and two traditional chemotherapies were exhausted, the subject received three consecutive injections of intralesional Pt(IV)-toco/HA-toco at 7.5, 10 and 10 mg/m$^2$ doses on cisplatin basis (i.e., on the basis of the Pt(IV)-toco/HA-toco complex as if it were cisplatin) and demonstrated a partial response to the therapy. The before and after treatment photos are shown in FIGS. 6A-6B, revealing significant tumor reduction.

Figure 7A:
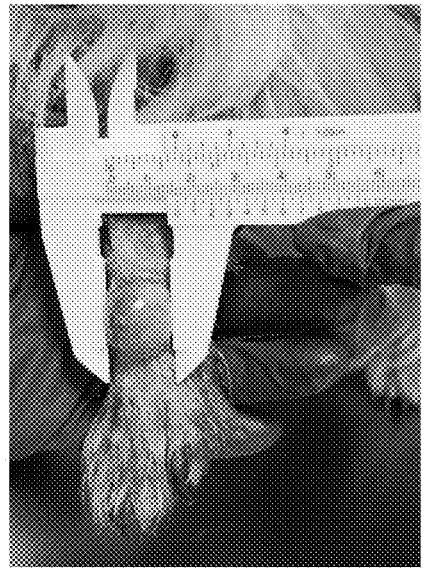
FIGS. 7A-7B provide the results of studies evidencing compounds and compositions of the present technology reduce tumor size. A recurrent extramedullary plasmacytoma received four consecutive intralesional Pt(IV)-toco/HA-toco composition/veresimod co-injections according to the Examples, where
Figure 7B:

Case 2—Complete Response to Pt(IV)-Toco/HA-Toco/Veresimod in a Recurrent, Non-Resectable Extramedullary Plasmacytoma Subject was an Il-year old neutered male yorkshire terrier diagnosed with a recurrent extramedullary plasmacytoma on the left flat foot where a previous tumor was removed surgically two months before the recurrence, along with two metastatic nodules in the left armpit and shoulder. Subject received four consecutive co-injections of intralesional Pt(IV)-toco/HA-toco/veresimod at the doses of 5 to 7.5 mg/m$^2$ on cisplatin basis and 0.34 to 0.68 mg on resiquimod basis. After the fourth injection, the directly treated primary lesion and all the non-treated metastatic nodules went into complete remission (FIGS. 7A-7B).

Figure 8A:
FIGS. 8A-8B provide the results of studies evidencing compounds and compositions of the present technology reduce tumor size. A recurrent oral melanoma received five consecutive intralesional Pt(IV)-toco/HA-toco composition/veresimod co-injections according to the Examples, where
Figure 8B:

Case 3—Complete Response to Pt(IV)-Toco/HA-Toco/Veresimod in a Recurrent, Intermediate Grade Malignancy Oral Melanoma Subject was an 11-year old neutered male schnoodle diagnosed with recurrent oral melanoma after a previous cytoreductive surgery in the mouth lingual to tooth 406 (right lower jaw). Subject received five consecutive intralesional Pt(IV)-toco/veresimod co-injections over three months at the doses of 5 to 12.5 mg/m$^2$ on cisplatin basis and 0.68 to 1.7 mg on resiquimod basis. The lesion went into complete remission after the last injection (FIGS. 8A-8B).

Figure 9A:
FIGS. 9A-9B provide the results of studies evidencing compounds and compositions of the present technology reduce tumor growth. A metastatic oral melanoma received ten consecutive intralesional Pt(IV)-toco/HA-toco composition/veresimod co-injections so far according to the Examples, where
Figure 9B:

Case 4—Durable Partial Response to Pt(IV)-Toco/HA-Toco/Veresimod in a Stage IV (Highest Stage) Oral Melanoma Subject was a 12-year old neutered male Cocker Spaniel diagnosed with an aggressive, malignant palatal melanoma with pulmonary metastases and possible liver nodules. Subject received ten consecutive intralesional Pt(IV)-toco/HA-toco/veresimod co-injections at the doses of 5 to 15 mg/m² on cisplatin basis and 0.34 to 1.7 mg on resiquimod basis over an eight-month period. The primary tumor responded favorably to the therapy and has transformed from a large dome-shaped mass to a flat disc down to the surface of the palate (FIGS. 9A-9B). The only sign of residual tumor is the black (cancerous melanocytes produce black pigment as seen in melanoma) and pink (the normal color of dog palatal tissue is pink) speckled palate. The subject's tumor remained partial remission at approximately 8 months after the first treatment.

REFERENCES

1. Vigneswaran, N., and Williams, M. D. (2014) Epidemiologic trends in head and neck cancer and aids in diagnosis. *Oral Maxillofac Surg Clin North Am* 26, 123-141
2. https://www.cancer.gov/types/head-and-neck/head-neck-fact-sheet. *National Cancer Institute*, Accessed on Apr. 11, 2019
3. Henry, C. J., and Higginbotham, M. L. (2010) *Cancer management in small animal practice*, SAUNDERS ELSEVIER
4. Fessas, P., Lee, H., Ikemizu, S., and Janowitz, T. (2017) A molecular and preclinical comparison of the PD-1-targeted T-cell checkpoint inhibitors nivolumab and pembrolizumab. *Semin Oncol* 44, 136-140
5. Homer, J. J., and Fardy, M. J. (2016) Surgery in head and neck cancer: United Kingdom National Multidisciplinary Guidelines. *J Laryngol Otol* 130, S68-S70
6. Cai, S., Xie, Y., Bagby, T. R., Cohen, M. S., and Forrest, M. L. (2008) Intralymphatic chemotherapy using a hyaluronan-cisplatin conjugate. *J Surg Res* 147, 247-252
7. Cai, S., Xie, Y., Davies, N. M., Cohen, M. S., and Forrest, M. L. (2010) Pharmacokinetics and disposition of a localized lymphatic polymeric hyaluronan conjugate of cisplatin in rodents. *J Pharm Sci* 99, 2664-2671
8. Xie, Y., Aillon, K. L., Cai, S., Christian, J. M., Davies, N. M., Berkland, C. J., and Forrest, M. L. (2010) Pulmonary delivery of cisplatin-hyaluronan conjugates via endotracheal instillation for the treatment of lung cancer. *Int J Pharm* 392, 156-163
9. Zhang, T., Yang, Q., Forrest, W. C., Cai, S., Aires, D., and Forrest, M. L. (2015) A Lanthanum-Tagged Chemotherapeutic Agent HA-Pt to Track the In Vivo Distribution of Hyaluronic Acid Complexes. *BAOJ Pharm Sci* 1
10. Zhang, T., Cai, S., Groer, C., Forrest, W. C., Yang, Q., Mohr, E., Douglas, J., Aires, D., Axiak-Bechtel, S. M., Selting, K. A., Swarz, J. A., Tate, D. J., Bryan, J. N., and Forrest, M. L. (2016) Hyaluronan-Lysine Cisplatin Drug Carrier for Treatment of Localized Cancers: Pharmacokinetics, Tolerability, and Efficacy in Rodents and Canines. *J Pharm Sci* 105, 1891-1900
11. Ishiguro, S., Cai, S., Uppalapati, D., Turner, K., Zhang, T., Forrest, W. C., Forrest, M. L., and Tamura, M. (2016) Intratracheal Administration of Hyaluronan-Cisplatin Conjugate Nanoparticles Significantly Attenuates Lung Cancer Growth in Mice. *Pharm Res* 33, 2517-2529
12. Venable, R. O., Worley, D. R., Gustafson, D. L., Hansen, R. J., Ehrhart, E. J., 3rd, Cai, S., Cohen, M. S., and Forrest, M. L. (2012) Effects of intratumoral administration of a hyaluronan-cisplatin nanoconjugate to five dogs with soft tissue sarcomas. *Am J Vet Res* 73, 1969-1976
13. Cai, S., Xie, Y., Davies, N. M., Cohen, M. S., and Forrest, M. L. (2010) Carrier-based intralymphatic cisplatin chemotherapy for the treatment of metastatic squamous cell carcinoma of the head & neck. *Ther Deliv* 1, 237-245
14. Yang, Q., Cui, H., Cai, S., Yang, X., and Forrest, M. L. (2011) In vivo photoacoustic imaging of chemotherapy-induced apoptosis in squamous cell carcinoma using a near-infrared caspase-9 probe. *J Biomed Opt* 16, 116026
15. Cohen, S. M., Rockefeller, N., Mukerji, R., Durham, D., Forrest, M. L., Cai, S., Cohen, M. S., and Shnayder, Y. (2013) Efficacy and toxicity of peritumoral delivery of nanoconjugated cisplatin in an in vivo murine model of head and neck squamous cell carcinoma. *JAMA Otolaryngol Head Neck Surg* 139, 382-387
16. Cai, S., Zhang, T., Forrest, W. C., Yang, Q., Groer, C., Mohr, E., Aires, D. J., Axiak-Bechtel, S. M., Flesner, B. K., Henry, C. J., Selting, K. A., Tate, D., Swarz, J. A., Bryan, J. N., and Forrest, M. L. (2016) Phase I-II clinical trial of hyaluronan-cisplatin nanoconjugate in dogs with naturally occurring malignant tumors. *Am J Vet Res* 77, 1005-1016
17. Cai, S., Zhang, T., Groer, C., Forrest, M., Aires, D., Otte, V., Barchman, S., Faerber, A., and Forrest, M. L. (2018) Injectable Chemotherapy Downstaged Oral Squamous Cell Carcinoma from Nonresectable to Resectable in a Rescue Dog: Diagnosis, Treatment, and Outcome. *Case Rep Vet Med* 2018, 9078537
18. Zhang, T., Cai, S., Forrest, W. C., Mohr, E., Yang, Q., and Forrest, M. L. (2016) Development and Validation of an Inductively Coupled Plasma Mass Spectrometry (ICP-MS) Method for Quantitative Analysis of Platinum in Plasma, Urine, and Tissues. *Appl Spectrosc* 70, 1529-1536
19. Hier, M. P., Black, M. J., Shenouda, G., Sadeghi, N., and Karp, S. E. (1995) A murine model for the immunotherapy of head and neck squamous cell carcinoma. *Laryngoscope* 105, 1077-1080
20. Paolini, F., Massa, S., Manni, I., Franconi, R., and Venuti, A. (2013) Immunotherapy in new pre-clinical models of HPV-associated oral cancers. *Hum Vaccin Immunother* 9, 534-543
21. Golden, E. B., Frances, D., Pellicciotta, I., Demaria, S., Helen Barcellos-Hoff, M., and Formenti, S. C. (2014) Radiation fosters dose-dependent and chemotherapy-induced immunogenic cell death. *Oncoimmunology* 3, e28518
22. Cohen, M. S., Cai, S., Xie, Y., and Forrest, M. L. (2009) A novel intralymphatic nanocarrier delivery system for cisplatin therapy in breast cancer with improved tumor efficacy and lower systemic toxicity in vivo. *Am J Surg* 198, 781-786
23. Cohen, S. M., Mukerji, R., Cai, S., Damjanov, I., Forrest, M. L., and Cohen, M. S. (2011) Subcutaneous delivery of nanoconjugated doxorubicin and cisplatin for locally advanced breast cancer demonstrates improved efficacy and decreased toxicity at lower doses than standard systemic combination therapy in vivo. *Am J Surg* 202, 646-652; discussion 652-643
24. Yang, Q., Aires, D. J., Cai, S., Fraga, G. R., Zhang, D., Li, C. Z., and Forrest, M. L. (2014) In vivo efficacy of nano hyaluronan-conjugated cisplatin for treatment of murine melanoma. *J Drugs Dermatol* 13, 283-287
25. Zhang, J. Z., Wexselblatt, E., Hambley, T. W., and Gibson, D. (2012) Pt(IV) analogs of oxaliplatin that do not follow the expected correlation between electrochemical reduction potential and rate of reduction by ascorbate. *Chem Commun (Camb)* 48, 847-849

26. Hall, M. D., Amjadi, S., Zhang, M., Beale, P. J., and Hambley, T. W. (2004) The mechanism of action of platinum(IV) complexes in ovarian cancer cell lines. *J Inorg Biochem* 98, 1614-1624
27. Zhang, J. Z., Bonnitcha, P., Wexselblatt, E., Klein, A. V., Najajreh, Y., Gibson, D., and Hambley, T. W. (2013) Facile preparation of mono-, di- and mixed-carboxylato platinum(IV) complexes for versatile anticancer prodrug design. *Chemistry* 19, 1672-1676
28. Wexselblatt, E., Yavin, E., and Gibson, D. (2013) Platinum(IV) prodrugs with haloacetato ligands in the axial positions can undergo hydrolysis under biologically relevant conditions. *Angew Chem Int Ed Engl* 52, 6059-6062
29. Galanski, M., and Keppler, B. K. (1995) Synthesis and Characterization of New Ethylenediamine Platinum(IV) Complexes Containing Lipophilic Carboxylate Ligands. *Met Based Drugs* 2, 57-63
30. Ma, J., Wang, Q., Yang, X., Hao, W., Huang, Z., Zhang, J., Wang, X., and Wang, P. G. (2016) Glycosylated platinum(iv) prodrugs demonstrated significant therapeutic efficacy in cancer cells and minimized side-effects. *Dalton Trans* 45, 11830-11838
31. O'Rourke, T. J., Weiss, G. R., New, P., Burris, H. A., 3rd, Rodriguez, G., Eckhardt, J., Hardy, J., Kuhn, J. G., Fields, S., Clark, G. M., and et al. (1994) Phase I clinical trial of ormaplatin (tetraplatin, NSC 363812). *Anticancer Drugs* 5, 520-526
32. Schilder, R. J., LaCreta, F. P., Perez, R. P., Johnson, S. W., Brennan, J. M., Rogatko, A., Nash, S., McAleer, C., Hamilton, T. C., Roby, D., and et al. (1994) Phase I and pharmacokinetic study of ormaplatin (tetraplatin, NSC 363812) administered on a day 1 and day 8 schedule. *Cancer Res* 54, 709-717
33. van Glabbeke, M., Renard, J., Pinedo, H. M., Cavalli, F., Vermorken, J., Sessa, C., Abele, R., Clavel, M., and Monfardini, S. (1988) Iproplatin and carboplatin induced toxicities: overview of phase II clinical trial conducted by the EORTC Early Clinical Trials Cooperative Group (ECTG). *Eur J Cancer Clin Oncol* 24, 255-262
34. Vermorken, J. B., Gundersen, S., Clavel, M., Smyth, J. F., Dodion, P., Renard, J., and Kaye, S. B. (1993) Randomized phase II trial of iproplatin and carboplatin in advanced breast cancer. The EORTC Early Clinical Trials Group and the EORTC Data Center. *Ann Oncol* 4, 303-306
35. Sternberg, C. N., Whelan, P., Hetherington, J., Paluchowska, B., Slee, P. H., Vekemans, K., Van Erps, P., Theodore, C., Koriakine, O., Oliver, T., Lebwohl, D., Debois, M., Zurlo, A., Collette, L., and Genitourinary Tract Group of the, E. (2005) Phase III trial of satraplatin, an oral platinum plus prednisone vs. prednisone alone in patients with hormone-refractory prostate cancer. *Oncology* 68, 2-9
36. Sternberg, C. N., Petrylak, D. P., Sartor, O., Witjes, J. A., Demkow, T., Ferrero, J. M., Eymard, J. C., Falcon, S., Calabro, F., James, N., Bodrogi, I., Harper, P., Wirth, M., Berry, W., Petrone, M. E., McKearn, T. J., Noursalehi, M., George, M., and Rozencweig, M. (2009) Multinational, double-blind, phase III study of prednisone and either satraplatin or placebo in patients with castrate-refractory prostate cancer progressing after prior chemotherapy: the SPARC trial. *J Clin Oncol* 27, 5431-5438
37. Abu Ammar, A., Raveendran, R., Gibson, D., Nassar, T., and Benita, S. (2016) A Lipophilic Pt(IV) Oxaliplatin Derivative Enhances Antitumor Activity. *J Med Chem* 59, 9035-9046
38. Suntharalingam, K., Song, Y., and Lippard, S. J. (2014) Conjugation of vitamin E analog alpha-TOS to Pt(IV) complexes for dual-targeting anticancer therapy. *Chem Commun (Camb)* 50, 2465-2468
39. He, S., Cong, Y., Zhou, D., Li, J., Xie, Z., Chen, X., Jing, X., and Huang, Y. (2015) A dextran-platinum(IV) conjugate as a reduction-responsive carrier for triggered drug release. *J. Mater. Chem. B* 3, 8203-8211
40. Ling, X., Shen, Y., Sun, R., Zhang, M., Li, C., Mao, J., Xing, J., Sun, C., and Tu, J. (2015) Tumor-targeting delivery of hyaluronic acid-platinum(IV) nanoconjugate to reduce toxicity and improve survival. *Polym Chem* 6, 1541-1552
41. Bagby, T. R., Cai, S., Duan, S., Thati, S., Aires, D. J., and Forrest, L. (2012) Impact of molecular weight on lymphatic drainage of a biopolymer-based imaging agent. *Pharmaceutics* 4, 276-295
42. Casares, N., Pequignot, M. O., Tesniere, A., Ghiringhelli, F., Roux, S., Chaput, N., Schmitt, E., Hamai, A., Hervas-Stubbs, S., Obeid, M., Coutant, F., Metivier, D., Pichard, E., Aucouturier, P., Pierron, G., Garrido, C., Zitvogel, L., and Kroemer, G. (2005) Caspase-dependent immunogenicity of doxorubicin-induced tumor cell death. *J Exp Med* 202, 1691-1701
43. Hato, S. V., Khong, A., de Vries, I. J., and Lesterhuis, W. J. (2014) Molecular pathways: the immunogenic effects of platinum-based chemotherapeutics. *Clin Cancer Res* 20, 2831-2837
44. Kroemer, G., Galluzzi, L., Kepp, O., and Zitvogel, L. (2013) Immunogenic cell death in cancer therapy. *Annu Rev Inmunol* 31, 51-72
45. Pfirschke, C., Engblom, C., Rickelt, S., Cortez-Retamozo, V., Garris, C., Pucci, F., Yamazaki, T., Poirier-Colame, V., Newton, A., Redouane, Y., Lin, Y. J., Wojtkiewicz, G., Iwamoto, Y., Mino-Kenudson, M., Huynh, T. G., Hynes, R. O., Freeman, G. J., Kroemer, G., Zitvogel, L., Weissleder, R., and Pittet, M. J. (2016) Immunogenic Chemotherapy Sensitizes Tumors to Checkpoint Blockade Therapy. *Immunity* 44, 343-354
46. Kepp, O., Senovilla, L., Vitale, I., Vacchelli, E., Adjemian, S., Agostinis, P., Apetoh, L., Aranda, F., Barnaba, V., Bloy, N., Bracci, L., Breckpot, K., Brough, D., Buque, A., Castro, M. G., Cirone, M., Colombo, M. I., Cremer, I., Demaria, S., Dini, L., Eliopoulos, A. G., Faggioni, A., Formenti, S. C., Fucikova, J., Gabriele, L., Gaipl, U. S., Galon, J., Garg, A., Ghiringhelli, F., Giese, N. A., Guo, Z. S., Hemminki, A., Herrmann, M., Hodge, J. W., Holdenrieder, S., Honeychurch, J., Hu, H. M., Huang, X., Illidge, T. M., Kono, K., Korbelik, M., Krysko, D. V., Loi, S., Lowenstein, P. R., Lugli, E., Ma, Y., Madeo, F., Manfredi, A. A., Martins, I., Mavilio, D., Menger, L., Merendino, N., Michaud, M., Mignot, G., Mossman, K. L., Multhoff, G., Oehler, R., Palombo, F., Panaretakis, T., Pol, J., Proietti, E., Ricci, J. E., Riganti, C., Rovere-Querini, P., Rubartelli, A., Sistigu, A., Smyth, M. J., Sonnemann, J., Spisek, R., Stagg, J., Sukkurwala, A. Q., Tartour, E., Thorburn, A., Thorne, S. H., Vandenabeele, P., Velotti, F., Workenhe, S. T., Yang, H., Zong, W. X., Zitvogel, L., Kroemer, G., and Galluzzi, L. (2014) Consensus guidelines for the detection of immunogenic cell death. *Oncoimmunology* 3, e955691
47. Martins, I., Kepp, O., Schlemmer, F., Adjemian, S., Tailler, M., Shen, S., Michaud, M., Menger, L., Gdoura, A., Tajeddine, N., Tesniere, A., Zitvogel, L., and Kroemer, G. (2011) Restoration of the immunogenicity of cisplatin-induced cancer cell death by endoplasmic reticulum stress. *Oncogene* 30, 1147-1158

48. Knapp, D. W., Richardson, R. C., DeNicola, D. B., Long, G. G., and Blevins, W. E. (1987) Cisplatin toxicity in cats. *J Vet Intern Med* 1, 29-35
49. Kisseberth, W. C., Vail, D. M., Yaissle, J., Jeglum, K. A., Couto, C. G., Ward, H., Khanna, C., and Obradovich, J. E. (2008) Phase I clinical evaluation of carboplatin in tumor-bearing cats: a Veterinary Cooperative Oncology Group study. *J Vet Intern Med* 22, 83-88
50. Bailey, D. B., Rassnick, K. M., Dykes, N. L., and Pendyala, L. (2009) Phase I evaluation of carboplatin by use of a dosing strategy based on a targeted area under the platinum concentration-versus-time curve and individual glomerular filtration rate in cats with tumors. *Am J Vet Res* 70, 770-776
51. Fidel, J., Lyons, J., Tripp, C., Houston, R., Wheeler, B., and Ruiz, A. (2011) Treatment of oral squamous cell carcinoma with accelerated radiation therapy and concomitant carboplatin in cats. *J Vet Intern Med* 25, 504-510
52. Hoebers, F. J., Pluim, D., Verheij, M., Balm, A. J., Bartelink, H., Schellens, J. H., and Begg, A. C. (2006) Prediction of treatment outcome by cisplatin-DNA adduct formation in patients with stage III/IV head and neck squamous cell carcinoma, treated by concurrent cisplatin-radiation (RADPLAT). *Int J Cancer* 119, 750-756
53. Welters, M. J., Fichtinger-Schepman, A. M., Baan, R. A., Jacobs-Bergmans, A. J., Kegel, A., van der Vijgh, W. J., and Braakhuis, B. J. (1999) Pharmacodynamics of cisplatin in human head and neck cancer: correlation between platinum content, DNA adduct levels and drug sensitivity in vitro and in vivo. *Br J Cancer* 79, 82-88
54. Saris, C. P., van de Vaart, P. J., Rietbroek, R. C., and Blommaert, F. A. (1996) In vitro formation of DNA adducts by cisplatin, lobaplatin and oxaliplatin in calf thymus DNA in solution and in cultured human cells. *Carcinogenesis* 17, 2763-2769
55. https://clincalc.com/stats/samplesize.aspx. *Clinical Calculator*, Accessed on Apr. 10, 2019

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound of Formula I

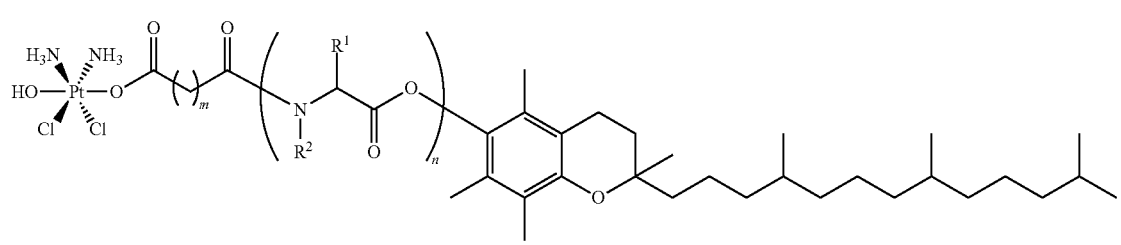

(I)

or a pharmaceutically acceptable salt thereof, wherein independently at each occurrence $R^2$ is H and $R^1$ is H, —CH$_3$, —CH$_2$C(O)NH$_2$, —CH$_2$C(O)OH, —CH$_2$CH$_2$C(O)OH, —CH$_2$CH$_2$C(O)NH$_2$, —CH$_2$SH, —CH$_2$OH, —CH$_2$NH$_2$, —CH(OH)CH$_3$, —CH$_2$CH(CH$_3$)$_2$, —CH$_2$CH$_2$CH$_2$CH$_2$NH$_2$, —CH$_2$CH$_2$SCH$_3$, benzyl, —CH(CH$_3$)CH$_2$CH$_3$, —CH(CH$_3$)$_2$,

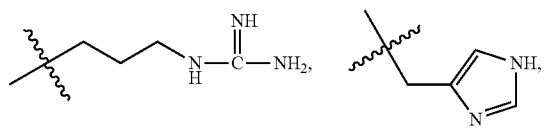

-continued

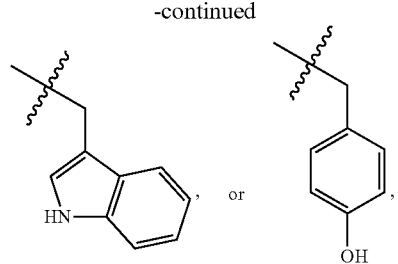

or
$R^1$ and $R^2$ together form —CH$_2$CH$_2$CH$_2$—;
m is 2, 3, 4, 5, 6, 7, or 8; and
n is 1, 2, or 3.

B. The compound of Paragraph A, wherein m is 2.
C. The compound of Paragraph A or Paragraph B, wherein n is 1.
D. The compound of any one of Paragraphs A-C, wherein $R^1$ and $R^2$ are both H.
E. The compound of any one of Paragraphs A-D, wherein the compound has the formula:

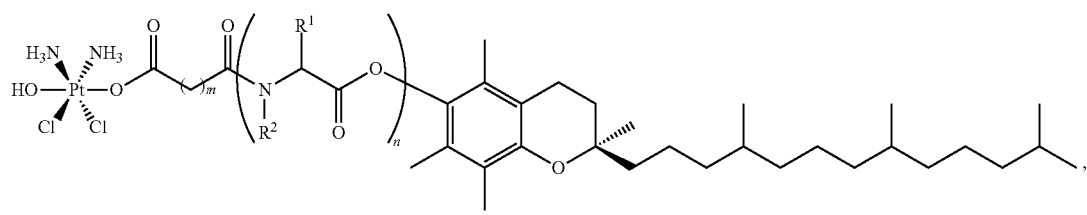

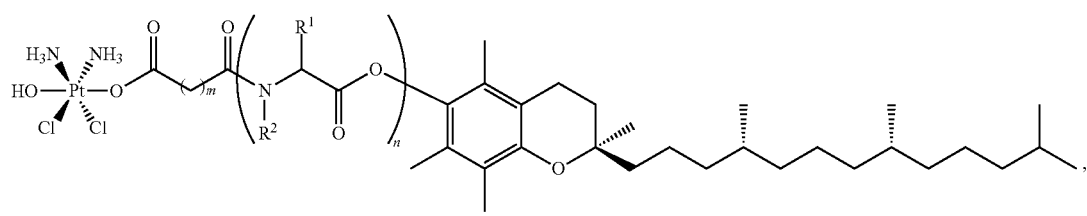

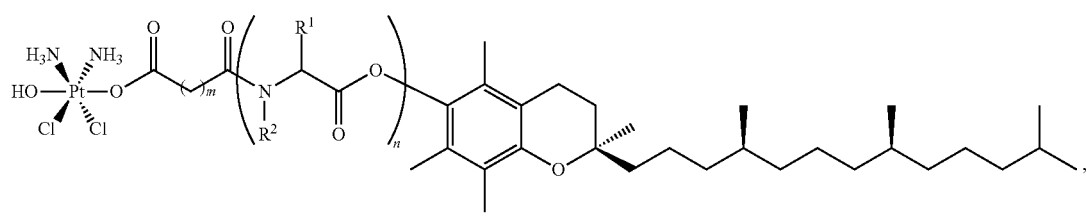

-continued
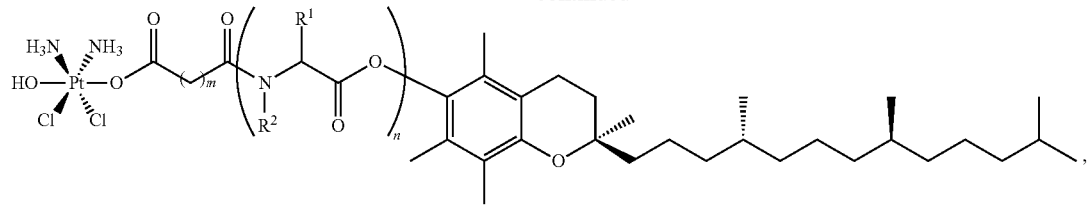
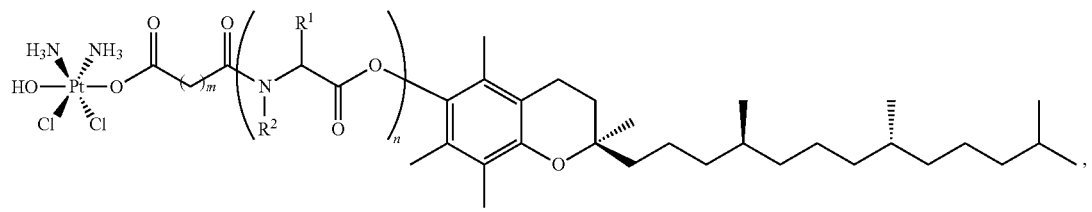
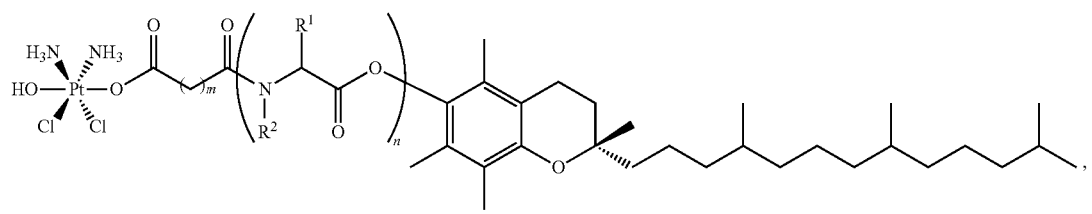
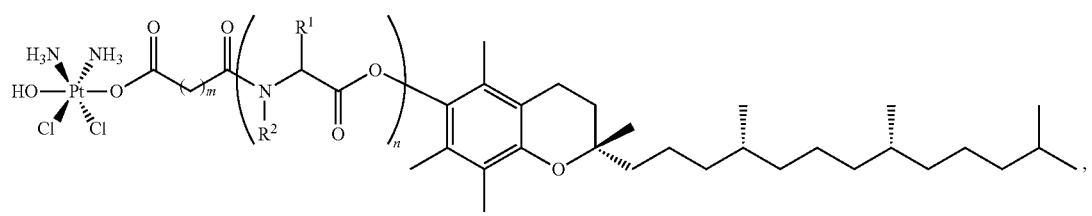
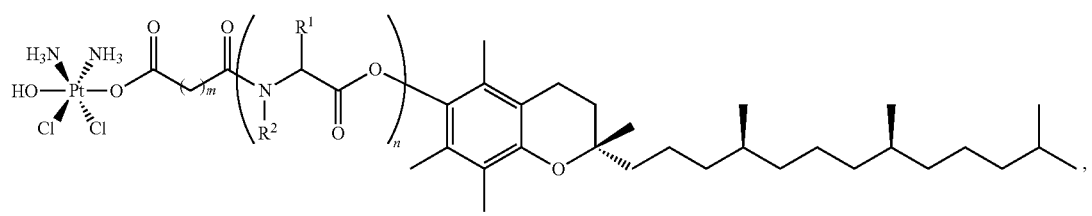
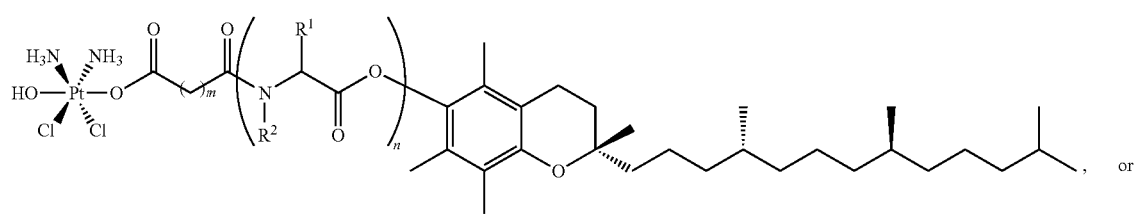, or
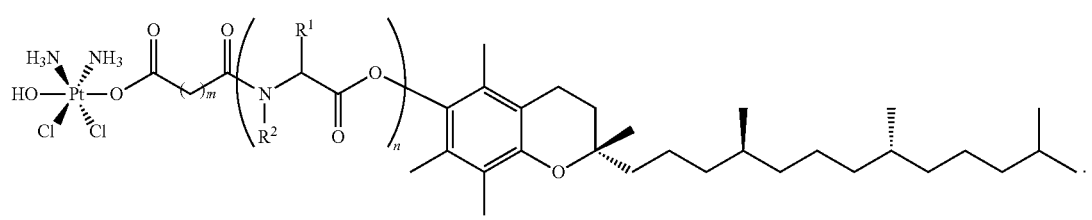

F. The compound of any one of Paragraphs A-E, wherein the compound has the formula

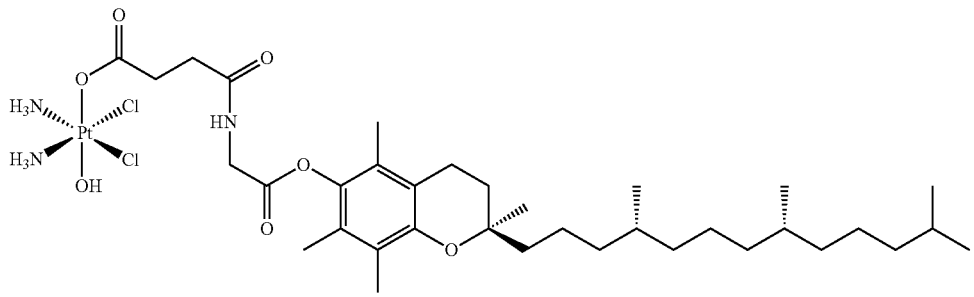

G. A composition comprising the compound of any one of Paragraphs A-F, a pharmaceutically acceptable carrier, and optionally a hyaluronan-tocopherol conjugate.

H. The composition of Paragraph G, wherein the composition comprises an emulsion of the compound and the hyaluronan-tocopherol conjugate.

I. The composition of Paragraph G or Paragraph H, wherein hyaluronan of the hyaluronan-tocopherol conjugate is substituted on a molar basis with about 6% of tocopherol.

J. The composition of any one of Paragraphs G-I, wherein the hyaluronan-tocopherol conjugate is of Formula II, III, IV, V, or a mixture of any two or more thereof:

(II)

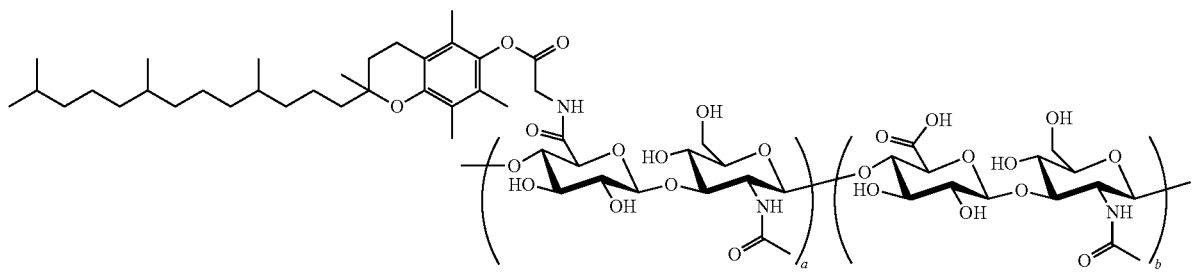

or a pharmaceutically acceptable salt thereof, (III)

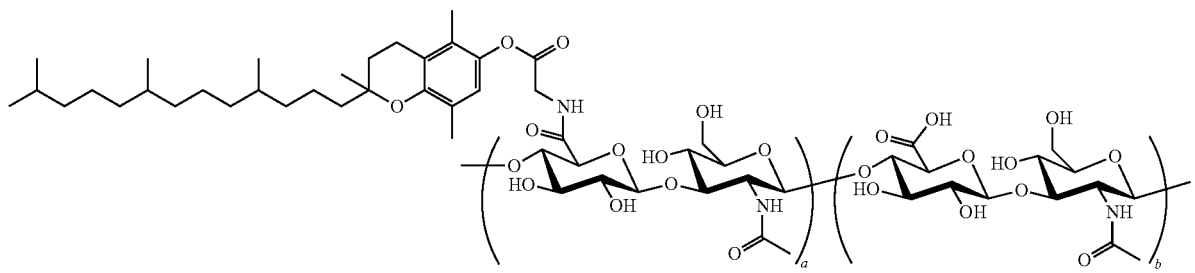

or a pharmaceutically acceptable salt thereof, (IV)

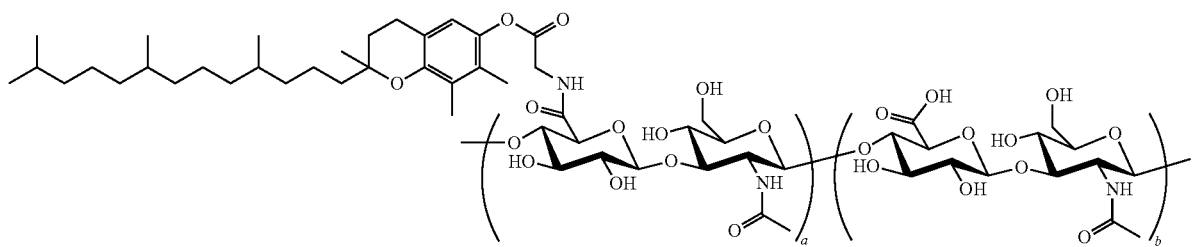

or a pharmaceutically acceptable salt thereof,

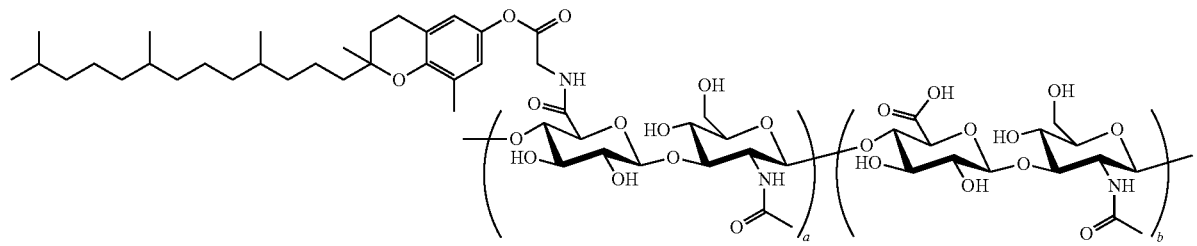

(V)

or a pharmaceutically acceptable salt thereof,
wherein a is independently at each occurrence from 1 to 800 and b is independently at each occurrence from 18 to 2540.

K. The composition of Paragraph J, wherein the hyaluronan-tocopherol conjugate is of Formula IIa:

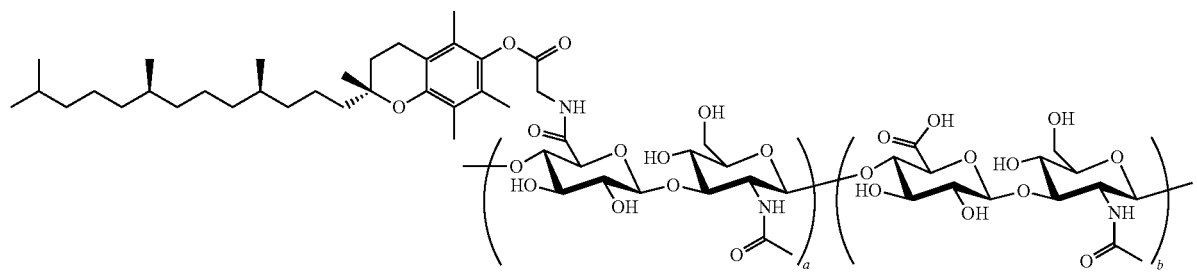

(IIa)

or a pharmaceutically acceptable salt thereof.

L. The composition of any one of Paragraphs G-K, wherein the composition comprises an effective amount of the compound for treating a cancer, a tumor, or both.

M. A method of slowing proliferation of a cancer cell, the method comprising contacting the cancer cell with a compound of any one Paragraphs A-F or a composition of any one of Paragraphs G-L.

N. The method of Paragraph M, wherein the contacting is in vitro.

O. The method of Paragraph M, wherein the contacting is in vivo in a subject.

P. The method of any one of Paragraphs M-O, wherein the method comprises contacting the cancer cell with an effective amount of the compound for slowing proliferation of the cancer cell.

Q. A method of slowing or reversing growth of a tumor in a subject, the method comprising administering to the subject an effective amount of a compound of any one Paragraphs A-F or a composition of any one of Paragraphs G-L.

R. A method of treating cancer in a subject, the method comprising administering to the subject an effective amount of a compound of any one Paragraphs A-F or a composition of any one of Paragraphs G-L.

S. The method of any one of Paragraphs M-P, the method of Paragraph Q, or the method of Paragraph R, wherein the cancer cell, tumor, or cancer is selected from squamous cell carcinoma, soft tissue sarcoma, oral melanoma, acute lymphoblastic leukemia (ALL), acute myeloid leukemia (AML), adrenocortical carcinoma, AIDS-related cancers, Kaposi sarcoma (soft tissue sarcoma), AIDS-related lymphoma (lymphoma), anal cancer, appendix cancer, gastrointestinal carcinoid tumors, astrocytomas, atypical teratoid/rhabdoid tumor, basal cell carcinoma of the skin, bile duct cancer, bladder cancer, bone cancer (includes Ewing Sarcoma and Osteosarcoma and Malignant Fibrous Histiocytoma), brain tumors, breast cancer, bronchial tumors (lung cancer), Burkitt lymphoma, carcinoid tumor (gastrointestinal), carcinoma of unknown primary, cardiac (heart) tumors, childhood brain cancer, germ cell tumor, primary CNS lymphoma, cervical cancer, cholangiocarcinoma, chordoma, chronic lymphocytic leukemia (CLL), chronic myelogenous leukemia (CML), chronic myeloproliferative neoplasms, colorectal cancer, craniopharyngioma, cutaneous T-cell lymphoma, ductal carcinoma in situ (DCIS), embryonal tumors, medulloblastoma, endometrial cancer (uterine cancer), ependymoma, esophageal cancer, esthesioneuroblastoma (head and neck cancer), extracranial germ cell tumor, eye cancer, retinoblastoma, fallopian tube cancer, fibrous histiocytoma of bone, osteosarcoma, gallbladder cancer, gastric (stomach) cancer, gastrointestinal stromal tumors (GIST) (soft tissue sarcoma), germ cell tumors, childhood central nervous system germ cell tumors (brain cancer), childhood extracranial germ cell tumors, extragonadal germ cell tumors, ovarian germ cell tumors, testicular cancer, gestational trophoblastic disease, hairy cell leukemia, head and neck cancer, heart tumors, hepatocellular (liver) cancer, histiocytosis, Hodgkin lymphoma, intraocular melanoma, islet cell tumors, pancreatic neuroendocrine tumors, kidney (renal cell) cancer, Langerhans cell histiocytosis, laryngeal cancer (head and neck cancer), leukemia, lip and oral cavity cancer (head and neck cancer), liver cancer, lung cancer, lymphoma, male breast cancer, malignant fibrous histiocytoma of bone and osteosarcoma, melanoma, Merkel cell carcinoma (skin cancer), mesothelioma, metastatic cancer, metastatic squamous neck cancer with occult primary (head and neck cancer), midline tract carcinoma with nut gene changes, mouth cancer (head and neck cancer), multiple endocrine neoplasia syndromes, multiple myeloma/plasma cell neoplasms, mycosis fungoides (lymphoma), myelodysplastic syndromes, myelogenous leukemia, myeloid leukemia, myeloproliferative neoplasms, nasal cavity and paranasal sinus cancer (head and neck cancer), nasopharyngeal cancer (head and neck cancer), neuroblastoma, non-Hodgkin lymphoma, non-small cell lung cancer, oral cancer, osteosarcoma and malignant fibrous histiocytoma of bone, ovarian cancer, pancreatic cancer, pancreatic neuroendocrine tumors (islet cell tumors), papillomatosis (childhood laryngeal), paraganglioma, paranasal sinus and nasal cavity cancer (head and neck cancer), parathyroid cancer, penile cancer, pharyngeal cancer (head and neck cancer), pheochromocytoma, pituitary tumor, plasma cell neoplasm/multiple myeloma, pleuropulmonary blastoma (lung cancer), pregnancy and breast cancer, primary central nervous system (CNS) lymphoma, primary peritoneal cancer, prostate cancer, rectal cancer, recurrent cancer, renal cell (kidney) cancer, rhabdomyosarcoma, salivary gland cancer (head and neck cancer), sarcoma, childhood rhabdomyosarcoma, childhood vascular tumors, Ewing sarcoma (bone cancer), Kaposi sarcoma, osteosarcoma (bone cancer), Sézary syndrome (lymphoma), skin cancer, small cell lung cancer, small intestine cancer, squamous cell carcinoma of the skin, squamous neck cancer with occult primary, metastatic (head and neck cancer), stomach (gastric) cancer, T-cell lymphoma, throat cancer (head and neck cancer), oropharyngeal cancer, hypopharyngeal cancer, thymoma and thymic carcinoma, thyroid cancer, tracheobronchial tumors (lung cancer), transitional cell cancer of the renal pelvis and ureter (kidney (renal cell) cancer), urethral cancer, uterine cancer, uterine sarcoma, vaginal cancer, vascular tumors, vulvar cancer, and Wilms tumor and other childhood kidney tumors.

T. The method of any one of Paragraphs M-P, the method of Paragraph Q, or the method of Paragraph R, wherein the cancer cell, tumor, or cancer is selected from squamous cell carcinoma, soft tissue sarcoma, and oral melanoma.

U. The method of any one of Paragraphs Q-T, wherein the administering comprises local administration to a tumor.

V. The method of Paragraph U, wherein the administering comprises about 1 mg to about 20 mg of the compound administered per m² of body surface area of the subject.

W. The method of any one of Paragraphs Q-V, wherein the administering comprises oral, rectal, nasal, vaginal, transdermal, intravenous, intramuscular, or inhalation administration.

X. The method of any one of Paragraphs Q-W, wherein the administering comprises injection of the compound of formula I, or the composition into the tumor or proximal to the tumor.

Y. The method of any one of Paragraphs Q-X, wherein the administering further comprises the administration of an immunotherapy to the subject.

Z. The method of Paragraph Y, wherein the immunotherapy comprises veresimod.

AA. The method of Paragraph Y or Paragraph Z, wherein the immunotherapy is administered concurrently with the compound or with the composition.

AB. The method of Paragraph Y or Paragraph Z, wherein the immunotherapy is administered sequentially with the compound or with the composition.

AC. The method of any one of Paragraphs Q-AB, wherein the administering further comprises administration of a chemotherapeutic agent selected from the group consisting of an alkylating agent; a nitrosourea; an antimetabolite; an anthracycline; a topoisomerase II inhibitor; a mitotic inhibitor; an anti-estrogen; a progestin; an aromatase inhibitor; an anti-androgen; an LHRH agonist; a corticosteroid hormone; a DNA alkylating agent; a taxane; a vinca alkaloid; a microtubule poison, and a combination thereof, to the subject.

AD. The method of any one of Paragraphs Q-AC, wherein the administering further comprises administration of a chemotherapeutic agent selected from the group consisting of busulfan, cisplatin, carboplatin, oxaliplatin, an octahedral platinum (IV) compound, chlorambucil, cyclophosphamide, ifosfamide, dacarbazine (DTIC), mechlorethamine (nitrogen mustard), melphalan, temozolomide, carmustine (BCNU), lomustine (CCNU), 5-fluorouracil, capecitabine, 6-mercaptopurine, methotrexate, gemcitabine, cytarabine (ara-C), fludarabine, pemetrexed, daunorubicin, doxorubicin (Adriamycin), epirubicin, idarubicin, mitoxantrone, topotecan, irinotecan, etoposide (VP-16), teniposide, paclitaxel, docetaxel, vinblastine, vincristine, vinorelbine, prednisone, dexamethasone, L-asparaginase, dactinomycin, thalidomide, tretinoin, imatinib (Gleevec), gefitinib (Iressa), erlotinib (Tarceva), rituximab (Rituxan), bevacizumab (Avastin), ipilimumab, nivolumab (Opdivo), pembrolizumab (Ketruda), tamoxifen, fulvestrant, anastrozole, exemestane, letrozole, megestrol acetate, bicalutamide, flutamide, leuprolide, goserelin, and a combination of any two or more thereof.

AE. The method of any one of Paragraphs Q-AD, wherein the administering further comprises administration of cisplatin.

AF. The method of any one of Paragraphs Q-AE, wherein the subject is a mammal, bird, or reptile.

AG. The method of any one of Paragraphs Q-AF, wherein the subject is a human.

Other embodiments are set forth in the following claims.

What is claimed is:

1. A compound of Formula I

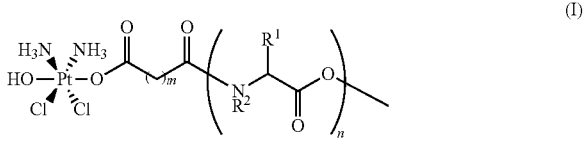

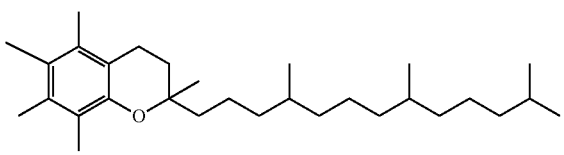

or a pharmaceutically acceptable salt thereof, wherein independently at each occurrence $R^2$ is H and $R^1$ is H, —CH$_3$, —CH$_2$C(O)NH$_2$, —CH$_2$C(O)OH, —CH$_2$CH$_2$C(O)OH, —CH$_2$CH$_2$C(O)NH$_2$, —CH$_2$SH, —CH$_2$OH, —CH$_2$NH$_2$, —CH(OH)CH$_3$, —CH$_2$CH(CH$_3$)$_2$, —CH$_2$CH$_2$CH$_2$CH$_2$NH$_2$, —CH$_2$CH$_2$SCH$_3$, benzyl, —CH(CH$_3$)CH$_2$CH$_3$, —CH(CH$_3$)$_2$,

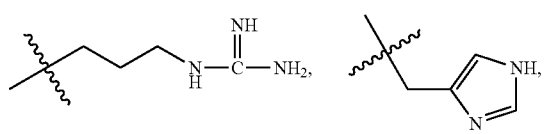

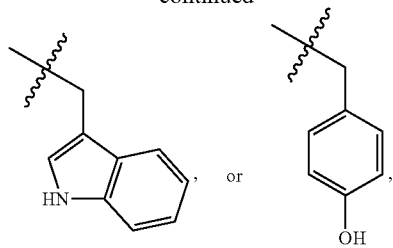

or
$R^1$ and $R^2$ together form —CH$_2$CH$_2$CH$_2$—;
m is 2, 3, 4, 5, 6, 7, or 8; and
n is 1, 2, or 3.

2. The compound of claim 1, wherein m is 2.

3. The compound of claim 1, wherein n is 1.

4. The compound of claim 1, wherein $R^1$ and $R^2$ are both H.

5. The compound of claim 1, wherein the compound of Formula I is of the formula

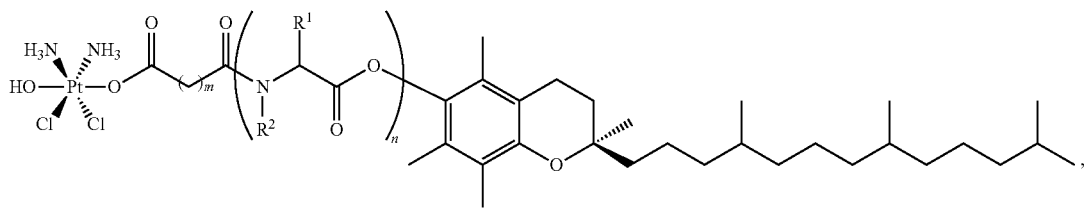

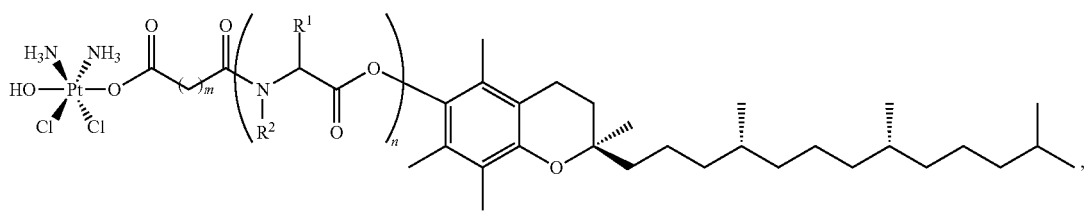

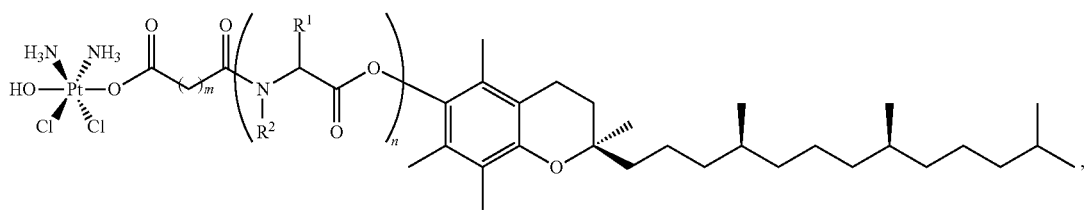

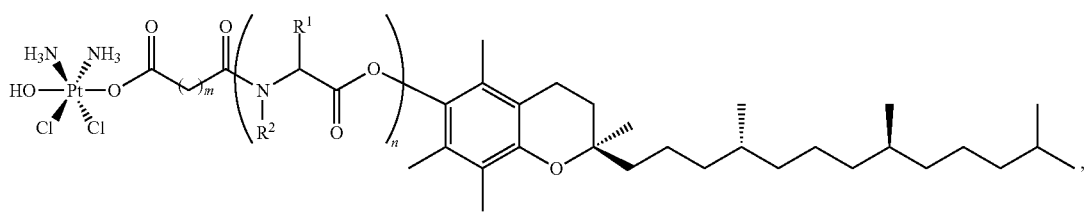

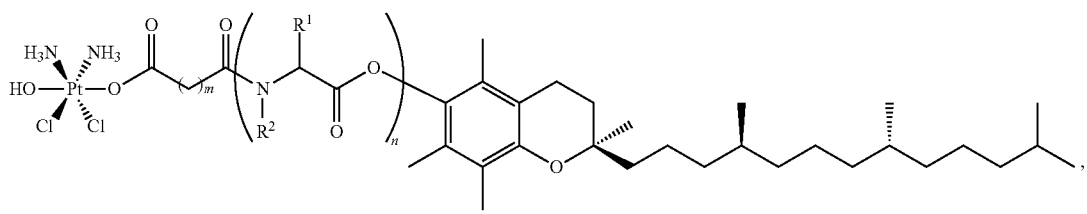

-continued

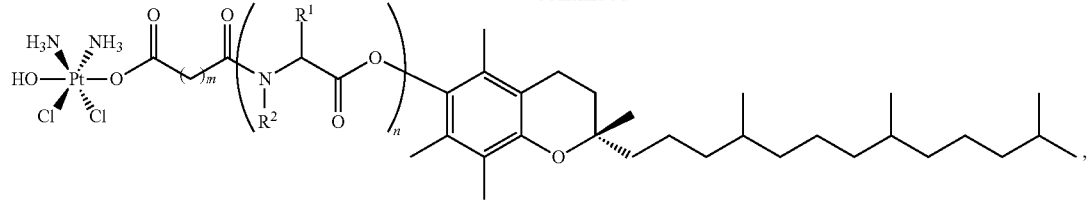

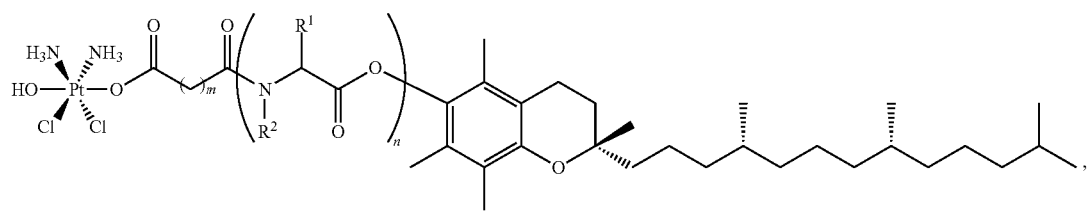

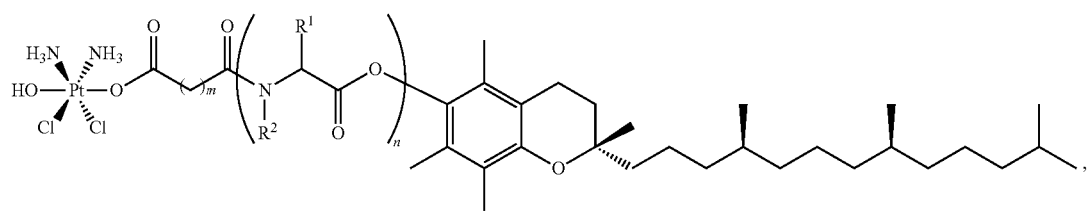

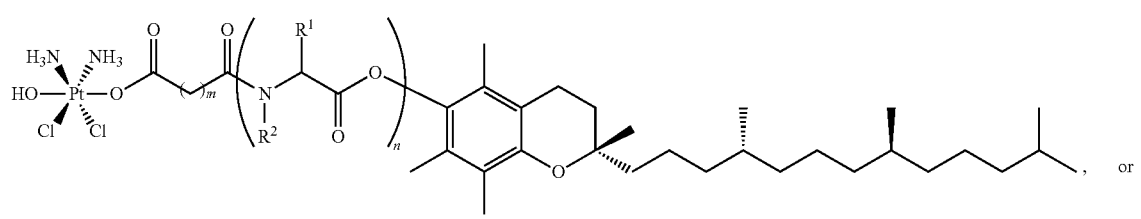, or

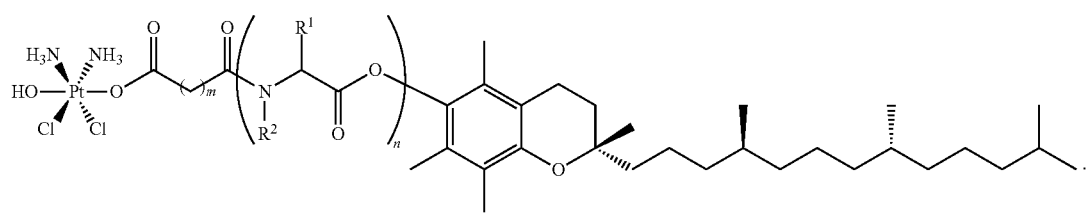.

6. The compound of claim 1, wherein the compound of Formula I has the formula

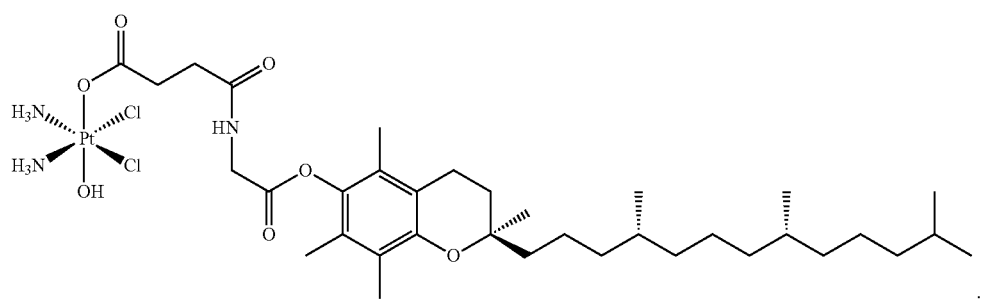

7. A composition comprising the compound of claim 1, a pharmaceutically acceptable carrier, and optionally a hyaluronan-tocopherol conjugate.

8. The composition of claim 7, wherein the composition comprises, the compound, the pharmaceutically acceptable carrier, and the hyaluronan-tocopherol conjugate.

9. The composition of claim 8, wherein the composition comprises an emulsion of the compound and the hyaluronan-tocopherol conjugate.

10. The composition of claim 7, wherein the wherein hyaluronan of the hyaluronan-tocopherol conjugate is substituted on a molar basis with about 6% of tocopherol.

11. The composition of claim 7, wherein the hyaluronan-tocopherol conjugate is of Formula II, III, IV, V, or a mixture of any two or more thereof:

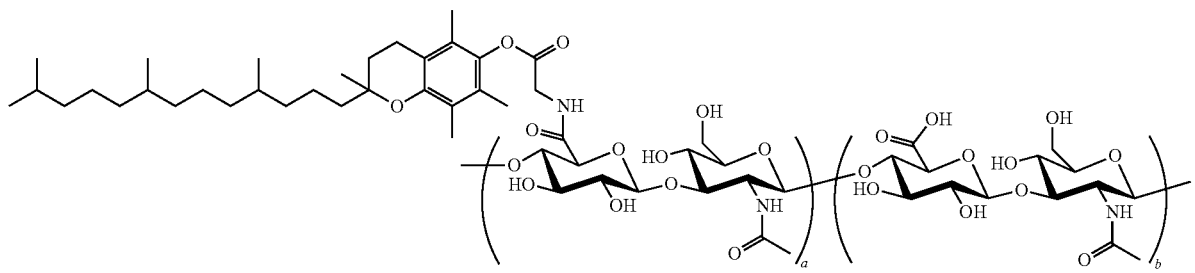

(II)

or a pharmaceutically acceptable salt thereof,

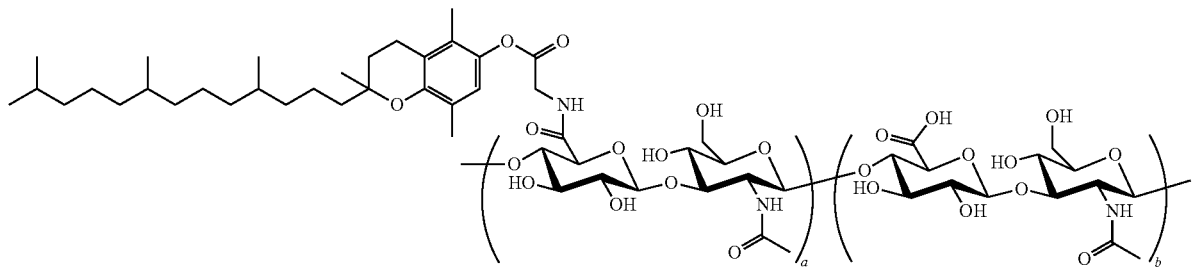

(III)

or a pharmaceutically acceptable salt thereof,

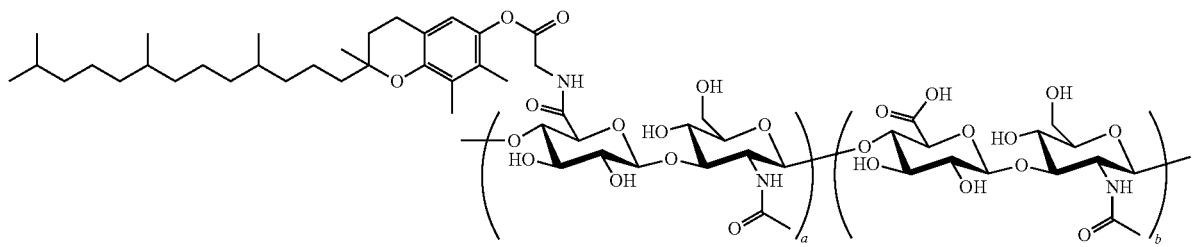

(IV)

or a pharmaceutically acceptable salt thereof,

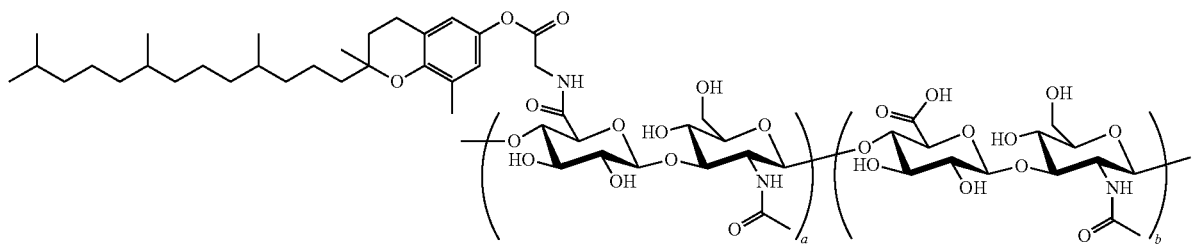

(V)

or a pharmaceutically acceptable salt thereof, wherein a is independently at each occurrence from 1 to 800 and b is independently at each occurrence from 18 to 2540.

12. The composition of claim 11, wherein the hyaluronan-tocopherol conjugate is of Formula IIa

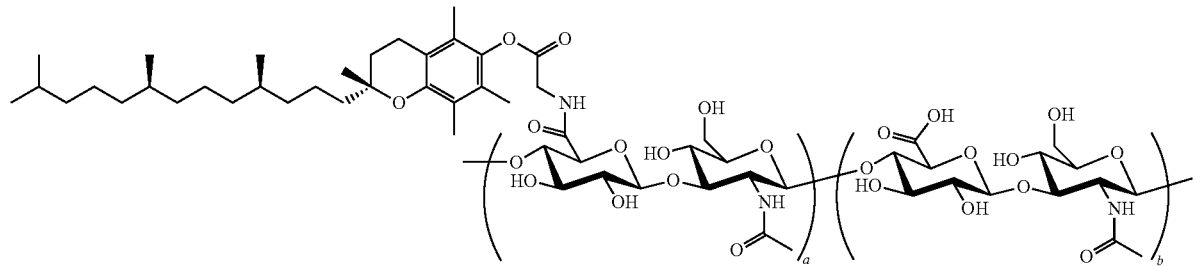

or a pharmaceutically acceptable salt thereof.

13. A method of slowing proliferation of a cancer cell, the method comprising contacting the cancer cell with a compound of claim 1.

14. The method of claim 13, wherein the contacting is in vitro.

15. The method of claim 13, wherein the contacting is in vivo in a subject.

16. The method of claim 13, wherein the method comprises contacting the cancer cell with an effective amount of the compound for slowing proliferation of the cancer cell.

17. A method of slowing or reversing growth of a tumor in a subject, the method comprising administering to the subject an effective amount of a compound of claim 1.

18. The method of claim 17, wherein the tumor is of a cancer selected from the group consisting of squamous cell carcinoma, soft tissue sarcoma, oral melanoma, acute lymphoblastic leukemia (ALL), acute myeloid leukemia (AML), adrenocortical carcinoma, AIDS-related cancers, Kaposi sarcoma, AIDS-related lymphoma, anal cancer, appendix cancer, gastrointestinal carcinoid tumors, astrocytomas, atypical teratoid/rhabdoid tumor, basal cell carcinoma of the skin, bile duct cancer, bladder cancer, bone cancer, brain tumors, breast cancer, bronchial tumors, Burkitt lymphoma, carcinoid tumor, carcinoma of unknown primary, cardiac tumors, childhood brain cancer, germ cell tumor, primary CNS lymphoma, cervical cancer, cholangiocarcinoma, chordoma, chronic lymphocytic leukemia (CLL), chronic myelogenous leukemia (CML), chronic myeloproliferative neoplasms, colorectal cancer, craniopharyngioma, cutaneous T-cell lymphoma, ductal carcinoma in situ (DCIS), embryonal tumors, medulloblastoma, endometrial cancer, ependymoma, esophageal cancer, esthesioneuroblastoma, extracranial germ cell tumor, eye cancer, retinoblastoma, fallopian tube cancer, fibrous histiocytoma of bone, osteosarcoma, gallbladder cancer, gastric cancer, gastrointestinal stromal tumors (GIST), germ cell tumors, childhood central nervous system germ cell tumors, childhood extracranial germ cell tumors, extragonadal germ cell tumors, ovarian germ cell tumors, testicular cancer, gestational trophoblastic disease, hairy cell leukemia, head and neck cancer, heart tumors, hepatocellular cancer, histiocytosis, Hodgkin lymphoma, intraocular melanoma, islet cell tumors, pancreatic neuroendocrine tumors, kidney cancer, Langerhans cell histiocytosis, laryngeal cancer, leukemia, lip and oral cavity cancer, liver cancer, lung cancer, lymphoma, male breast cancer, malignant fibrous histiocytoma of bone and osteosarcoma, melanoma, Merkel cell carcinoma, mesothelioma, metastatic cancer, metastatic squamous neck cancer with occult primary, midline tract carcinoma with nut gene changes, mouth cancer, multiple endocrine neoplasia syndromes, multiple myeloma/plasma cell neoplasms, mycosis fungoides, myelodysplastic syndromes, myelogenous leukemia, myeloid leukemia, myeloproliferative neoplasms, nasal cavity and paranasal sinus cancer, nasopharyngeal cancer, neuroblastoma, non-Hodgkin lymphoma, non-small cell lung cancer, oral cancer, osteosarcoma and malignant fibrous histiocytoma of bone, ovarian cancer, pancreatic cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, plasma cell neoplasm/multiple myeloma, pleuropulmonary blastoma, pregnancy and breast cancer, primary central nervous system (CNS) lymphoma, primary peritoneal cancer, prostate cancer, rectal cancer, recurrent cancer, renal cell cancer, rhabdomyosarcoma, salivary gland cancer, sarcoma, childhood rhabdomyosarcoma, childhood vascular tumors, Ewing sarcoma, Kaposi sarcoma, osteosarcoma, Sézary syndrome, skin cancer, small cell lung cancer, small intestine cancer, squamous cell carcinoma of the skin, squamous neck cancer with occult primary, metastatic, stomach cancer, T-cell lymphoma, throat cancer, oropharyngeal cancer, hypopharyngeal cancer, thymoma and thymic carcinoma, thyroid cancer, tracheobronchial tumors, transitional cell cancer of the renal pelvis and ureter, urethral cancer, uterine cancer, uterine sarcoma, vaginal cancer, vascular tumors, vulvar cancer, and Wilms tumor.

19. The method of claim 17, wherein the administering comprises local administration to the tumor.

20. The method of claim 17, wherein the administering comprises about 1 mg to about 20 mg of the compound administered per $m^2$ of body surface area of the subject.

21. The method of claim 17, wherein the administering comprises oral, rectal, nasal, vaginal, transdermal, intravenous, intramuscular, or inhalation administration.

22. The method of claim 17, wherein the administering comprises injection of the compound into the tumor or proximal to the tumor.

23. A method of treating cancer in a subject, the method comprising administering to the subject an effective amount of a compound of claim 1.

24. The method of claim 23, wherein the cancer is selected from the group consisting of squamous cell carcinoma, soft tissue sarcoma, oral melanoma, acute lymphoblastic leukemia (ALL), acute myeloid leukemia (AML), adrenocortical A carcinoma, AIDS-related cancers, Kaposi sarcoma, AIDS-related lymphoma, anal cancer, appendix cancer, gastrointestinal carcinoid tumors, astrocytomas, atypical teratoid/rhabdoid tumor, basal cell carcinoma of the skin, bile duct cancer, bladder cancer, bone cancer, brain tumors, breast cancer, bronchial tumors, Burkitt lymphoma, carcinoid tumor, carcinoma of unknown primary, cardiac tumors, childhood brain cancer, germ cell tumor, primary CNS lymphoma, cervical cancer, cholangiocarcinoma, chordoma, chronic lymphocytic leukemia (CLL), chronic myelogenous leukemia (CML), chronic myeloproliferative neoplasms, colorectal cancer, craniopharyngioma, cutaneous T-cell lymphoma, ductal carcinoma in situ (DCIS), embryonal tumors, medulloblastoma, endometrial cancer, ependymoma, esophageal cancer, esthesioneuroblastoma, extracranial germ cell tumor, eye cancer, retinoblastoma, fallopian tube cancer, fibrous histiocytoma of bone, osteosarcoma, gallbladder cancer, gastric cancer, gastrointestinal stromal tumors (GIST), germ cell tumors, childhood central nervous system germ cell tumors, childhood extracranial germ cell tumors, extragonadal germ cell tumors, ovarian germ cell tumors, testicular cancer, gestational trophoblastic disease, hairy cell leukemia, head and neck cancer, heart tumors, hepatocellular cancer, histiocytosis, Hodgkin lymphoma, intraocular melanoma, islet cell tumors, pancreatic neuroendocrine tumors, kidney cancer, Langerhans cell histiocytosis, laryngeal cancer, leukemia, lip and oral cavity cancer, liver cancer, lung cancer, lymphoma, male breast cancer, malignant fibrous histiocytoma of bone and osteosarcoma, melanoma, Merkel cell carcinoma, mesothelioma, metastatic cancer, metastatic squamous neck cancer with occult primary, midline tract carcinoma with nut gene changes, mouth cancer, multiple endocrine neoplasia syndromes, multiple myeloma/plasma cell neoplasms, mycosis fungoides, myelodysplastic syndromes, myelogenous leukemia, myeloid leukemia, myeloproliferative neoplasms, nasal cavity and paranasal sinus cancer, nasopharyngeal cancer, neuroblastoma, non-Hodgkin lymphoma, non-small cell lung cancer, oral cancer, osteosarcoma and malignant fibrous histiocytoma of bone, ovarian cancer, pancreatic cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, plasma cell neoplasm/multiple myeloma, pleuropulmonary blastoma, pregnancy and breast cancer, primary central nervous system (CNS) lymphoma, primary peritoneal cancer, prostate cancer, rectal cancer, recurrent cancer, renal cell cancer, rhabdomyosarcoma, salivary gland cancer, sarcoma, childhood rhabdomyosarcoma, childhood vascular tumors, Ewing sarcoma, Kaposi sarcoma, osteosarcoma, Sézary syndrome, skin cancer, small cell lung cancer, small intestine cancer, squamous cell carcinoma of the skin, squamous neck cancer with occult primary, metastatic, stomach cancer, T-cell lymphoma, throat cancer, oropharyngeal cancer, hypopharyngeal cancer, thymoma and thymic carcinoma, thyroid cancer, tracheobronchial tumors, transitional cell cancer of the renal pelvis and ureter, urethral cancer, uterine cancer, uterine sarcoma, vaginal cancer, vascular tumors, vulvar cancer, and Wilms tumor.

25. The method of claim 23, wherein the administering further comprises the administration of an immunotherapy to the subject.

26. The method of claim 25, wherein the immunotherapy comprises veresimod.

27. The method of claim 25, wherein the immunotherapy is administered concurrently with the compound.

28. The method of claim 25, wherein the immunotherapy is administered sequentially with the compound.

29. The method of claim 23, wherein the administering further comprises administration of a chemotherapeutic agent selected from the group consisting of an alkylating agent; a nitrosourea; an antimetabolite; an anthracycline; a topoisomerase II inhibitor; a mitotic inhibitor; an anti-estrogen; a progestin; an aromatase inhibitor; an anti-androgen; an LHRH agonist; a corticosteroid hormone; a DNA alkylating agent; a taxane; a vinca alkaloid; a microtubule poison, and a combination of any two or more thereof.

30. The method of claim 23, wherein the administering further comprises administration of a chemotherapeutic agent selected from the group consisting of busulfan, cisplatin, carboplatin, oxaliplatin, an octahedral platinum (IV) compound, chlorambucil, cyclophosphamide, ifosfamide, dacarbazine, mechlorethamine, melphalan, temozolomide, carmustine, lomustine, 5-fluorouracil, capecitabine, 6-mercaptopurine, methotrexate, gemcitabine, cytarabine, fludarabine, pemetrexed, daunorubicin, doxorubicin, epirubicin, idarubicin, mitoxantrone, topotecan, irinotecan, etoposide, teniposide, paclitaxel, docetaxel, vinblastine, vincristine, vinorelbine, prednisone, dexamethasone, L-asparaginase, dactinomycin, thalidomide, tretinoin, imatinib, gefitinib, erlotinib, rituximab, bevacizumab, ipilimumab, nivolumab, pembrolizumab, tamoxifen, fulvestrant, anastrozole, exemestane, letrozole, megestrol acetate, bicalutamide, flutamide, leuprolide, goserelin, and a combination of any two or more thereof.

* * * * *